United States Patent [19]
Segers et al.

[11] Patent Number: 6,013,266
[45] Date of Patent: Jan. 11, 2000

[54] **LIVE ATTENUATED BACTERIA OF THE SPECIES *ACTINOBACILLUS PLEUROPNEUMONIAE***

[75] Inventors: Ruud Philip Antoon Maria Segers, Boxmeer, Netherlands; Joachim Frey, Schupfen, Switzerland

[73] Assignee: Akzo Nobel, N.V., Arnhem, Netherlands

[21] Appl. No.: 09/057,570

[22] Filed: Apr. 9, 1998

[30] Foreign Application Priority Data

Apr. 10, 1997 [EP] European Pat. Off. ............. 97201032

[51] Int. Cl.[7] ....................... A61K 39/085; A61K 39/12; A61K 39/00; A01N 63/00
[52] U.S. Cl. ................. 424/234.1; 424/93.2; 424/186.1; 424/192.1; 424/199.1; 435/6; 435/29; 435/69.1; 435/69.7; 435/252.33; 435/317.1; 435/320.1; 435/325
[58] Field of Search ................................ 424/93.2, 192.1, 424/199.1, 186.1, 234.1; 435/6, 29, 69.1, 69.7, 252.33, 317.1, 320.1, 325

[56] References Cited

FOREIGN PATENT DOCUMENTS

WO97/16532  11/1995  Australia ......................... C12N 1/21

OTHER PUBLICATIONS

Timothy J. Anderson, Thesis, University of Guelph, Nov. 1995, Characterization of the LACZ, GALK, and GALM Genes of *Actinobacilus Pleuropneumoniae*.

Anderson et al. 1991. Isolation and Molecular characterization of Spontaneously Occuring Cytolysin–Negative Mutants of *Actinobacillus pleuropneumoniae* Serotpre 7. Infection and Immunity. 59 (11): 4110–4116.

Frey, J. 1995, Virulence in *Actinobacillus pleuropneumoniae* and RTX toxins. Trends in Microbiology. 3(7): 257–261.

Jansen et al. 1995. Knockout Mutants of *Actinobcillus pleuropneumoniae* Serotype 1 That Are Devoid of RTX Toxins Do Not activate or Kill Porcine Neutrophils. Infection and Immunity. 63(1):27–37.

Michalski, J. et al. 1993. CVD110, an Attenuated *Vibrio cholerae* 01 E1 Tor Live Oral vaccine Strain. Infection and Immunity. 61(10):4462–4468.

Rosendal et al. 1990. Characterization of an attenuated strain of *Actinobacillus pleuropneumoniae*, serotype 1. American Journal of Veterinary Research. 51(5): 711–717.

Tascon et al. 1994. The RTX haemolysins ApxI and ApxII are major virulence factors of the swine pathogen *Actinobacillus pleuropneumoniae*: evidence from mutational analysis. Molecular Microbiology. 14(2): 207–216.

Frey et al., *Schweizer Archiv Für Tierheilkunde*, 138:3:121–124, 1996.

*Primary Examiner*—James C. Housel
*Assistant Examiner*—Ja-Na Hines
*Attorney, Agent, or Firm*—Mary E. Gormley

[57] ABSTRACT

The present invention relates to live attenuated bacteria of the genus *Actinobacillus pleuropneumoniae* that have a mutation in an apxIV gene such that no functional ApxIV toxin can be produced. The invention also relates to methods for the production of such bacteria. Also vaccines comprising such bacteria and methods for the production of such vaccines are part of the invention. The invention further relates to subunit vaccines comprising an ApxIV toxin, to methods the production of such vaccines and to methods for the protection of animals against infection with bacteria of the genus *Actinobacillus pleuropneumoniae*. In addition, the invention relates to the promotor of the apxIV gene. Finally, the invention relates to diagonostic tests for the selective diagnosis of *Actinobacillus pleuropneumoniae* infections and to diagnostic tests discriminating between *Actinobacillus pleuropneumoniae* field strain and vaccine strains.

14 Claims, 7 Drawing Sheets

```
         1                                                           60
REP1var1A  ..........  ........YG ADTYIFS KGHGQDIVYE DTNNDNRARD IDTLKFTDVN YAEVKFRRVD
REP1var1B  GGKGNDILRG  GYGADTYIFS KGHGQDIVYE DTNNDNRARD IDTLKFTDVN YAEVKFRRVD
REP1var1C  GGKGNDILRG  GYGADTYIFS KGHGQDIVYE DTNNDNRARD IDTLKFTDVN YAEVKFRRVD
REP1var1D  GGKGNDILRG  GYGADTYIFS KGHGQDIVYE DTNNDNRARD IDTLKFTDVN YAEVKFRRVD
REP1var1E  GGKGNDILRG  GYGADTYIFS KGHGQDIVYE DTNNDNRARD IDTLKFTD.. ..........
REP1var3A  ..........  ........YG ADTYIFS KGHGQDIVYE .......... .......... ..........
REP1var3B  GGKGNDILRG  GYGADTYIFS KGHGQDIVYE .......D   IDTLKFTDVN YAEVKFRRVD
REP1var3C  GGKGNDILRG  GYGADTYIFS KGHGQDIVYE DTNNDNRARD IDTLTFTDVN YAEVKFRRVD
REP1var3D  GGKGNDILRG  GYGADTYIFS KGHGQDIVYE DTNNDNRARD IDTLKFTD.. ..........

61                                              102
REP1var1A  NDLMLFGYHD TDSVTVKSFY SHVDYQFDKL EFADRSITRD EL
REP1var1B  NDLMLFGYHD TDSVTVKSFY NHVDYQFDKL EFADRSITRD EL
REP1var1C  NDLMLFGYHD TDSVTVKSFY SHVDYQFDKL EFADRSITRD EL
REP1var1D  NDLMLFGYHD TDSVTVKSFY NHVDYQFDKL EFADRSITRD EL
REP1var1E  .......... .......... .......... .......... ..
REP1var3A  .......... .......... .......... .......... ..
REP1var3B  NDLMLFGYHD TDSVTVKSFY SHVDYQFDKL EFADRSITRD EL
REP1var3C  NDLMLFGYHD TDSVTIKSFY NHVDYQCDKL DFADRSITRD EL
REP1var3D  .......... .......... .......... .......... ..

FIG. 2A 1                                              27
REP2var1A  IKAGLHLYGT DGNDDIKDHA DWDSILE
REP2var1B  IKAGLHLYGT DGNDDIKDHA DWDSILE
REP2var3A  IKAGLHLYGT DGNDDIKDHA DWDSIVE

FIG. 2B 1                                                           44
REP3var1A  GKQGMALFGT DGDDNINDWG RNSVIDAGAG NDTVNGGNGD DTLI
REP3var1B  GKQGMALFGT DGDDNINDWG RNSVIDAGAG NDTVNGGNGD DTLI
REP3var3A  GKQGMALFGT DGDDNINDWG RNSVIDAGAG NDTVNGGNGD DTLI

FIG. 2C
```

LIVE ATTENUATED BACTERIA OF THE SPECIES *ACTINOBACILLUS PLEUROPNEUMONIAE*

FIELD OF THE INVENTION

The present invention relates to live attenuated bacteria of the genus *Actinobacillus pleuropneumoniae*, having a mutation in a gene encoding a toxin, methods for the production of such bacteria, to vaccines comprising such bacteria, methods for the production of such vaccines, to vaccines comprising a toxin, methods for the production of such vaccines and methods for the protection of animals against infection with bacteria of the genus *Actinobacillus pleuropneumoniae*.

BACKGROUND OF THE INVENTION

Bacteria belonging to the genus *Actinobacillus* all produce so-called RTX-toxins. (RTX stands for repeat in toxin).

It is the presence of these RTX-toxins that highly contributes to the pathogenic character of these bacteria.

The RTX-toxins have been extensively reviewed by Braun et al. (Critical Rev. in Microbiol. 18(2): 115–158 (1991)). RTX-toxins in Gram-negative strains have also been reviewed in Welch, R.A. (Molecular Microbiology 5/3: 521–528 (1991)) and in Welch et al. (Inf. Agents and Disease 4: 254–272 (1995)).

All known RTX-toxins display some kind of cytotoxic or cytolytic activity. The target-cell-and host-specificity differ however, depending on the toxin and on differences in acylation (McWhinney et al.; J. Bact. 174: 291–297 (1992) and Hackett et al.; J. Biol. Chem. 270: 20250–20253 (1995)). As a result of the difference in target cells, the various toxins of the RTX-toxin family are known e.g. as haemolysin, cytolysin or cytotoxin.

The genus Actinobacillus comprises a number of different species, inter alia, *Actinobacillus pleuropneumoniae, A. actinomycetemcomitans, A. suis, A. rossii, A. equuli* and *A. lignieresii*.

*Actinobacillus pleuropneumoniae* produces serotype-dependent RTX-toxins that are cytotoxic/cytolytic to pig, horse, bovine and human erythrocytes, to rabbit and porcine neutrophils and to porcine alveolar macrophages. (Rosendal et al; Am. J. Vet. Res. 49: 1053–1058 (1988), Maudsley J. R. and Kadis S; Can. J. Microbiol. 32: 801–805 (1986), Frey. J and Nicolet. J; Inf. & Imm. 56:2570–2575 (1988), Bendixon et al; Inf. & Imm. 33: 673–676 (1981), Kamp, E. M. and van Leengoed, L. A. M. G. ; J. Clin. Microbiol. 27: 1187–1191 (1989)).

Infections with Actinobacillus in pigs are the cause of severe economic losses to pig industry, due to acute mortality in young pigs and reduced weight gain in older animals.

The genetic organisation of the operons involved in the synthesis, activation and transportation of the RTX toxins in Gram-negative bacteria has been reviewed recently by Coote, J. G. (FEMS Microbiology reviews 88: 137–162 (1992)). Frey has specifically reviewed the known three RTX-toxins in *Actinobacimlus pleuropneumoniae* in Bacterial Protein Toxins, Zbl Bakt. Suppl. 24, p. 322-, Freer et al. (Eds.), Gustaf Fischer, Stutttgart, Jena, New York, 1994.

In *Actinobacillus pleuropneumoniae*, this kind of RTX-operon contains four genes: the actual Toxin-gene (A), an Activator-gene (C), and two genes (B and D) encoding proteins involved in secretion of the toxin into the surrounding medium. The primary translation-product of the Toxin-gene (A) is a non-toxic protein, of which the toxic activity is activated by the Activator-gene (C) product.

Until recently, it was assumed that only three RTX-toxins, all having the above-described genetic organisation or at least having the Toxin-gene (A) and Activator-gene (C), existed in Actinobacillus species.

These three RTX-toxins, ApxI, Apx-II and Apx-III have respectively a pronounced haemo-lytic activity (ApxI), a mild haemolytic activity (Apx-II) or a macrophage-cytotoxic activity (Apx-III).

The various toxic activities are fairly randomly divided over the serotypes. There are four subgroups:

a subgroup A, represented by serotypes 1, 5, 9 and 11, producing ApxI and Apx-II,
 a subgroup B, represented by serotypes 2, 3, 4, 6 and 8, producing Apx-II and Apx-III,
 a subgroup C, represented by serotype 10, producing ApxI only,
 a subgroup D, represented by serotype 7 and 12, producing Apx-II only, It is known, that ApxI, -II, and -III all are essential elements in universal vaccines against *Actinobacillus pleuropneumoniae* infection: a vaccine not comprising at least ApxI, -II, and -III will not provide protection against all *Actinobacillus pleuropneumoniae* serotypes. Also, a vaccine not comprising at least the Apx-toxins of one specific serotype will not even induce protection against that single serotype.

Subunit vaccines based on in vitro synthesised RTX-toxins from *A. pleuropneumoniae* that lost their toxicity have been described earlier, e.g. in European Patent EP No. 0.354.628, in which subunit vaccines based upon a haemolysin and a cytotoxin of *A. pleuropneumoniae* are disclosed, and in European Patent EP No 0.453.024, in which *A. pleuropneumoniae* subunit vaccines based upon haemolysins, cytotoxins and outer membrane proteins are disclosed.

There are however four important disadvantages to subunit vaccines in general:

high amounts of antigenic material are needed in order to adequately trigger the immune system.
 usually, only B-cell immunity is triggered.
 several protective antigens are only triggered in vivo, and therefore can not be present in subunit vaccines.
 a live pathogenic bacterium has many important immunogenic molecules, such as Outer Membrane Proteins and capsular polysaccharides, all potentially important for protection and thus to be included in an efficient subunit vaccine.

Next to the obvious problems mentioned under points one and two, especially the fourth point makes it difficult to make an efficient subunit vaccine.

This is e.g. illustrated by the *A. pleuropneumoniae* subunit vaccine disclosed in European Patent EP No 0.453.024 mentioned above, in which four different subunits (three RTX-toxins and an outer membrane protein) are combined in one vaccine.

It is clear, that in order to overcome the disadvantages of subunit vaccines against Pasteurellaceae-infection, a live attenuated vaccine would be highly desirable.

A live attenuated vaccine has the following advantages:

it can be administered in low doses (it is self-replicating)
 it closely mimics the natural/wild-type infection
 it provides all the possible immunologically important antigens at the same time.

Nevertheless, in spite of the clear advantages, no live vaccines based on *Actinobacillus pleuropneumoniae* were commercially available prior to the present invention.

The reason for this lies in the following paradox: as mentioned before, ApxI, -II, and -III all are essential elements of universal vaccines against *Actinobacillus pleuropneumoniae* infection. Live vaccines therefore have to produce these three RTX-toxins. These three RTX-toxins are however strong virulence factors in all Actinobacillus species (see e.g. Coote, J. G.; FEMS Microbiology reviews 88: 137–162 (1992), Tascon et al.; Mol. Microbiol. 14: 207–216 (1994)), Jansen et al.; Inf. & Imm. 63: 27–37 (1995)).

Deletion of the RTX-toxins in order to attenuate the virulence of live App strains is technically feasible, but this does not provide a solution for the dilemma: such RTX-negative strains would be useless as live attenuated vaccine strains since they do no longer induce immunity in the host against the haemolyticicytotoxic activity of *Actinobacillus pleuropneumoniae* field strains.

Virulence factors that, although important in the induction of immunity, do play a less important role in building up immunity than ApxI, -II and -III, and thus can in principle be deleted are however currently not known.

It would thus be highly desirable to have a site on the genome of App that attributes to virulence and therefore leads to an attenuated App strain when modified, whereas at the same time it is, although useful in triggering immunity, dispensable from a vaccine point of view. No such sites are however currently known. Moreover, it would be highly desirable if such a site would be universally present in all App strains, instead of being restricted to certain serotypes. Such a site would then allow all different serotypes to be attenuated by deletion of that same site.

It is one of the objectives of the present invention to provide such an attenuation site, universally present in all *Actinobacillus pleuropneumoniae* strains regardless their serotype.

Recently, a new gene was found in a serotype 1 strain of *Actinobacillus pleuropneumoniae* (Thesis T. J. Anderson Nov. 1995).

Although this gene does not resemble the known Actinobacillus ApxI, -II and -III genes, it bears resemblance to RTX-toxin genes known from bacteria belonging to *Neisseria meningitidis*, for which reason it was named RTX-gene apxIV. The gene however differs in almost all aspects from the three known RTX-toxin genes apxI, -II and -III present in the various species of the Actinobacillus family as described above. First of all, the genomic organisation is completely different. Secondly, there is no activator-mechanism as is found for the known Apx-toxins. In the third place, no specific in vivo haemolytic or cytotoxic activity could at that time be attributed to the gene, or its possible gene product.

SUMMARY OF THE INVENTION

It was now surprisingly found that this gene, fully in contrast with the three known RTX-genes, is present in all bacteria of the species *Actinobacillus pleuropneumoniae*, regardless their serotype. This was determined by hybridisation of a probe comprising apxIV coding sequences with restriction fragments of the DNA from *Actinobacillus pleuropneumoniae* of all serotypes as described in Example 6 and 7.

Unexpectedly it was found now, that apxIV deletion mutants are viable, but they behave less virulent compared to their apxIV-possessing parent strains.

Therefore, it was determined that the gene product, the ApxIV toxin is a virulence factor in all *Actinobacillus pleuropneumoniae* strains. This is an unexpected conclusion, since up until now, no effects at all, let alone effects possibly influencing virulence had been attributed to the gene product in vivo. In fact, up until now there was not even proof that the gene was expressed in *Actinobacillus pleuropneumoniae* in vivo or in vitro anyway.

It therefore is one of the merits of the invention that it was found that:

the apxIV gene is present in all *A. pleuropneumoniae* strains regardless the serotype, the apxIV gene product is a virulence factor in all *A. pleuropneumoniae* serotypes,

*A. pleuropneumoniae* strains with a deletion in the apxIV gene are still viable but have a decreased vinulence without significantly impairing the immunogenic properties of the strains, Therefore, the invention provides for the first time live attenuated bacteria of the species *Actinobacillus pleuropneumoniae*, that do not produce a functional ApxIV toxin.

DETAILED DESCRIPTION OF THE INVENTION

A functional ApxIV toxin is considered to be a protein that has all the characteristics of the ApxIV toxin as expressed in a wild-type bacterium, and is expressed at the wild-type level. Therefore, a non-functional ApxIV toxin is considered to be a toxin that lacks some or all of the characteristics of the ApxIV toxin as expressed in a wild-type bacterium, and/or is expressed at a level, insufficient to obtain wild-type effects of ApxIV toxin.

The inability to produce the ApxIV toxin can e.g. be due to modifications in the coding sequence encoding the ApxIV toxin. It may also be e.g. the result of modifications in regions known to be involved in transcription of the apxIV gene, such as the promotor region, or of modifications in regions involved in translation, such as the ribosome binding site.

Figure 1:
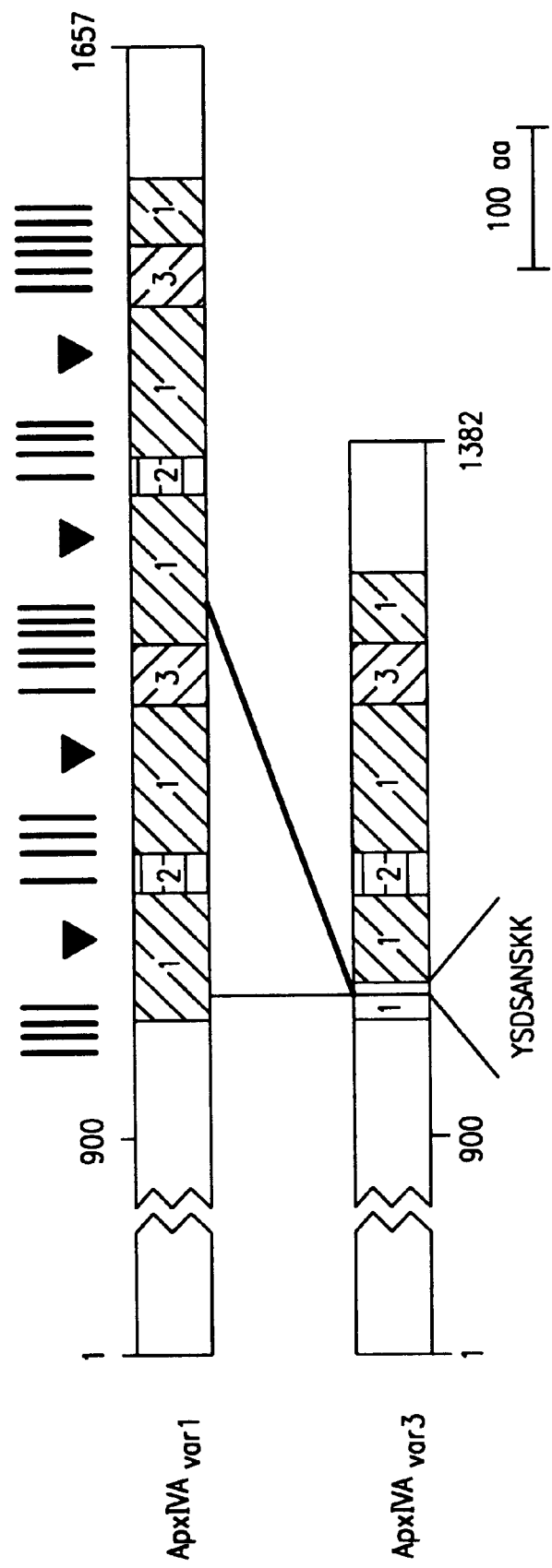

The overall structure of the apxIV gene is given in FIG. 1.

In this figure, the direct repeat regions, characteristic for ApxIV toxin are indicated by dashed boxes, whereas the also ApxIV-specific glycine-rich nonapeptide regions are indicated by black arrows. The repeats are found at the C-terminal part of ApxIV. These characteristic features are present in all *Actinobacillus pleuropneumoniae* serotypes. The nucleic acid sequence and amino acid sequence of two serotypes are represented in SEQ. ID. No. 1–4. SEQ. ID. NO. 1 shows the nucleic acid sequence of the apxIV gene of App serotype 1, and SEQ. ID. NO. 2 shows the matching amino acid sequence of the serotype 1 ApxIV toxin. SEQ. ID. NO. 3 shows the nudeotide sequence of the apxIV gene of App serotype 3, whereas SEQ. ID. NO. 4 shows the matching amino acid sequence of the serotype 3 ApxIV toxin. FIG. 2 shows the strikingly high level of conservation at amino acid level, especially in the N-terminal 650 amino acids, between the Apx-toxins of the various *Actinobacillus pleuropneumoniae* serotypes. This is also a remarkable characteristic of the apxIV genes. It is clear from FIG. 1, that a variation in the number of repeats at the C-terminal part of the toxin may occur, depending on the serotype. This variation accounts for the difference in size of the genes and encoded toxins obtained from the various serotypes.

There may be some variation in nucleic acid sequence even between apxIV genes isolated from different isolates of

*Actinobacillus pleuropneumoniae*, belonging to the same serotype. This is due to natural variation well known in the art to exist in all organisms. It is possible that some amino acids in the ApxIV toxin encoded by the apxIV gene are replaced by others in the ApxIV toxin of another serotype, while the polypeptide is not altered in its function. For instance, a polypeptide containing Asp at a certain site, and its variant containing Asn at the comparable site still have the same properties. This process in which an amino acid is replaced by an functionally analogous amino-acid is called functional displacement. In this case the variant proteins are called functional variants. Another cause of variation is the phenomenon of degeneracy of the genetic code, Shortly, it means, that e.g. the amino acid glutamic acid is coded for by both GAT and GM. This phenomenon holds for all amino acids, except Met and Trp. Thus, it is obvious, that e.g. the ApxIV toxin of serotype 1, as given in the present invention can not only be coded for by the nucleotide sequence given in SEQ ID NO: 1 but also by a very large variety of other sequences, still all giving the same or functionally the same polypeptides.

Therefore, a variant apxIV sequence encoding a polypeptide that is functionally comparable to the ApxIV toxin falls within the scope of the present invention.

Live attenuated bacteria according to the invention can be obtained in several ways. One possible way of obtaining such bacteria is by means of classical methods such as the treatment of wild-type *Actinobacillus pleuropneumoniae* bacteria with mutagenic agents such as base analogues, treatment with ultraviolet light or temperature treatment. Strains that do not produce a functional ApxIV toxin do not or to a lesser extend induce anti-ApxIV toxin antibodies, and therefore can easily be selected in animal tests. The necessary antiserum can be obtained as described below in Example 3.

Another possibility is to deliberately introduce, using recombinant DNA-technology, a well-defined mutation in the gene encoding the ApxIV toxin. Such a mutation may be an insertion, a deletion, a replacement of one nucleotide by another one or a combination thereof, with the only proviso that the mutated gene no longer encodes a functional ApxIV toxin. It can easily be seen, that especially mutations introducing a stop-codon in the open reading frame, or mutations causing a frame-shift in the open reading frame are very suitable to obtain a strain which no longer encodes a functional ApxIV toxin. Such mutations can e.g. be made by means of in vitro site directed mutagenesis using the Transformer® kit sold by Clontech. Many other standard recombinant DNA techniques such as digestion of the gene with a restriction enzyme, followed by endonuclease treatment and religation, are equally applicable.

Therefore, in a preferred form, this embodiment of the invention relates to live attenuated bacteria in which the gene encoding the ApxIV toxin comprises a mutation.

Well-defined mutations involving the deletion of fragments of the apxIV gene or even the whole gene, or the insertion of heterologous DNA-fragments, when compared to classically induced mutations, have the advantage that they will not revert to the wild-type situation.

Thus, in a more preferred form, this embodiment of the invention refers to live attenuated bacteria in which the gene encoding the ApxIV toxin comprises an insertion and/or a deletion.

Given the large amount of vaccines given nowadays to pigs, it is clear that combined administration of several vaccines would be desirable, if only for reasons of decreased vaccination costs. It is therefore very attractive to use live attenuated vaccine strains as a recombinant carrier for heterologous genes, encoding antigens selected from other pathogenic micro-organisms or viruses. Administration of such a recombinant carrier has the advantage that after administration of such a carrier, immunity is induced against two or more diseases at the same time. The live attenuated bacteria according to the present invention provide a very suitable carrier for heterologous genes, since the gene encoding the ApxIV toxin can be used as an insertion site for such heterologous genes. The use of the apxIV gene as an insertion site has the advantage that at the same time the apxIV gene is inactivated, and the newly introduced heterologous gene can be expressed in accordance with the homologous *Actinobacillus pleuropneumoniae* genes. The construction of such recombinant carriers can be done routinely, using standard molecular biology techniques such as homologous recombination. Therefore, in an even more preferred embodiment, the present invention relates to live attenuated bacteria of the species *Actinobacillus pleuropneumoniae* that do not produce a functional ApxIV toxin, and in which there is a heterologous gene inserted in the apxIV gene. Such a heterologous gene can, as mentioned above, e.g. be a gene encoding an antigen selected from other pathogenic micro-organisms or viruses. Another possibility is to insert a gene encoding a protein involved in triggering the immune system, such as an interleukine or an interferone.

In a still even more preferred form of the invention, the heterologous gene encodes one or more antigens selected from the group consisting of Porcine Reproductive Respiratory Syndrome (PRRS) virus, Pseudorabies virus, Porcine Influenza virus, Porcine Parvovirus, Transmissible Gastroenteritis virus, rotavirus, *Eschenchia coli, Erysipelothrix rhusiopathiae, Pasteurella multocida, Bordetella bronchiseptica, Haemophilus parasuis* and *Streptococcus suis*.

There is however a serious pitfall in expression of heterologous genes in recombinant carriers: it is known that several proteins are toxic if they are expressed in heterologous bacteria. Therefore, genes encoding such proteins can never be introduced in heterologous carriers, since successful recombinants will eventually die as a result of the expression a certain amount of the heterologous gene. The P2-protein of *Haemophilus influenzae*, to name just one example, can simply not be expressed in *E. coli*. (Munson et al., Infect. & Immun. 57: 88–94 (1989)). It is one of the objectives of the present invention to offer a recombinant live carrier that does not have this drawback. It was unexpectedly found, that although the apxIV gene is efficiently expressed in vivo (see Example 5), it is not expressed in vitro (see Example 4). This was concluded from the failure to show the presence of ApxIV toxin in in vitro grown *A. pleuropneumoniae* cultures. This means that ApxIV expression is switched on or off, depending on the environment in which *A. pleuropneumoniae* is grown. This feature offers an unexpected advantage over known live recombinant carriers: if the expression of the heterologous gene is brought under the control of the apxIV promoter, the live attenuated *P. pleuropneumoniae* carrier according to the invention can be grown in vitro to high densities, regardless the inserted heterologous gene, since the foreign gene will not be expressed under these conditions. After administering a number of bacteria to the host, the expression of the heterologous gene will start and at some time during replication or after the death of the bacterium it will become available to the immune system of the host. The heterologous gene to be expressed can be functionally linked to the apxIV promoter by e.g. replacing the coding sequence of the apxIV gene by the coding region of the heterologous gene. It is not necessary to replace the whole apxIV gene: it suffices to replace the ATG-codon of ApxIV by the coding region of the heterologous gene including its stop-codon. It is also possible to express a heterologous gene under the influence of the apxIV promoter by making a fusion construct. This can be made by inserting the heterologous gene in frame with the apxIV reading frame down-stream of the apxIV ATG codon.

The wording "functionally linked to the apxIV promoter" means that transcription of the heterologous gene starts at the apxIV promoter.

It goes without saying that each location of the inserted heterologous gene in which it is functionally linked to the apxIV promotor falls within the scope of the invention.

Therefore, the most preferred form of this embodiment relates to live attenuated bacteria according to the present invention, carrying a heterologous gene that is functionally linked to the promotor region of the apxIV gene.

The surprising finding that the native apxIV promotor is a switchable promotor that is switched off in vitro and switched on in vivo makes this promotor a very versatile expression tool both in it's natural host and as a heterologous promotor in other bacteria. When used as a heterologous promotor in other bacteria, the DNA comprising the promotor can be isolated from its host and transferred to a bacterium other than Actinobacillus pleuropneumoniae. Another option that has now become feasible, is the cloning of several copies of the apxIV promotor each controlling the expression of another gene. This can be done in the host bacterium Actinobacillus pleuropneumoniae, but this principle of multiple copies is equally applicable to other bacteria. As mentioned above, the promotor can be used for the selective in vivo expression of one or more heterologous genes encoding antigens selected from other pathogenic micro-organisms or viruses. The promotor can also be used for the expression of a heterologous DNA sequence encoding a cytokine such as an interleukin, Tumor Necrosis Factor or an interferon. Several cytokines, e.g. interferons are known to play an important role as immune modulators. Thus it may be advantageous to express such genetic information under the control of the apxIV promotor.

Therefore, another embodiment of the invention relates to a nucleotide sequence harbouring the promotor controling the expression of the apxIV gene.

The switchable promotor that in the native situation controls the expression of the apxIV gene, was now found to be located in the DNA fragment between position 451 and 1132 of SEQ ID NO: 5. It is clear, that those parts of this DNA fragment that are not essential promotor elements need not necessarily be present in the fragment. Thus, shorter fragments of this DNA fragment in which the promotor activity is retained, are equally suitable for the expression of heterologous genes. Therefore, a more preferred form of this embodiment relates to a nucleotide sequence comprising the DNA fragment from position 451 to 132 of SEQ ID NO: 5 or a subfragment thereof still having promotor activity.

Bacterial promotors all share two consensus regions, the so-called −10 and the −35 region. Although the flanking sequence of these consensus regions may to a certain extend influence the efficiency of the promotor, it can be advantageous to use only that part of the promotor region that comprises the DNA fragment between −35 and the ATG codon. This DNA fragment is located between position 617 and position 641 of SEQ ID NO: 5.

Therefore, in a more preferred form of this embodiment the invention relates to a nucleotide sequence comprising the DNA fragment from position 617 to 641 of SEQ ID NO: 5.

The present invention also relates to ApxIV toxin as a subunit vaccine component. Subunit vaccines will most probably comprise the three known Apx-toxins. This was mentioned above. Since it was unexpectedly found, that the ApxIV toxin is however present in all A. pleuropneumoniae serotypes as mentioned above, it is a desirable additional component of subunit vaccines: neutralising antibodies raised against the ApxIV toxin provide protection against the ApxIV toxin produced by each and every Actinobacillus pleuropneumoniae strain, regardless the serotype. Therefore, another embodiment of the invention relates to subunit vaccines for the protection of animals against infection with a bacterium of the species Actinobacillus pleuropneumoniae, that comprise purified ApxIV toxin. The ApxIV toxin can be administered alone, or in combination with any or all of the toxins ApxI, -II and -III mentioned above and/or e.g. in combination with Outer Membrane Proteins (OMPS) of Actinobacillus pleuropneumoniae. Such vaccines can easily be prepared by admixing ApxIV toxin in an amount sufficient to induce an immune response, and a pharmaceutically acceptable carrier. Production of the ApxIV toxin is possible by introducing the apxIV gene in a suitable expression vector, expression of the gene and isolation of the toxin. Many versatile expression systems are known in the art, such as bacterial expression systems, baculovirus expression systems and mammalian cell expression systems. In Example 3 it is described how to obtain the ApxIV toxin by expression of the gene in E. coli.

Still another embodiment of the invention relates to live attenuated vaccines comprising live attenuated bacteria as described above for the protection of animals against infection with a bacterium of the species Actinobacillus pleuropneumoniae. Such vaccines can be obtained by admixing live attenuated bacteria with a pharmaceutically acceptable carrier. These vaccines comprise at least an immunogenically effective amount of the live attenuated producing bacterium according to the invention. Immunogenically effective means that the amount of live attenuated bacterium administered at the moment of vaccination is sufficient to induce in the host an effective immune response to virulent forms of the RTX-toxin producing bacterium. The useful dosage to be administered will vary depending on the age, weight and animal vaccinated, the mode of administration and the type of pathogen against which vaccination is sought. The vaccine may comprise any dose of bacteria, sufficient to evoke an immune response. Doses ranging between $10^3$ and $10^{10}$ bacteria are e.g. very suitable doses.

The pharmaceutically acceptable carrier may be as simple as water, but it may e.g. also comprise culture fluid in which the bacteria were cultured. Another suitable carrier is e.g. a solution of physiological salt concentration. Other examples of pharmaceutically acceptable carriers or diluents useful in the present invention include stabilisers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

Optionally, one or more compounds having adjuvant activity may be added to the vaccine. Adjuvantia are non-specific stimulators of the immune system. They enhance the immune response of the host to the invading pathogen. Examples of adjuvantia known in the art are Freunds Complete and Incomplete adjuvans, vitamin E, non-ionic block polymers, muramyldipeptides, ISCOMs (immune stimulating complexes, cf. for instance European Patent ER 109942), Saponins, mineral oil, vegetable oil, and Carbopol (a homopolymer). Adjuvantia, specially suitable for mucosal application are e.g. the *E. coli* heat-labile toxin (LT) or Cholera toxin (CT).

Other suitable adjuvants are for example aluminium hydroxide, phosphate or oxide, oil-emulsions (e.g. of Bayol F $^{(R)}$ or Marcol 52$^{(R)}$, saponins or vitamin-E solubilisate.

Therefore, in a preferred form, the vaccines according to the present invention comprise an adjuvant.

For administration to animals, the vaccine according to the presentation can be given inter alia intranasally, intradermally, subcutaneously, by aerosol or intramuscularly.

There are several ways to store both subunits and live organisms. Storage in a refrigerator is e.g. a well-known method. Also often used is storage at −70° C. in a buffer containing glycerol. Bacteria can also be kept in liquid nitrogen. Freeze-drying is another way of conservation. Freeze-dried bacteria can be stored and kept viable for many years. Storage temperatures for freeze-dried bacteria may well be above zero degrees, without being detrimental to the viability. Freeze-drying is equally applicable for subunits. Freeze-drying can be done according to all well-known standard freeze-drying procedures. Optional beneficial additives, such as e.g. skimmed milk, trehalose, gelatin or bovine serum albumin can be added in the freeze-drying process.

Therefore, in a more preferred embodiment, the vaccine according to the present invention is in a freeze-dried form.

In an even more preferred form of this embodiment, the vaccine additionally comprises one or more antigens selected from other pathogenic micro-organisms or viruses. Such a vaccine can be obtained by adding one or more antigens selected from other pathogenic bacteria or viruses to the live attenuated bacterium according to the invention and a pharmaceutically acceptable carrier as described above.

Of course, it is possible to add not only one or more antigens, but also one or more of the whole pathogens as such, in an inactivated or live form.

It can alternatively be obtained by cloning the genetic information encoding one or more antigens selected from other pathogenic micro-organisms or viruses into the live attenuated bacterium, using known recombinant DNA technology as described above.

Such vaccines are of course less stressing for the animal to be vaccinated than separate vaccinations with each of the pathogens, both from a medical and a physical point of view.

In a still even more preferred form, these antigens are selected from the group consisting of Porcine Reproductive Respiratory Syndrome (PRRS) virus, Pseudo-rabies virus, Porcine Influenza virus, Porcine Parvovirus, Transmissible Gastroenteritis virus, rotavirus, *Escherichia cogi, Erysipelothrix rhusiopathiae, Pasteurella muftocida, Bordetella bronchiseptica, Haemophilus parasuis* and *Streptococcus suis*.

The invention also relates to methods for the preparation of a live attenuated bacterium of the species *Actinobacillus pleuropneumoniae* that is not capable of producing a functional ApxIV toxin. These method comprise the introduction of a mutation in the gene encoding the apxIV protein. Both classical mutation techniques, using mutagenic agents, and recombinant DNA techniques well-known in the art for insertion, replacement or deletion of genetic information from the apxIV gene are applicable.

In a preferred form, the above mentioned methods are used for the introduction of a deletion.

Methods for the preparation of a live attenuated vaccine according to the invention, that comprise admixing bacteria according to the invention with a pharmaceutically acceptable carrier are also part of the invention.

Also falling within the scope of the invention are methods for the preparation of a subunit vaccine. Such methods comprise the mixing of purified ApxIV toxin with a pharmaceutically acceptable carrier.

Another generally acknowledged problem in the field of vaccination with live vaccines is the following: the presence of antibodies against a certain pathogen in the serum of a host animal indicates that the host has been infected with the pathogen, either in a virulent or attenuated form. It is however impossible to discriminate between field-infected animals and animals vaccinated with a live vaccine strain. The live attenuated *Actinobacillus pleumpneumoniae* according to the present invention offers a solution to this problem as follows:

As described in Example 3, the apxIV gene of *Actinobacillus pleuropneumoniae* serotype 1 has been isolated and expressed in a heterologous host cell. This expression product was subjected to PAGE-gelelectroforesis and then used for Western-blotting. The blots were incubated with convalescent serum obtained from a deliberately *Actinobacillus pleuropneumoniae*-infected pigs, and sera from field-strains. It was found, that the apxIV gene is expressed in vivo in all *Actinobacillus pleuropneumoniae* field strains tested. This implicates, that pigs infected with *Actinobacillus pleuropneumoniae* will always have anti-bodies against the strain with which they were infected, regardless the serotype of the infectious strain.

The live attenuated bacteria according to the present invention can, due to the deletion of the apxIV gene, no longer make ApxIV toxin. Therefore animals vaccinated with a live attenuated *Actinobacillus pleuropneumoniae* strain according to the invention will not have antibodies against ApxIV toxin in their serum.

In a comparative test, e.g. an ELISA test, such sera will therefore react with all immunogenic *Actinobacillus pleuropneumoniae*-proteins such as e.g. ApxI, II and/or III, but not with ApxIV. Sera from pigs infected with an *Actinobacillus pleuropneumoniae* field strain however will react with all immunogenic *Actinobacillus pleuropneumoniae*-proteins, including ApxIV. Therefore, the live attenuated *Actinobacillus pleuropneumoniae* according to the present invention turns out to be a very suitable marker vaccine, i.e. a vaccine strain that can be discriminated from a field strain.

A diagnostic test for the discrimination between vaccine strains and field strains can be a simple ELISA-test in which purified ApxIV toxin is coated to the wall of the wells of an ELISA-plate. Incubation with serum from pigs to be tested, followed by e.g. incubation with a labelled anti-pig antibody can then reveal the presence or absence of antibodies against ApxIV toxin.

Another example of a diagnostic test system is e.g. the incubation of a Western blot comprising purified ApxIV toxin with serum of pigs to be tested, followed by detection of specific anti-ApxIV antibodies.

Therefore, diagnostic test for the discrimination between sera from pigs infected with *Actinobacillus pleuropneumoniae* field strains and from pigs vaccinated with a vaccine comprising live attenuated vaccine *Actinobacillus pleuropneumoniae* strains according to the invention, that comprise purified ApxIV toxin. also fall within the scope of the invention.

Still another problem seen in pig health care is the following: It is difficult to determine in a both quick and unambiguous manner if a pig is infected with *Actinobacillus pleuropneumoniae* or *A. suis*, or possibly a combination of both. Diagnostic tests for the specific detection of *A. suis* are currently not available. This is mainly due to the fact that *A. pleuropneumoniae* and *A. suis* share so many antigens. As an example --, --; two highly antigenic Apx-toxins; --Apx-toxins, ApxI and ApxII, --have highly conserved homologues in e.g. *A. suis* (Van Ostaayen et al., submitted for publication). The known RTX-genes, encoding the ApxI, -II and -III toxins or homologues are found in practically all members of the genus Actinobacillus, such as *A. pleuropneumoniae, A. suis, A. rossii* and *A. equuli*. Thus, it was initially assumed by the inventors, that the new RTX-toxin ApxIV would also be common to all members of the genus Actinobacillus. It was however found after testing a the swine-pathogenic Actinobacillus, again surprisingly in contrast with the known three RTX-genes, that this novel RTX-gene apxIV is only present in the swine-pathogen *Actinobacillus pleuropneumoniae*. It is absent in all other common swine pathogenic Actinobacillus species, and therefore it is also absent in *Actinobacillus suis*. See Example 6 and 7.

Therefore, it was surprisingly noticed that the presence of antibodies against ApxIV in the serum of a pig is a quick and unambiguous proof that the pig has been infected with *A. pleuropneumoniae*, and not with *A. suis* or any other swine-pathogen Actinobacillus species.

Thus the present invention also provides a diagnostic test based on the presence or absence of antibodies against ApxIV, and therefore a discriminating test for specifically distinguishing an infection with *A. pleuropneumoniae* from an infection with *A. suis* Such a test can e.g. be an ELISA test that comprises in separate wells the ApxI and -II toxins, present in both *A. pleuropneumoniae* and *A. suis* and the purified ApxIV toxin. Serum from *A. suis*-infected animals will react only with the wells comprising the ApxI and -II whereas *A. pleuropneumoniae*-infected animals will also react with the well comprising the purified ApxIV toxin.

EXAMPLE 1

Cloning and Analysis of the apxIV Gene of *A. pleuropneumoniae* Serotype 1

Standard molecular biological procedures (plasmid DNA isolation, restriction digestion, agarose gel electrophoresis, Southern blotting, ligation, transformation, electroporation) were, unless stated otherwise, essentially performed as described in Sambrook et al. (Molecular Cloning, A Laboratory Manual, Cold Spring Harbor, N.Y., 1989) or Ausubel et al., (Current Protocols in Molecular Biology. John Wiley & Sons, N.Y., 1987). PCR was performed essentially as described in Innis et al., (PCR protocols, A guide to Methods and Applications, Academic Press Inc., San Diego, 1990). Chromosomal DNA isolation was performed according to Pitcher et al., (Lett. Appl. Microbiol., 8;151–156, 1989). The origin of all *A. pleuropneumoniae* reference strains (serotype 1: strain 4074; serotype 2: strain S1536: serotype 3: S1421; serotype 4 M62; serotype 5a: K17; serotype 5b: L20; serotype 6: femø; serotype 7: WF83; serotype 8: 405; serotype 9: CV113261; serotype 10: 13039; serotype 11: 56153 and serotype 12: 8329) is described by Frey and Nicolet, (J. Clin. Microbiol., 28;232–236, 1990). *A. pleuropneumoniae* serotype 3 strain HVI 14 is a field isolate (i.e. one of the serotype 3 strains tested in Beck et al., J. Clin. Microbiol., 32;2749–2754, 1994). Other Actinobacillus strains used; *A. rossii*: ATCC 27072; *A. equuli*: ATCC 19392; *A. suis*: ATCC 15558. *Pasteurella haemolytica* type 1 strain ATCC 14003 was used.

*E. coli* host strains used: XL1-blue (Stratagene, La Yolla, Ca.; genotype: recA1 endA1 gyrA96 thi-1 hsdR17 supE44 relA1 lac [F' proAB lacl$^q$ZDM15Tn10 (Tet$^r$)]) and HMS174 (DE3) (AMS Biotechnology Ltd, Switzerland; genotype: F$^-$ recA ($r_{K12-}m_{K12+}$) rif$^r$ IDE3).

Figure 3:
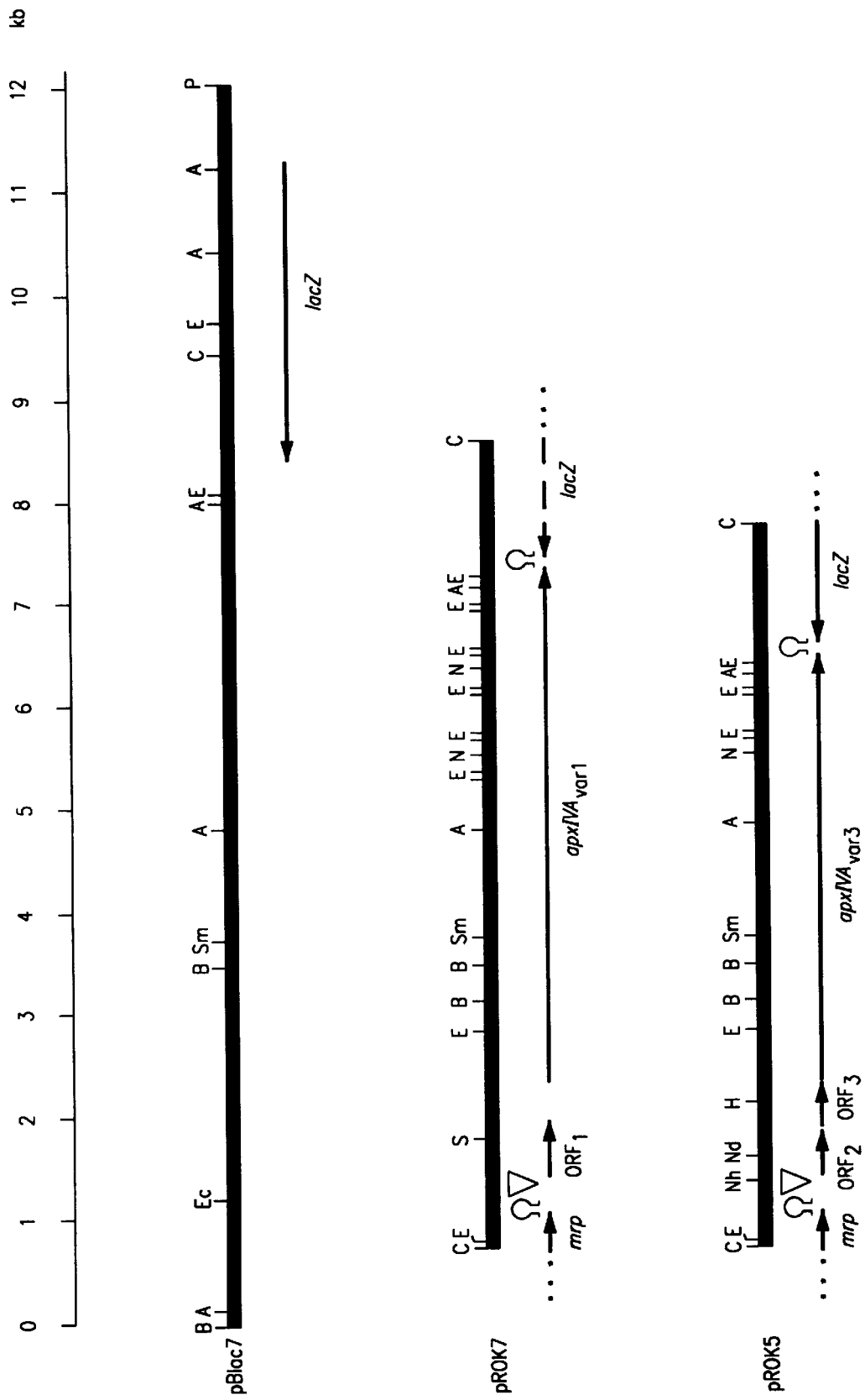

On the basis of the preliminary sequence data obtained from the thesis of T. J. Anderson (University of Guelph, 1995), two primers, designated APXIVA-1L (5'-TGGCACTGACGGTGATGA-3') and APXIVA-1R (5'-GGCCATCGACTCMCCAT-3'), were synthesised. These primers were used in a PCR amplification, with chromosomal DNA from *A. pleuropneumoniae* serotype 3 strain HV114 and serotype 1 reference strain 4074 as a template. With both strains a fragment of 442 bp was amplified. The fragment derived from the serotype 3 chromosomal DNA was labelled with Digoxigenin-11-dUTP (Boehringer Mannheim) according to the protocol of the manufacturer (this fragment was designated probe APXIVA, see FIG. 4). The labelled probe was subsequently used to hybridize a Southern blot containing ClaI digested chromosomal DNA from strain 4074. The probe hybridised with a fragment of approximately 8.0 kb. The apxIV gene from serotype 1 strain 4074 was isolated by ligating ClaI digested chromosomal DNA into ClaI digested pBluescript II SK$^-$ (Stratagene USA). *E. coli* strain XL1-blue was transformed with the ligated DNA and transformants were selected on an LB plate with 100 mg/ml of ampicillin. Clones harbouring the apxIV were selected by colony hybridisation of a nitrocellulose replica of the plate with the APXIVA probe. Thus, a plasmid designated pROK7 was isolated and shown to harbour a ClaI insert of approximately 8 kb. The first 6736 bp of the ClaI insert were sequenced (SEQID 1) and an open reading frame of 4971 nucleotides was identified encoding a protein of 1657 amino acid residues (SEQID 2) with a predicted size of approximately 186 kD. The gene was designated apxIV_var1 (see FIG. 3).

EXAMPLE 2

Cloning and Analysis of the apxIV Gene of *A. pleuropneumoniae* Serotype 3

The labelled probe APXIVA (mentioned in example 1) was used to hybridize a Southern blot containing ClaI digested chromosomal DNA from strain HV1114. The probe hybridised with a fragment of approximately 7.0 kb. The isolated chromosomal DNA from HV114 was digested with ClaI, and ligated with ClaI digested pBluescript II SK$^-$ (Stratagene USA). *E. coli* strain XL1-blue was transformed with the ligated DNA and transformants were selected on an LB plate with 100 mg/ml of ampicillin. Clones harbouring the apxIV were selected by colony hybridisation of a nitrocellulose replica of the plate with the APXIVA probe. Thus, a plasmid designated pROK5 was isolated and shown to harbour a ClaI insert of approximately 7 kb. The insert was analysed by sequence analysis (SEQID 3). An open reading frame of 4146 bp was identified encoding a protein of 1382 amino acid residues (SEQID 4), with a predicted size of approximately 154 kD. The gene was designated apxIV_var3 (see FIG. 3).

EXAMPLE 3

Expression of ApxIV var3-polyhistidine Fusion Proteins in *E. coli*

From plasmid pROK5, a deletion clone was made which contains the 3' end of the apxIV gene, starting at the BamHI site (nucleotide No. 2747 in SEQ ID No: 3) up to the ClaI site at the end of the insert downstream of the apxIV gene. This plasmid was designated pROK1. Using oligonucleotides APXIVAHIS1-L (5'-AGCCATATGGGCGATTTAAATTTCAG-3') and APXIVAHIS1-R (5'-TATGGATCCTCCGTGCTTCTGAGC-3') and DNA from plasmid pROK1 as a template, a DNA fragment of 2.1 kb was amplified (see FIG. 4) containing the region from bp 3520 to 5643 in apxIV_var3 (SEQID 3) flanked with NdeI and BamHI restriction sites at the 5' and 3' end respectively. After cloning of the NdeI/BamHI digested PCR fragment in expression vector pETHIS-1, digested with the same enzymes, a plasmid designated pJFFapxIV6/10his-1 was obtained. Plasmid pETHIS1 is a derivative of pET14b (Novagen Inc., Madison, Wiss.) where the multiple cloning site has been extended and a region encoding a histidine decamer has been inserted. Consequently, The pJFFapxIV6/10his-1 plasmid contains a translational fusion encoding a histidine hexamer, followed by amino acid residues 653 up to 1360 from SEQID 4, followed by a histidine decamer, under the control of a T7 promoter. The plasmid was transferred to *E. coli* strain HMS174(DE3) with pLysS, which contains an IPTG inducible T7 RNA polymerase gene as well as the T7 lysozyme gene for increased stability. The strain was grown in LB medium containing 25 mg/ml of chloramphenicol and 100 mg/ml of ampicillin, up to an $OD_{650}$ of 0.5, and induced with isopropyl-b-D-thiogalactopyranoside at a concentration of 10 mM. After the addition of IPTG, the cells were incubated at 37° C. for 2.5 hours, the cells were harvested by centrifugation, and fusion protein with the expected size of 80 kD was isolated in the form of inclusion bodies. The inclusion bodies were solubilized in a solution of 6M guanidine hydrochloride, 300 mM NaCl and 50 mM $NaH_2PO_4$ at pH 8.0 and the 80 kD fusion protein was further purified by Immobilised Metal Affinity Chromatography (IMAC) (Schmitt et al., Molecular Biology Reports 18;223–230, 1993) using $Ni^{2+}$ chelated columns (Qiagen AG, Basel). Pure protein was eluted from the column at pH 5.0. Pooled fractions were dialysed against a solution of 300 mM NaCl and 50 mM $NaH_2PO_4$ at pH 8.0. A rabbit was immunised with 500 mg of the polyhistidine fusion product, mixed with 1 volume of Complete Freunds Adjuvant (Difco Labs, Detroit, Mich.). A booster dose of the same amount, mixed with incomplete Freund Adjuvant was given 3 weeks later. Four weeks after the booster, the rabbit was bled and a hyperimmune serum comprising anti-ApxIV toxin antibodies, designated serum 522-409, was obtained.

EXAMPLE 4

Expression of apxIV genes in in vitro grown *A. pleuropneumoniae*

Figure 5A:
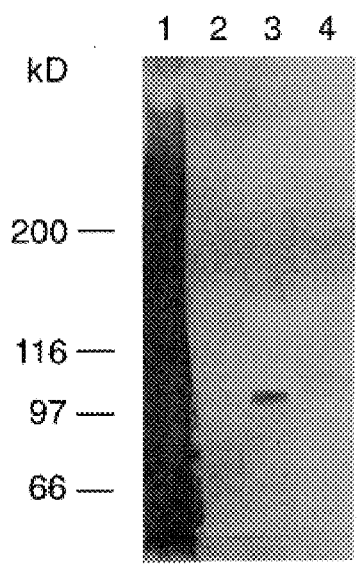
Figure 5B:
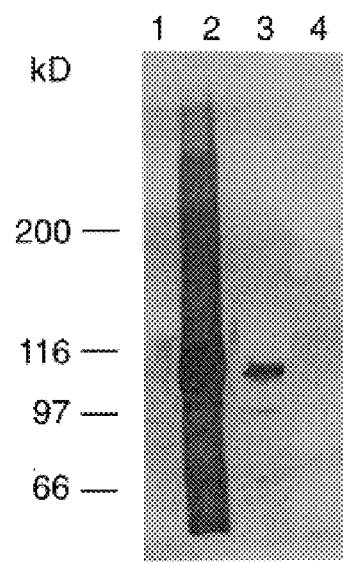
Figure 5C:
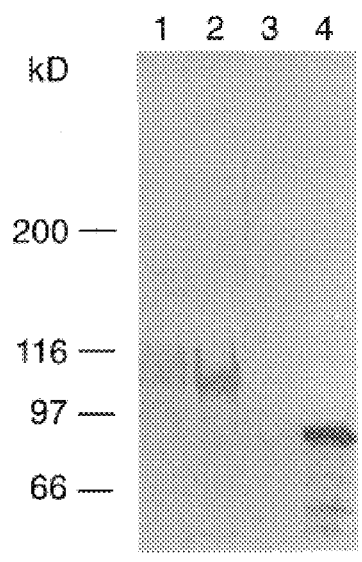

The *A. pleuropneumoniae* reference strain from serotype 1 was grown in Columbia broth supplemented with 10 mg/ml of b-NAD and harvested as described (Beck et al., J. Clin. Microbiol., 32;2749–2754, 1994). Adjacent to lanes comprising ApxIA, ApxIIA and ApxIVA-polyhistidine fusion proteins the concentrated culture supernatant was separated by polyacrylamide gel electrophoresis (Laemmli, Nature 227:680–685, 1970) and subjected to a Western blotting procedure (Towbin et al., Proc. Natl. Acad. Sci. USA 76:4350–4354, 1979). The Western blot was reacted with anti-ApxIA- and anti-ApxIIA monoclonal antibodies as described by Beck et al., (J. Clin. Microbiol., 32;2749–2754, 1994), and with anti-ApxIV serum 522-409 (see example 3). The isolated RTX toxin fraction of serotype 1 clearly contains ApxIA and ApxIIA. The presence of ApxIVA could not be demonstrated (see FIG. 5).

EXAMPLE 5

Expression of ApxIV Genes in *A. pleuropneumoniae* in vivo durinq Infection

Figure 6:
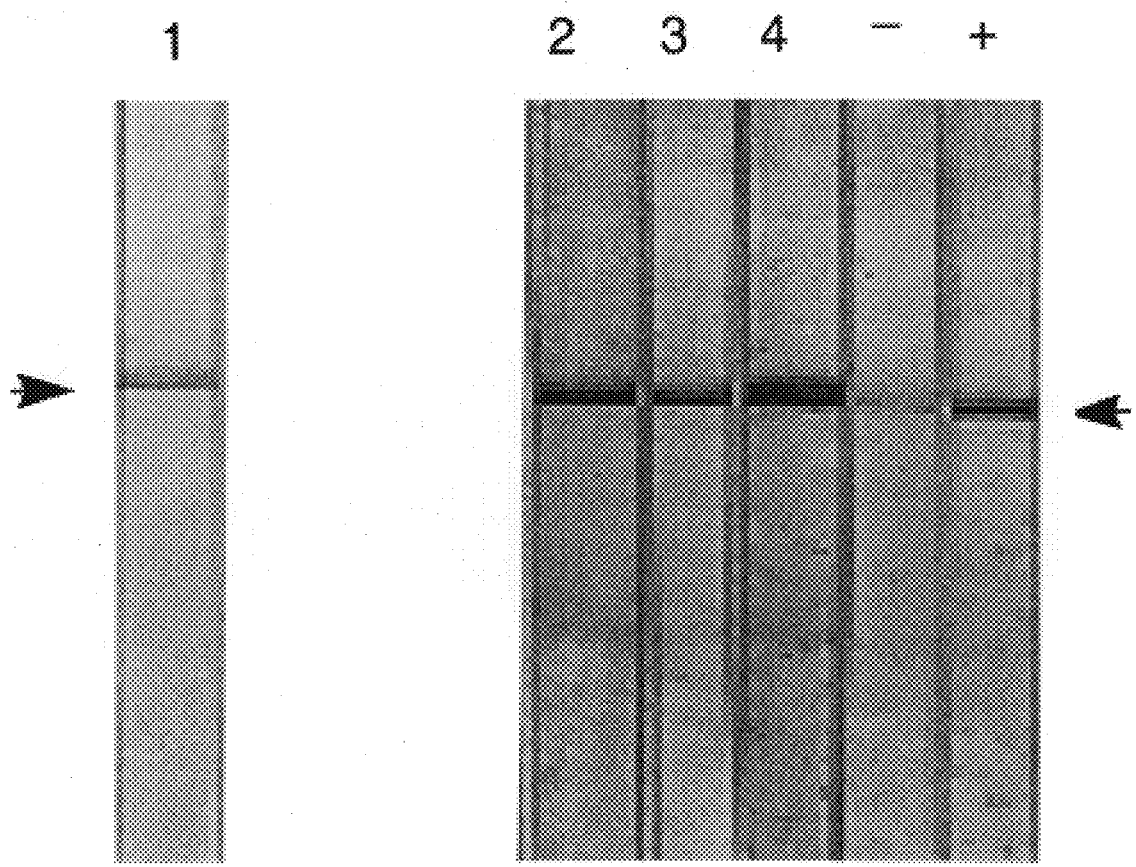

A polyacrylamide gel containing the 80 kD polyhistidine-ApxIV_var3 fusion protein (see example 3) was transferred to a nitrocellulose membrane. The membrane was divided into strips which were reacted with (100-fold dilutions of) convalescent field sera against serotype 1 or sera from a pig, experimentally infected with the serotype 1 reference strain (Frey and Nicolet, Vet. Microbiol., 28;61–73, 1991). The reaction was visualised using alkaline phosphataselabelled conjugate against rabbit IgG (Kirkegaard Perry Inc., Gaithersburg, Md.) and NBT (4-Nitrobluetetrazolium chloride) and BCIP (5-Bromo-4-chloro-3-indolyl-phosphate) colour development (see FIG. 6). The serotype 1 field sera, as well as serum from the experimentally infected pig react with the 80 kD polyhistidine-ApxIV_var3 protein. This indicates that the ApxIV protein actually is expressed, is antigenic and induces anti-ApxIV toxin antibodies during *A. pleuropneumoniae* infection in pigs.

EXAMPLE 6

Figure 4:
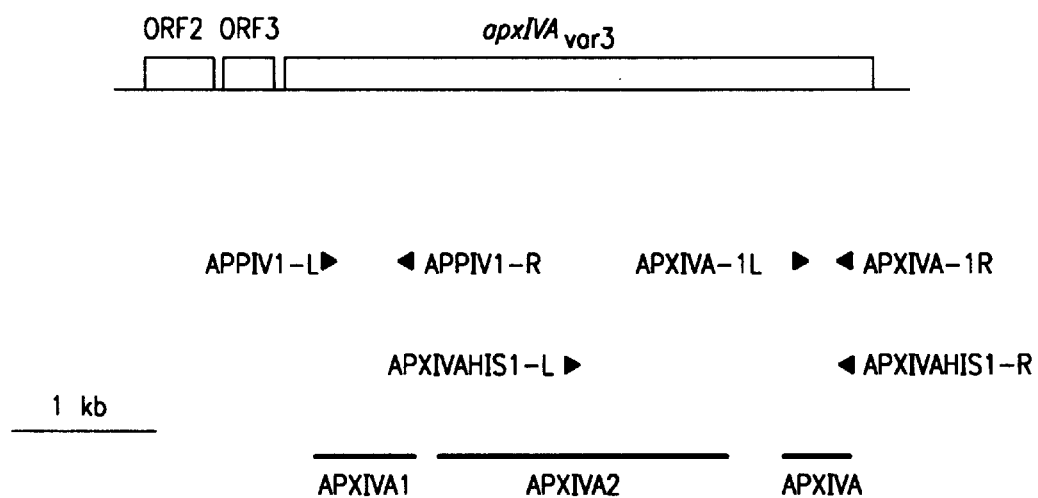
Figure 7:
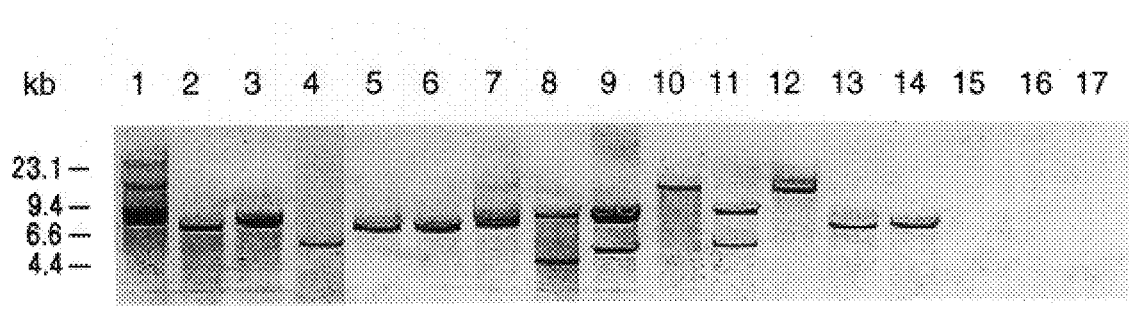

Presence of ApxIV Genes in all *A. pleuropneumoniae* serotypes and the Absence thereof in non-*pleurypneumoniae Actinobacillus*-strains using Southern Blotting To investigate the presence of the apxIV gene in the various *A.pleuropneumoniae* serotypes and related bacteria, three probes were made (see FIG. 4). Probe APXIVA is described in example 1. Probe APXIVA2 contains the 2015 bp DNA fragment between the BamHI and NruI sites. The 758 bp probe APPIVA1 was made by PCR amplification with oligos APPIV1-L (5'-GGGACAGTGGCTCMATTAG-3') and (APPIV1-R (5'-AGCTGTAAACTCCACCAACG-3'). All probes were labelled with Digoxigenin-11-dUTP (Boehringer Mannheim) according to the protocol of the manufacturer and hybridised with Southern blots containing ClaI digested chromosomal DNA of all *A. pleuropneumoniae* reference strains and the HV114 field strain, *Actinobacillus suis* (ATCC 15558), *Actinobacillus rossli* (ATCC 27072) and *Actinobacillus equuli* (ATCC 19392). All three probes react similarly (see FIG. 7 for the results with the APXIVA2 probe). All *A. pleuropneumoniae* strains react, whereas no hybridisation is observed with the *A. suis, A. equuli* and *A. rossii* strains.

EXAMPLE 7

Figure 8:
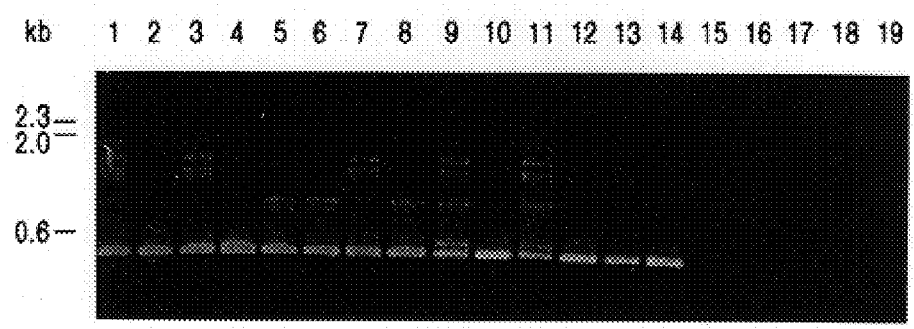

Presence of ApxIV Genes in *A. pleuropneumoniae* and related Strains using PCR Amplification With 50 ng of chromosomal DNA from the various *A. pleuropneumoniae* serotypes, other Actinobacillus species and *P. haemolytica* as templates, and primers APXIVA-1L (5'-TGGCACTGACGGTGATGA-3') and APXIVA-1R (5'-GGCCATCGACTCAACCAT-3') PCR amplification was performed. After analysis of the products on an agarose gel, products with the expected size of 442 bp were observed in all *A. pleuropneumoniae* samples, but in none of the other Actinobacillus species (FIG. 8). This indicates that in addition to the results in example 6, also PCR could be used to discriminate *A. pleuropneumoniae* from other Actinobacillus species.

EXAMPLE 8

Overexpression of ApxIV-var1 polyhistidine Fusion Protein

Starting with plasmid pROK-7 (see example 1) as a template and oligonucleotides APX4/II5-L (5'-CGCCATATGACAAAATTMCTATGCAAG) and APX4II6-R (5'-CGCGAAT TCAGCGACACAAGAGATAT) as PCR-primers, a PCR fragment was amplified. A sufficient amount of this fragment was then digested with restriction enzymes NdeI and EcoRI and cloned in expression vector pETHIS-1, digested with the same enzymes as described in Example 3. From the resulting plasmid, designated pJFFApxIVA1His1, a 206 kD polyhistidine fusion protein (MW determined in PAGE) of 1841 amino acid residues was over-expressed in *E. coli* as described in Example 3. The protein is encoded in the coding region spanning nucleic acid no. 1132 to 6546 as depicted in SEQ ID NO: 5. The amino acid sequence of the protein in given in SEQ ID NO: 6. In Westem blot this product was shown to react with specific anti-ApxIV serum 522-409 (antiserum described in example 3).

EXAMPLE 9

Protection of Mice by vaccination with ApxIV aaainst APP Challenge.

The 206 kD polyhisbdine-ApxIV fusion protein as described in Example 8 and a comparable 108 kD polyhistidine-ApxIA-fusion protein, both derived from serotype 1 reference strain 4074 genomic material, were over-expressed as described in example 3. The cell pellet of induced *E. coli* cells was resuspended into PBS buffer (1 g. cell pellet in 6 ml buffer) and sonicated on ice for two times 45 seconds on ice for lysis of the cells. After centrifugation for 20 minutes at 22.000×g at 40° C., the supernatant was discarded and the resulting pellet was washed with a solution of 3M urea (pH 6.3). The urea was removed after centrifugation for 20 minutes at 22.000×g, and the resulting pellet was solubilized in 6M GuanidiniumHCl (pH 8.0). The protein samples were standardised by specific protein content after densitometry of PAGE gels. The samples were diluted with PBS and formulated with an oil adjuvant. Three groups of 15 mice each, were intraperitoneally immunised with the ApxIV antigen (36.3 microgram), ApxIA antigen (36.3 microgram), or the adjuvant alone. The vaccines were administered in a volume of 0.4 ml. Twenty-four days after the first vaccination, each group of mice was split in two groups of 7 and 8 mice which were boosted with half the amount of antigen. The groups of 7 mice were boosted intraperitoneally in a volume of 0.2 ml and the groups of 8 mice were vaccinated intramuscularly with 0.1 ml in each hind leg. Thirteen days after the booster, the mice were challenged intraperitoneally with 1.5 $10^8$ cfu of a virulent serotype 1 strain.

EXAMPLE 10

Pore forming Capacity of ApxIV

Freshly induced *E. coli* cells expressing ApxIV were used as the source of protein for testing pore formation in artificial lipid bilayers as described by Maier et al., Infect. Immun., 64; 4415–4423(1996). The methods used for black lipid bilayer experiments have been described previously (Benz et al.; Biochim. Biophys. Acta 511: 305–319 (1978)). Membranes were formed from a 1 % solution of asolectin (soybean lecitin type IV-S from Sigma, St. Louis Mo.) in n-decane. Zero current membrane potentials were measured with a Keithley 610 C electrometer 5–10 min. after a 10-fold salt gradient was established across the membranes (Benz et al.; Biochim. Biophys. Acta 551: 238–247 (1979)). The presence of ApxIV resulted in a high frequency of pore formation in the presence of 0.5% cholesterol, with an average single channel conductance (G) of 4 nS. These results indicate that the ApxIV induces pores into artificial bilayers and is therefore toxic to eukaryotic cells and thus is a virulence factor for *A. pleuropneumoniae.*

Legend to the Figures

FIG. 1: Comparison of ApxIVAvar1 and ApxIVAvar3 (var stands for serotype). Graphic representation of the different features found in the C-terminal end. Dashed boxes represent the direct repeat regions in ApxIVA. Bold vertical bars indicate the position of glycine rich nonapeptides, and DNA polymerase family B signatures are indicated by black triangles. The amino acid sequence YSDSANSKK represents the spacer sequence in the ApxIVAvar3 gene. The sequence segment of ApxIVAvar1 which is deleted in ApxIVAvar3 is also indicated in the figure.

FIG. 2: Alignment of the amino add sequences of direct repeat 1 (A), direct repeat 2 (B) and direct repeat 3 (C) of ApxIVAvar1 and ApxIVAvar3. The copies of each of the direct repeats 1, 2 and 3 are labeled by letters to distinguish them for the sequence comparison. Variant residues are shown in bold letters.

FIG. 3: Partial restriction maps of pBLac7 (Thesis of T. J. Anderson University of Guelph, 1995), pROK7 and pROK5. The different open reading frames (ORF's) are indicated by arrows. The interrupted arrow of lacZ in pROK7 indicates partial sequencing of the gene. Potential rthoindependent transcription terminators are indicated (W). Potential transcription start sites are indicated by a triangle. Restriction sites: A=Asp700; B=BamHI; C=Clal; E=EcoRV; Ec=EcoRI; H=HindIII; N=Nrul; Nd=NdeI; Nh=Nhel; P=Pstl; S=Spel; Sm=Smal.

FIG. 4: Location of the various oligonucleotides and probes on the map of the apxIVAvar3 gene.

FIG. 5: Expression of ApxIV in in vitro cultivated serotype 1 reference strain 4074. Panel A was reacted with the anti-ApxIA monoclonal antibody, panel B with anti-ApxIIA monoclonal antibody and panel C was reacted with anti-ApxIVA serum 522-409. Lane 1 contains ApxIA-polyhistidine fusion protein, lane 2 contains ApxIIA-polyhistidine fusion protein, lane 3 contains strain 4074 concentrated culture supematant, lane 4 contains ApxIVA polyhistidine fusion protein.

FIG. 6: Immunoblot showing the reactivities of sera from pigs which were experimentally infected with the reference strain of serotype 1 (lane 1) or pig sera from serotype 1 field infections (lane 2–4) with the 80 kD polyhistidine-ApxIV fusion protein. As a positive control (+), serum 522-409 was used, as a negative control (−), polyconal rabbit serum against ApxI and ApxII (Frey et al., Infect. Immun., 57;2050–2056, 1989) was used as a 1000-fold dilution.

FIG. 7: Southern blot of Clal digested genomic DNA hybridised with probe APXIVA2. Lanes 1–13*: A. pleuropneumoniae* reference strains; 1: serotype 1; 2: serotype 2; 3: serotype 3; 4: serotype 4; 5: serotype 5a; 6: serotype 5b; 7: serotype 6; 8: serotype 7; 9: serotype 8; 10: serotype 9; 11: serotype 10; 12: serotype 11; 13: serotype 12; 14: HV114 field strain; 15*: A. suis* (ATCC 15558); 16*: A. rossii* (ATCC 27072); 17*: A. equuli* (ATCC 19392). Molecular size markers are indicated (in kilobasepairs) on the left.

FIG. 8: PCR amplification of apxIV using primers APXIVA-1L and APXIVA-1R. Lane assignments: lanes 1 to 13 contain the *A. pleuropneumoniae* reference strains from serotypes 1, 2, 3, 4, 5a, 5b, 6, 7, 8, 9,10, 11 and 12 respectively; lane 14: strain HV114; lane 15: *A. suis* ATCC 15558; lane 16: *A. rossii* ATCC 27072; lane 17: *A. equuli* ATCC 19392; lane 18: *A. lignieresii* ATCC 49236; lane 19: *P. haemolytica* type 1 ATCC 14003. Molecular size markers (in kilobasepairs) are indicated on the left.

We claim:

1. A live attenuated bacterium of the species *Actinobacillus pleuropneumoniae*, which produces no functional ApxIV toxin.

2. The live attenuated bacterium according to claim 1, wherein the gene encoding the ApxIV toxin comprises a mutation.

3. The live attenuated bacterium according to claim 2, wherein the mutation is an insertion and/or deletion.

4. The live attenuated bacterium according to claim 3, wherein the insertion comprises a heterologous gene.

5. The live attenuated bacterium according to claim 4, wherein said heterologous gene encodes one or more antigens selected from the group consisting of Porcine Reproductive Respiratory Syndrome (PRRS) virus, Pseudorabies virus, Porcine Influenza virus, Porcine Parvovirus, Transmissible Gastroenteritis virus, rotavirus, *Escherichia coli, Erysipelothrix rhusiopathiae, Pasteurella multocida, Bordetella bronchiseptica, Haemophilus parasuis* and *Streptococcus suis.*

6. The live attenuated bacterium according to claim 4, wherein said heterologous gene is functionally linked to the promoter region of the apxIV gene.

7. A live attenuated vaccine for the protection of animals against infection with a bacterium of the species *Actinobacillus pleuropneumoniae*, comprising a live attenuated bacterium according to claim 1 and a pharmaceutically acceptable carrier.

8. The vaccine according to claim 7, further comprising an adjuvant.

9. The vaccine according to claim 7, which is in freeze-dried form.

10. The vaccine according to claim 8, which is in freeze-dried form.

11. The vaccine according to claim 7, further comprising one or more antigens from pig-pathogenic microorganisms or viruses.

12. The vaccine according to claim 11, wherein said one or more antigens are from microorganisms or viruses selected from the group consisting of Porcine Reproductive Respiratory Syndrome (PRRS) virus, Pseudorabies virus, Porcine Influenza virus, Porcine Parvovirus, Transmissible Gastroenteritis virus, rotavirus, *Escherichia coli, Erysipelothrix rhusiopathiae, Pasteurella multocida, Bordetella bronchiseptica, Haemophilus parasuis* and *Streptococcus suis.*

13. A method for the protection of a susceptible animal against *Actinobacillus pleuropneumoniae* infection, comprising administering a vaccine according to claim 11 to the animal.

14. A diagnostic method for distinguishing between pigs infected with field strains of *Actinobacillus pleuropneumoniae* and pigs vaccinated with a vaccine comprising the live attenuated *Actinobacillus pleuropneumoniae* according to claim 1, or for distinguishing between pigs infected with *Actinobacillus pleuropneumoniae* and pigs infected with *A. suis*, comprising reacting sera from a pig with purified ApxIV toxin to allow for the formation of an antigen-antibody complex, and detecting said complex, whereby the detection of said complex indicates that the pig is infected with a field strain of *Actinobacillus pleuropneumoniae* and not *A. suis* and has not been vaccinated with the live attenuated bacterium.

* * * * *

```
                              SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
        (A) LENGTH: 6736 base pairs
        (B) TYPE: nucleic acid
        (C) STRANDEDNESS: double
        (D) TOPOLOGY: circular (ii) MOLECULE TYPE: DNA (genomic)

(vi) ORIGINAL SOURCE:
         (A) ORGANISM: Actinobacillus pleuropneumoniae
         (B) STRAIN: 4074 (serotype 1 reference strain)

(vii) IMMEDIATE SOURCE:
          (B) CLONE: pROK7

(ix) FEATURE:
         (A) NAME/KEY: CDS
         (B) LOCATION:1576..6549
         (D) OTHER INFORMATION:/codon_start= 1576
             /function= "RTX-toxin"
             /product= "ApxIV_var1"
             /gene= "apxIV_var1"
             /number= 1

(xi) SEQUENCE DESCRIPTION: SEQ ID NO: 1:

ATCGATATGC CGCCGGGTAC GGGCGATATC CAACTTACTC TTTCGCAACA AATTCCGGTT      60

ACCGGTGCGG TGGTGGTAAC CACTCCGCAA GATATTGCGT TATTAGATGC GGTGAAAGGT     120

ATTTCAATGT TCCAAAAAGT GTCGGTACCG GTCTTAGGTA TCATTGAAAA TATGAGCGTA     180

CATATCTGCC AAAATTGCGG TCACCACGAA GATATTTTCG GCACCGGCGG TGCGGAGAAA     240

GTGGCGAAGA AATACGGTAC TAAAGTATTA GGACAAATGC CGTTGCATAT TCGCTTACGT     300

CAAGATTTGG ATGCCGGCAC ACCGACCGTC GTTGCGGCAC CGGAACACGA AACCAGCCGA     360

GCCTATATTG AATTAGCGGC AAAAGTCGCT TCGGAATTAT ACTGGCAAGG TTCGGTTATC     420

CCGTCTGAAA TTATGATTCG TGAAGTAAAA TAAGTTTTAA TAACCACGAA AACACAAAGA     480

ACACAAGCGG TAGAATTTGC AGAAAAATTT GCAAATCCTA CCGCTTTTTT ATTAGTACGA     540

TTCGCTGTTG GACTGCTATT TGATTTGGTT TGTCAGGATA TTATGTTATT GTAATGAAAT     600

GTTAGTGAAT TATTTTATT AATTTGAAAG GAAACAAAAT GAAAATAAAA AAACGTTACA     660

TTGCGCTGTT GGTCTTAGGT GTCGTTATCA GCTATGCCTG GTATCAAAAT TATCAATGGG     720

AACAGCTGAT GTTAAGCGGT TATTGTGAAA AGGACGGAAG TTATTTTGAT GATAGGCATA     780

CGAAGCAAGA ACTGATTGAT AGGGCAATTA ACTATATGCT GGAGCATCAA TCTAAAAAAA     840

CATACGATGC TTATACTGAT GAACCTTTAG AAATAAAACC ATATTTAACA ATAGAGGAAT     900

TTAAAAAACT CAATCCAAAT TGTTGTGAAA TTACCTCATG GCCAGCAGAT GCAGTTCCAC     960

AAGATTGGGA TGTTCGTGTG GAAGGTAAGG CATATAGGTA TGTAATCGTA AAATATTTAA    1020

GAACCTTAGC AAATAGAGAA CCTGAACGAT GGGAAACTAG TATTGTTTTT GATAATTGCG    1080

GCAATCCTAA AAGAGCAAGC TACTTATATT ATTTAAAGAG AGAAATTTAT TATGACAAAA    1140
```

-continued

```
TTAACTATGC AAGATGTGAC CAATTTATAT TTATATAAAA CGAAAACTCT ACCTAAAGAT    1200

AGATTGGATG ATTCACTTAT TTCTGAAATA GGAAAAGGAG ATGATGATAT TGATAGAAAA    1260

GAATTTATGG TGGGGCCGGG ACGTTTTGTG ACCGCTGATA ACTTTAGCGT TGTAAGAGAT    1320

TTTTTTAATG CTGGGAAATC ACGCATTATT GCGCCGCAAG TCCCGCCTAT TCGTTCACAG    1380

CAGGAAAAAA TCTTGGTCGG TTTAAAACCG GGCAAATATT CCAAAGCGCA GATATTGGAA    1440

ATGCTGGGTT ATACGAAAGG CGGAGAAGTG GTAAATGGCA TGTTTGCCGG TGAAGTCCAG    1500

ACATTAGGCT TTTATGACGA TGGCAAAGGG GATTTACTCG AACGCGCCTA TATCTGGAAT    1560

ACCACAGGAT TTAAA ATG AGC GAC AAT GCC TTT TTT GTT ATA GAA GAA TCA    1611
               Met Ser Asp Asn Ala Phe Phe Val Ile Glu Glu Ser
                1              5                  10

GGC AAA CGC TAT ATT GAA AAC TTT GGT ATT GAA CCT CTT GGT AAG CAA    1659
Gly Lys Arg Tyr Ile Glu Asn Phe Gly Ile Glu Pro Leu Gly Lys Gln
         15              20                  25

GAA GAT TTT GAT TTT GTC GGC GGC TTT TGG TCT AAC TTA GTG AAT CGT    1707
Glu Asp Phe Asp Phe Val Gly Gly Phe Trp Ser Asn Leu Val Asn Arg
     30              35                  40

GGT TTG GAA AGT ATT ATC GAC CCA TCC GGT ATC GGT GGA ACG GTA AAC    1755
Gly Leu Glu Ser Ile Ile Asp Pro Ser Gly Ile Gly Gly Thr Val Asn
 45              50                  55                      60

CTT AAC TTT ACC GGC GAG GTG GAA ACC TAC ACG TTA GAC GAA ACA AGG    1803
Leu Asn Phe Thr Gly Glu Val Glu Thr Tyr Thr Leu Asp Glu Thr Arg
             65                  70                  75

TTT AAA GCG GAA GCG GCG AAG AAA AGC CAT TGG AGT TTA GTG AAT GCG    1851
Phe Lys Ala Glu Ala Ala Lys Lys Ser His Trp Ser Leu Val Asn Ala
             80                  85                  90

GCG AAA GTA TAC GGC GGT TTA GAC CAA ATT ATT AAA AAA CTA TGG GAC    1899
Ala Lys Val Tyr Gly Gly Leu Asp Gln Ile Ile Lys Lys Leu Trp Asp
             95                 100                 105

AGT GGC TCA ATT AAG CAT TTA TAT CAA GAT AAA GAT ACG GGC AAA TTA    1947
Ser Gly Ser Ile Lys His Leu Tyr Gln Asp Lys Asp Thr Gly Lys Leu
110                 115                 120

AAA CCG ATT ATT TAC GGC ACG GCC GGC AAC GAC AGT AAG ATT GAA GGC    1995
Lys Pro Ile Ile Tyr Gly Thr Ala Gly Asn Asp Ser Lys Ile Glu Gly
125                 130                 135                 140

ACT AAA ATC ACC CGT AGG ATT GCG GGT AAA GAA GTT ACG CTT GAT ATT    2043
Thr Lys Ile Thr Arg Arg Ile Ala Gly Lys Glu Val Thr Leu Asp Ile
                145                 150                 155

GCC AAT CAG AAA ATT GAA AAA GGC GTG TTA GAG AAA TTG GGG CTG TCT    2091
Ala Asn Gln Lys Ile Glu Lys Gly Val Leu Glu Lys Leu Gly Leu Ser
                160                 165                 170

GTT AGT GGT TCG GAT ATC ATT AAA TTG TTG TTT GGA GCA TTG ACT CCA    2139
Val Ser Gly Ser Asp Ile Ile Lys Leu Leu Phe Gly Ala Leu Thr Pro
            175                 180                 185

ACT TTA AAT AGA ATG TTG CTA TCA CAA CTT ATC CAG TCT TTT TCC GAT    2187
Thr Leu Asn Arg Met Leu Leu Ser Gln Leu Ile Gln Ser Phe Ser Asp
        190                 195                 200

AGC TTG GCT AAA CTT GAT AAT CCC TTA GCC CCT TAC ACT AAA AAT GGC    2235
Ser Leu Ala Lys Leu Asp Asn Pro Leu Ala Pro Tyr Thr Lys Asn Gly
205                 210                 215                 220

GTG GTT TAT GTC ACC GGC AAA GGG AAT GAT GTG CTT AAA GGA ACT GAA    2283
Val Val Tyr Val Thr Gly Lys Gly Asn Asp Val Leu Lys Gly Thr Glu
                225                 230                 235

CAT GAG GAT TTG TTT CTC GGT GGT GAG GGG AAT GAT ACT TAT TAT GCG    2331
His Glu Asp Leu Phe Leu Gly Gly Glu Gly Asn Asp Thr Tyr Tyr Ala
            240                 245                 250

AGA GTA GGC GAT ACA ATT GAA GAC GCC GAC GGC AAA GGT AAA GTC TAT    2379
```

```
Arg Val Gly Asp Thr Ile Glu Asp Ala Asp Gly Lys Gly Lys Val Tyr
        255                 260                 265
TTT GTG AGA GAA AAA GGG GTA CCT AAG GCG GAT CCT AAG CGG GTA GAG   2427
Phe Val Arg Glu Lys Gly Val Pro Lys Ala Asp Pro Lys Arg Val Glu
        270                 275                 280
TTT AGC GAG TAC ATA ACG AAA GAA GAA ATA AAA GAG GTT GAA AAG GGG   2475
Phe Ser Glu Tyr Ile Thr Lys Glu Glu Ile Lys Glu Val Glu Lys Gly
285                 290                 295                 300
TTA TTA ACT TAC GCA GTT TTA GAA AAT TAT AAT TGG GAA GAG AAA ACG   2523
Leu Leu Thr Tyr Ala Val Leu Glu Asn Tyr Asn Trp Glu Glu Lys Thr
                305                 310                 315
GCG ACT TTC GCT CAT GCG ACT ATG CTT AAT GAG CTT TTT ACT GAT TAT   2571
Ala Thr Phe Ala His Ala Thr Met Leu Asn Glu Leu Phe Thr Asp Tyr
                320                 325                 330
ACT AAT TAT CGT TAT GAA GTT AAA GGA CTA AAA TTG CCC GCC GTT AAA   2619
Thr Asn Tyr Arg Tyr Glu Val Lys Gly Leu Lys Leu Pro Ala Val Lys
                335                 340                 345
AAG TTA AAA AGT CCG TTG GTG GAG TTT ACA GCT GAT TTA TTA ACT GTT   2667
Lys Leu Lys Ser Pro Leu Val Glu Phe Thr Ala Asp Leu Leu Thr Val
350                 355                 360
ACG CCT ATT GAC GAA AAC GGA AAA GCA CTT AGC GAA AAA AGT ATT ACG   2715
Thr Pro Ile Asp Glu Asn Gly Lys Ala Leu Ser Glu Lys Ser Ile Thr
365                 370                 375                 380
GTT AAA AAT TTT AAA AAT GGT GAT TTA GGA ATA AGG TTG TTG GAT CCT   2763
Val Lys Asn Phe Lys Asn Gly Asp Leu Gly Ile Arg Leu Leu Asp Pro
                385                 390                 395
AAT AGC TAT TAT TAT TTC CTT GAA GGC CAA GAT ACG GGT TTT TAT GGT   2811
Asn Ser Tyr Tyr Tyr Phe Leu Glu Gly Gln Asp Thr Gly Phe Tyr Gly
                400                 405                 410
CCT GCT TTT TAT ATT GAA CGA AAA AAC GGT GGC GGC GCT AAA AAT AAC   2859
Pro Ala Phe Tyr Ile Glu Arg Lys Asn Gly Gly Gly Ala Lys Asn Asn
                415                 420                 425
TCG TCG GGA GCA GGA AAT AGC AAA GAT TGG GGC GGG AAC GGG CAT GGA   2907
Ser Ser Gly Ala Gly Asn Ser Lys Asp Trp Gly Gly Asn Gly His Gly
                430                 435                 440
AAT CAC CGA AAT AAT GCC TCC GAC CTG AAT AAA CCG GAC GGA AAT AAT   2955
Asn His Arg Asn Asn Ala Ser Asp Leu Asn Lys Pro Asp Gly Asn Asn
445                 450                 455                 460
GGG AAT AAC CAA AAT AAC GGA AGC AAT CAA GAT AAT CAT AGC GAT GTG   3003
Gly Asn Asn Gln Asn Asn Gly Ser Asn Gln Asp Asn His Ser Asp Val
                465                 470                 475
AAT GCG CCA AAT AAC CCG GGA CGT AAC TAT GAT ATT TAC GAT CCT TTA   3051
Asn Ala Pro Asn Asn Pro Gly Arg Asn Tyr Asp Ile Tyr Asp Pro Leu
                480                 485                 490
GCT TTA GAT TTA GAT GGA GAT GGG CTT GAA ACC GTG TCG ATG AAC GGG   3099
Ala Leu Asp Leu Asp Gly Asp Gly Leu Glu Thr Val Ser Met Asn Gly
                495                 500                 505
CGA CAA GGC GCG TTA TTC GAT CAT GAA GGA AAA GGT ATT CGT ACC GCA   3147
Arg Gln Gly Ala Leu Phe Asp His Glu Gly Lys Gly Ile Arg Thr Ala
        510                 515                 520
ACG GGC TGG CTC GCT GCG GAT GAC GGT TTT TTA GTG TTA GAT CGT AAC   3195
Thr Gly Trp Leu Ala Ala Asp Asp Gly Phe Leu Val Leu Asp Arg Asn
525                 530                 535                 540
CAA GAC GGC ATT ATT AAT GAT ATA AGC GAG TTA TTT AGT AAT AAA AAT   3243
Gln Asp Gly Ile Ile Asn Asp Ile Ser Glu Leu Phe Ser Asn Lys Asn
                545                 550                 555
CAA CTT TCC GAC GGC AGT ATT TCT GCA CAC GGT TTT GCG ACA TTA GCC   3291
Gln Leu Ser Asp Gly Ser Ile Ser Ala His Gly Phe Ala Thr Leu Ala
                560                 565                 570
GAT TTG GAT ACA AAC CAA GAT CAG CGT ATC GAC CAA AAT GAT AAG CTG   3339
```

-continued

```
                Asp Leu Asp Thr Asn Gln Asp Gln Arg Ile Asp Gln Asn Asp Lys Leu
                        575                 580                 585

TTT TCT AAA CTC CAA ATT TGG CGG GAT TTA AAT CAA AAC GGT TTT AGT                 3387
Phe Ser Lys Leu Gln Ile Trp Arg Asp Leu Asn Gln Asn Gly Phe Ser
        590                 595                 600

GAA GCG AAT GAG CTG TTT AGC TTA GAA AGT TTG AAT ATT AAA TCT TTA                 3435
Glu Ala Asn Glu Leu Phe Ser Leu Glu Ser Leu Asn Ile Lys Ser Leu
605                 610                 615                 620

CAT ACC GCC TAT GAA GAG CGT AAT GAT TTT CTA GCG GGC AAT AAT ATC                 3483
His Thr Ala Tyr Glu Glu Arg Asn Asp Phe Leu Ala Gly Asn Asn Ile
                625                 630                 635

CTT GCT CAG CTT GGG AAG TAT GAA AAA ACG GAC GGT ACT TTT GCA CAA                 3531
Leu Ala Gln Leu Gly Lys Tyr Glu Lys Thr Asp Gly Thr Phe Ala Gln
        640                 645                 650

ATG GGC GAT TTA AAT TTC AGT TTT AAC CCG TTT TAT AGC CGA TTT ACC                 3579
Met Gly Asp Leu Asn Phe Ser Phe Asn Pro Phe Tyr Ser Arg Phe Thr
                655                 660                 665

GAA GCG TTA AAT TTA ACC GAG CAA CAA CGT CGC ACA ATT AAT CTA ACC                 3627
Glu Ala Leu Asn Leu Thr Glu Gln Gln Arg Arg Thr Ile Asn Leu Thr
670                 675                 680

GGC ACC GGT CGG GTT CGG GAT TTG CGT GAA GCC GCC GCA CTT TCT GAG                 3675
Gly Thr Gly Arg Val Arg Asp Leu Arg Glu Ala Ala Ala Leu Ser Glu
685                 690                 695                 700

GAG TTG GCT GCT TTA TTA CAA CAG TAC ACT AAG GCC TCC GAT TTT CAG                 3723
Glu Leu Ala Ala Leu Leu Gln Gln Tyr Thr Lys Ala Ser Asp Phe Gln
                705                 710                 715

GCA CAA CGA GAA TTA TTG CCT GCC ATT TTA GAT AAA TGG GCG GCA ACG                 3771
Ala Gln Arg Glu Leu Leu Pro Ala Ile Leu Asp Lys Trp Ala Ala Thr
        720                 725                 730

GAT TTA CAG TAT CAA CAT TAT GAT AAA ACA TTA CTT AAA ACG GTA GAA                 3819
Asp Leu Gln Tyr Gln His Tyr Asp Lys Thr Leu Leu Lys Thr Val Glu
                735                 740                 745

AGT ACC GAT AGT AGT GCT TCT GTC GTT AGA GTC ACG CCT TCT CAA TTA                 3867
Ser Thr Asp Ser Ser Ala Ser Val Val Arg Val Thr Pro Ser Gln Leu
750                 755                 760

AGT AGT ATA CGC AAT GCA AAG CAT GAT CCT ACC GTT ATG CAA AAC TTT                 3915
Ser Ser Ile Arg Asn Ala Lys His Asp Pro Thr Val Met Gln Asn Phe
765                 770                 775                 780

GAA CAG AGT AAG GCA AAA ATT GCG ACT TTA AAT TCG CTC TAC GGG TTA                 3963
Glu Gln Ser Lys Ala Lys Ile Ala Thr Leu Asn Ser Leu Tyr Gly Leu
                785                 790                 795

AAT ATC GAT CAA CTT TAT TAC ACG ACG GAT AAA GAC ATT CGC TAT ATT                 4011
Asn Ile Asp Gln Leu Tyr Tyr Thr Thr Asp Lys Asp Ile Arg Tyr Ile
        800                 805                 810

ACT GAT AAA GTG AAT AAT ATG TAT CAA ACA ACC GTA GAA CTT GCC TAC                 4059
Thr Asp Lys Val Asn Asn Met Tyr Gln Thr Thr Val Glu Leu Ala Tyr
                815                 820                 825

CGT TCT TTA CTT TTA CAA ACG CGT TTG AAG AAA TAT GTT TAT AGC GTT                 4107
Arg Ser Leu Leu Leu Gln Thr Arg Leu Lys Lys Tyr Val Tyr Ser Val
830                 835                 840

AAT GCG AAA CAA TTC GAA GGG AAA TGG GTA ACC GAT TAT TCT CGT ACT                 4155
Asn Ala Lys Gln Phe Glu Gly Lys Trp Val Thr Asp Tyr Ser Arg Thr
845                 850                 855                 860

GAA GCC TTA TTT AAC TCT ACT TTT AAA CAA TCG CCT GAA AAT GCA TTA                 4203
Glu Ala Leu Phe Asn Ser Thr Phe Lys Gln Ser Pro Glu Asn Ala Leu
                865                 870                 875

TAT GAT TTA AGC GAA TAC CTT TCT TTC TTT AAC GAT CCT ACG GAA TGG                 4251
Tyr Asp Leu Ser Glu Tyr Leu Ser Phe Phe Asn Asp Pro Thr Glu Trp
        880                 885                 890

AAA GAA GGG CTA TTA CTG TTA AGC CGT TAT ATA GAT TAT GCT AAA GCA                 4299
Lys Glu Gly Leu Leu Leu Leu Ser Arg Tyr Ile Asp Tyr Ala Lys Ala
```

-continued

```
                Lys Glu Gly Leu Leu Leu Leu Ser Arg Tyr Ile Asp Tyr Ala Lys Ala
                            895                 900                 905

CAA GGA TTT TAT GAA AAC TGG GCG GCT ACT TCT AAC TTA ACT ATT GCC            4347
Gln Gly Phe Tyr Glu Asn Trp Ala Ala Thr Ser Asn Leu Thr Ile Ala
            910                 915                 920

CGT TTA AGA GAG GCT GGA GTA ATT TTT GCA GAA TCG ACG GAT TTA AAA            4395
Arg Leu Arg Glu Ala Gly Val Ile Phe Ala Glu Ser Thr Asp Leu Lys
925                 930                 935                 940

GGC GAT GAA AAA AAT AAT ATT TTG TTA GGT AGC CAA AAA GAT AAT AAC            4443
Gly Asp Glu Lys Asn Asn Ile Leu Leu Gly Ser Gln Lys Asp Asn Asn
                945                 950                 955

TTA TCG GGT AGT GCA GGT GAT GAT CTA CTT ATC GGC GGA GAG GGT AAT            4491
Leu Ser Gly Ser Ala Gly Asp Asp Leu Leu Ile Gly Gly Glu Gly Asn
            960                 965                 970

GAT ACG TTA AAA GGC AGC TAC GGT GCA GAC ACC TAT ATC TTT AGC AAA            4539
Asp Thr Leu Lys Gly Ser Tyr Gly Ala Asp Thr Tyr Ile Phe Ser Lys
            975                 980                 985

GGA CAC GGA CAG GAT ATC GTT TAT GAA GAT ACC AAT AAT GAT AAC CGC            4587
Gly His Gly Gln Asp Ile Val Tyr Glu Asp Thr Asn Asn Asp Asn Arg
990                 995                 1000

GCA AGA GAT ATC GAC ACC TTA AAA TTT ACC GAT GTG AAT TAT GCG GAA            4635
Ala Arg Asp Ile Asp Thr Leu Lys Phe Thr Asp Val Asn Tyr Ala Glu
1005                1010                1015                1020

GTG AAG TTT CGA CGA GTA GAT AAT GAC TTA ATG TTA TTC GGT TAT CAT            4683
Val Lys Phe Arg Arg Val Asp Asn Asp Leu Met Leu Phe Gly Tyr His
            1025                1030                1035

GAT ACG GAT TCG GTC ACG GTA AAA TCC TTC TAC AGC CAT GTA GAT TAT            4731
Asp Thr Asp Ser Val Thr Val Lys Ser Phe Tyr Ser His Val Asp Tyr
            1040                1045                1050

CAA TTT GAC AAA TTG GAG TTT GCT GAC CGC AGT ATA ACT CGC GAT GAA            4779
Gln Phe Asp Lys Leu Glu Phe Ala Asp Arg Ser Ile Thr Arg Asp Glu
            1055                1060                1065

CTG ATT AAA GCA GGG CTT CAT CTA TAC GGC ACC GAT GGC AAT GAT GAT            4827
Leu Ile Lys Ala Gly Leu His Leu Tyr Gly Thr Asp Gly Asn Asp Asp
            1070                1075                1080

ATA AAG GAT CAT GCG GAT TGG GAC AGC ATT TTG GAA GGC GGC AAA GGC            4875
Ile Lys Asp His Ala Asp Trp Asp Ser Ile Leu Glu Gly Gly Lys Gly
1085                1090                1095                1100

AAC GAT ATT CTA AGA GGT GGC TAC GGT GCG GAC ACC TAT ATC TTT AGC            4923
Asn Asp Ile Leu Arg Gly Gly Tyr Gly Ala Asp Thr Tyr Ile Phe Ser
                1105                1110                1115

AAA GGA CAC GGA CAG GAT ATC GTT TAT GAA GAT ACC AAT AAT GAT AAC            4971
Lys Gly His Gly Gln Asp Ile Val Tyr Glu Asp Thr Asn Asn Asp Asn
            1120                1125                1130

CGC GCA AGA GAT ATC GAC ACC TTA AAA TTT ACT GAT GTG AAT TAT GCG            5019
Arg Ala Arg Asp Ile Asp Thr Leu Lys Phe Thr Asp Val Asn Tyr Ala
            1135                1140                1145

GAA GTG AAA TTC CGA CGA GTA GAT AAT GAC TTA ATG TTA TTC GGT TAT            5067
Glu Val Lys Phe Arg Arg Val Asp Asn Asp Leu Met Leu Phe Gly Tyr
            1150                1155                1160

CAT GAT ACG GAT TCG GTC ACG ATA AAA TCC TTC TAC AAC CAT GTA GAT            5115
His Asp Thr Asp Ser Val Thr Ile Lys Ser Phe Tyr Asn His Val Asp
1165                1170                1175                1180

TAT CAA TTT GAC AAA TTG GAA TTT GCT GAC CGC AGT ATA ACT CGT GAT            5163
Tyr Gln Phe Asp Lys Leu Glu Phe Ala Asp Arg Ser Ile Thr Arg Asp
                1185                1190                1195

GAA CTA GGT AAA CAA GGT ATG GCA TTA TTT GGC ACT GAC GGT GAT GAT            5211
Glu Leu Gly Lys Gln Gly Met Ala Leu Phe Gly Thr Asp Gly Asp Asp
            1200                1205                1210

AAT ATC AAC GAC TGG GGA CGT AAC TCG GTG ATT GAT GCC GGT GCG GGT            5259
```

-continued

| | | |
|---|---|---|
| Asn Ile Asn Asp Trp Gly Arg Asn Ser Val Ile Asp Ala Gly Ala Gly<br>1215                                  1220                                1225 | |

```
AAT GAT ACG GTT AAT GGC GGT AAT GGC GAT GAC ACC CTC ATC GGC GGC        5307
Asn Asp Thr Val Asn Gly Gly Asn Gly Asp Asp Thr Leu Ile Gly Gly
        1230                1235                1240

AAA GGT AAT GAT ATT CTA AGA GGT GGC TAC GGT GCG GAC ACC TAT ATC        5355
Lys Gly Asn Asp Ile Leu Arg Gly Gly Tyr Gly Ala Asp Thr Tyr Ile
1245                1250                1255                1260

TTT AGC AAA GGA CAC GGA CAG GAT ATC GTT TAT GAA GAT ACC AAT AAT        5403
Phe Ser Lys Gly His Gly Gln Asp Ile Val Tyr Glu Asp Thr Asn Asn
            1265                1270                1275

GAT AAC CGC GCA AGA GAT ATC GAC ACC TTA AAA TTT ACC GAT GTG AAT        5451
Asp Asn Arg Ala Arg Asp Ile Asp Thr Leu Lys Phe Thr Asp Val Asn
        1280                1285                1290

TAT GCG GAA GTG AAA TTC CGA CGA GTA GAT AAT GAC TTA ATG TTA TTC        5499
Tyr Ala Glu Val Lys Phe Arg Arg Val Asp Asn Asp Leu Met Leu Phe
    1295                1300                1305

GGT TAT CAT GAT ACG GAT TCG GTC ACG GTA AAA TCC TTC TAC AGC CAT        5547
Gly Tyr His Asp Thr Asp Ser Val Thr Val Lys Ser Phe Tyr Ser His
1310                1315                1320

GTA GAT TAT CAA TTT GAC AAA TTG GAG TTT GCT GAC CGC AGT ATA ACT        5595
Val Asp Tyr Gln Phe Asp Lys Leu Glu Phe Ala Asp Arg Ser Ile Thr
1325                1330                1335                1340

CGC GAT GAA CTG ATT AAA GCA GGG CTT CAT CTA TAC GGC ACC GAT GGC        5643
Arg Asp Glu Leu Ile Lys Ala Gly Leu His Leu Tyr Gly Thr Asp Gly
            1345                1350                1355

AAT GAT GAT ATA AAG GAT CAT GCG GAT TGG GAC AGC ATT TTG GAA GGC        5691
Asn Asp Asp Ile Lys Asp His Ala Asp Trp Asp Ser Ile Leu Glu Gly
        1360                1365                1370

GGC AAA GGC AAC GAT ATT CTA AGA GGT GGC TAC GGT GCG GAC ACC TAT        5739
Gly Lys Gly Asn Asp Ile Leu Arg Gly Gly Tyr Gly Ala Asp Thr Tyr
    1375                1380                1385

ATC TTT AGC AAA GGA CAC GGA CAG GAT ATC GTT TAT GAA GAT ACC AAT        5787
Ile Phe Ser Lys Gly His Gly Gln Asp Ile Val Tyr Glu Asp Thr Asn
1390                1395                1400

AAT GAT AAC CGA GCA AGA GAT ATC GAC ACC TTA AAA TTT ACT GAT GTG        5835
Asn Asp Asn Arg Ala Arg Asp Ile Asp Thr Leu Lys Phe Thr Asp Val
1405                1410                1415                1420

AAT TAT GCG GAA GTG AAA TTC CGA CGA GTA GAT AAT GAC TTA ATG TTA        5883
Asn Tyr Ala Glu Val Lys Phe Arg Arg Val Asp Asn Asp Leu Met Leu
            1425                1430                1435

TTC GGT TAT CAT GAT ACG GAT TCG GTC ACG ATA AAA TCC TTC TAC AAC        5931
Phe Gly Tyr His Asp Thr Asp Ser Val Thr Ile Lys Ser Phe Tyr Asn
        1440                1445                1450

CAT GTA GAT TAT CAA TTT GAC AAA TTG GAA TTT GCT GAC CGC AGT ATA        5979
His Val Asp Tyr Gln Phe Asp Lys Leu Glu Phe Ala Asp Arg Ser Ile
    1455                1460                1465

ACT CGT GAT GAA CTA GGT AAA CAA GGT ATG GCA TTA TTT GGC ACT GAC        6027
Thr Arg Asp Glu Leu Gly Lys Gln Gly Met Ala Leu Phe Gly Thr Asp
1470                1475                1480

GGT GAT GAT AAT ATC AAC GAC TGG GGA CGT AAC TCG GTG ATT GAT GCC        6075
Gly Asp Asp Asn Ile Asn Asp Trp Gly Arg Asn Ser Val Ile Asp Ala
1485                1490                1495                1500

GGT GCG GGT AAT GAT ACG GTT AAT GGC GGT AAT GGC GAT GAC ACC CTC        6123
Gly Ala Gly Asn Asp Thr Val Asn Gly Gly Asn Gly Asp Asp Thr Leu
            1505                1510                1515

ATC GGC GGC AAA GGT AAT GAT ATT CTA AGA GGT GGC TAC GGT GCG GAC        6171
Ile Gly Gly Lys Gly Asn Asp Ile Leu Arg Gly Gly Tyr Gly Ala Asp
        1520                1525                1530

ACC TAT ATC TTT AGC AAA GGA CAC GGA CAG GAT ATC GTT TAT GAA GAT        6219
Thr Tyr Ile Phe Ser Lys Gly His Gly Gln Asp Ile Val Tyr Glu Asp
```

```
                Thr Tyr Ile Phe Ser Lys Gly His Gly Gln Asp Ile Val Tyr Glu Asp
                        1535                1540                1545

ACC AAT AAT GAT AAC CGC GCA AGA GAT ATC GAC ACC TTA AAA TTT ACT                 6267
Thr Asn Asn Asp Asn Arg Ala Arg Asp Ile Asp Thr Leu Lys Phe Thr
        1550                1555                1560

GAT ATT AAT TTA TCC GAA CTT TGG TTT AGC CGA GAA AAT AAC GAT TTG                 6315
Asp Ile Asn Leu Ser Glu Leu Trp Phe Ser Arg Glu Asn Asn Asp Leu
1565                1570                1575                1580

ATT ATT AAA TCA TTA TTA AGT GAG GAT AAA GTC ACG GTT CAA AAT TGG                 6363
Ile Ile Lys Ser Leu Leu Ser Glu Asp Lys Val Thr Val Gln Asn Trp
                1585                1590                1595

TAT TCA CAC CAA GAT CAT AAA ATA GAA AAT ATT CGT TTA TCG AAT GAG                 6411
Tyr Ser His Gln Asp His Lys Ile Glu Asn Ile Arg Leu Ser Asn Glu
        1600                1605                1610

CAA ACG TTG GTG AGC ACT CAG GTG GAG AAG ATG GTT GAG TCG ATG GCC                 6459
Gln Thr Leu Val Ser Thr Gln Val Glu Lys Met Val Glu Ser Met Ala
    1615                1620                1625

GGC TTT GCT CAG AAG CAC GGA GGA GAG ATA TCT CTT GTG TCG CTT GAA                 6507
Gly Phe Ala Gln Lys His Gly Gly Glu Ile Ser Leu Val Ser Leu Glu
1630                1635                1640

GAG GTA AAA CAA TAT ATC AAT AGC TTA ACA GCT GCT TTA TAA                         6549
Glu Val Lys Gln Tyr Ile Asn Ser Leu Thr Ala Ala Leu   *
1645                1650                1655

CATACGAAAG AAATCGGCAC AGTTTTTTTG AACTGTGCCG ATTTGATTTT AGTGTAAGAA              6609

TATAGCCTGA TTTTAAGAAA TTTACTCTTG GCTAATAACT ATTTCCCATT TTATAAGTTA              6669

TTGACGGATG GTTTTATCAA ATATGAGATC AAATCTTATT TTAAATTCGC TTTCCATTAA              6729

GCGATAT                                                                         6736

(2) INFORMATION FOR SEQ ID NO: 2:

(i) SEQUENCE CHARACTERISTICS:
        (A) LENGTH:  1657 amino acids
        (B) TYPE:  amino acid
        (D) TOPOLOGY:  linear (ii) MOLECULE TYPE: protein (xi) SEQUENCE DESCRIPTION: SEQ ID NO: 2:

Met Ser Asp Asn Ala Phe Phe Val Ile Glu Glu Ser Gly Lys Arg Tyr
1               5                   10                  15

Ile Glu Asn Phe Gly Ile Glu Pro Leu Gly Lys Gln Glu Asp Phe Asp
                20                  25                  30

Phe Val Gly Gly Phe Trp Ser Asn Leu Val Asn Arg Gly Leu Glu Ser
            35                  40                  45

Ile Ile Asp Pro Ser Gly Ile Gly Gly Thr Val Asn Leu Asn Phe Thr
        50                  55                  60

Gly Glu Val Glu Thr Tyr Thr Leu Asp Glu Thr Arg Phe Lys Ala Glu
65                  70                  75                  80

Ala Ala Lys Lys Ser His Trp Ser Leu Val Asn Ala Ala Lys Val Tyr
                85                  90                  95

Gly Gly Leu Asp Gln Ile Ile Lys Lys Leu Trp Asp Ser Gly Ser Ile
            100                 105                 110

Lys His Leu Tyr Gln Asp Lys Asp Thr Gly Lys Leu Lys Pro Ile Ile
        115                 120                 125

Tyr Gly Thr Ala Gly Asn Asp Ser Lys Ile Glu Gly Thr Lys Ile Thr
    130                 135                 140

Arg Arg Ile Ala Gly Lys Glu Val Thr Leu Asp Ile Ala Asn Gln Lys
145                 150                 155                 160
```

-continued

```
Ile Glu Lys Gly Val Leu Glu Lys Leu Gly Leu Ser Val Ser Gly Ser
            165                 170                 175

Asp Ile Ile Lys Leu Leu Phe Gly Ala Leu Thr Pro Thr Leu Asn Arg
            180                 185                 190

Met Leu Leu Ser Gln Leu Ile Gln Ser Phe Ser Asp Ser Leu Ala Lys
            195                 200                 205

Leu Asp Asn Pro Leu Ala Pro Tyr Thr Lys Asn Gly Val Val Tyr Val
210                 215                 220

Thr Gly Lys Gly Asn Asp Val Leu Lys Gly Thr Glu His Glu Asp Leu
225                 230                 235                 240

Phe Leu Gly Gly Glu Gly Asn Asp Thr Tyr Tyr Ala Arg Val Gly Asp
            245                 250                 255

Thr Ile Glu Asp Ala Asp Gly Lys Gly Lys Val Tyr Phe Val Arg Glu
            260                 265                 270

Lys Gly Val Pro Lys Ala Asp Pro Lys Arg Val Glu Phe Ser Glu Tyr
            275                 280                 285

Ile Thr Lys Glu Glu Ile Lys Glu Val Glu Lys Gly Leu Leu Thr Tyr
            290                 295                 300

Ala Val Leu Glu Asn Tyr Asn Trp Glu Glu Lys Thr Ala Thr Phe Ala
305                 310                 315                 320

His Ala Thr Met Leu Asn Glu Leu Phe Thr Asp Tyr Thr Asn Tyr Arg
            325                 330                 335

Tyr Glu Val Lys Gly Leu Lys Leu Pro Ala Val Lys Lys Leu Lys Ser
            340                 345                 350

Pro Leu Val Glu Phe Thr Ala Asp Leu Leu Thr Val Thr Pro Ile Asp
            355                 360                 365

Glu Asn Gly Lys Ala Leu Ser Glu Lys Ser Ile Thr Val Lys Asn Phe
370                 375                 380

Lys Asn Gly Asp Leu Gly Ile Arg Leu Leu Asp Pro Asn Ser Tyr Tyr
385                 390                 395                 400

Tyr Phe Leu Glu Gly Gln Asp Thr Gly Phe Tyr Gly Pro Ala Phe Tyr
            405                 410                 415

Ile Glu Arg Lys Asn Gly Gly Ala Lys Asn Asn Ser Ser Gly Ala
            420                 425                 430

Gly Asn Ser Lys Asp Trp Gly Gly Asn Gly His Gly Asn His Arg Asn
            435                 440                 445

Asn Ala Ser Asp Leu Asn Lys Pro Asp Gly Asn Asn Gly Asn Asn Gln
450                 455                 460

Asn Asn Gly Ser Asn Gln Asp Asn His Ser Asp Val Asn Ala Pro Asn
465                 470                 475                 480

Asn Pro Gly Arg Asn Tyr Asp Ile Tyr Asp Pro Leu Ala Leu Asp Leu
            485                 490                 495

Asp Gly Asp Gly Leu Glu Thr Val Ser Met Asn Gly Arg Gln Gly Ala
            500                 505                 510

Leu Phe Asp His Glu Gly Lys Gly Ile Arg Thr Ala Thr Gly Trp Leu
            515                 520                 525

Ala Ala Asp Asp Gly Phe Leu Val Leu Asp Arg Asn Gln Asp Gly Ile
530                 535                 540

Ile Asn Asp Ile Ser Glu Leu Phe Ser Asn Lys Asn Gln Leu Ser Asp
545                 550                 555                 560

Gly Ser Ile Ser Ala His Gly Phe Ala Thr Leu Ala Asp Leu Asp Thr
            565                 570                 575

Asn Gln Asp Gln Arg Ile Asp Gln Asn Asp Lys Leu Phe Ser Lys Leu
```

-continued

```
                580                 585                 590
Gln Ile Trp Arg Asp Leu Asn Gln Asn Gly Phe Ser Glu Ala Asn Glu
            595                 600                 605
Leu Phe Ser Leu Glu Ser Leu Asn Ile Lys Ser Leu His Thr Ala Tyr
            610                 615                 620
Glu Glu Arg Asn Asp Phe Leu Ala Gly Asn Asn Ile Leu Ala Gln Leu
625                 630                 635                 640
Gly Lys Tyr Glu Lys Thr Asp Gly Thr Phe Ala Gln Met Gly Asp Leu
                645                 650                 655
Asn Phe Ser Phe Asn Pro Phe Tyr Ser Arg Phe Thr Glu Ala Leu Asn
            660                 665                 670
Leu Thr Glu Gln Gln Arg Arg Thr Ile Asn Leu Thr Gly Thr Gly Arg
            675                 680                 685
Val Arg Asp Leu Arg Glu Ala Ala Leu Ser Glu Glu Leu Ala Ala
690                 695                 700
Leu Leu Gln Gln Tyr Thr Lys Ala Ser Asp Phe Gln Ala Gln Arg Glu
705                 710                 715                 720
Leu Leu Pro Ala Ile Leu Asp Lys Trp Ala Thr Asp Leu Gln Tyr
            725                 730                 735
Gln His Tyr Asp Lys Thr Leu Leu Lys Thr Val Glu Ser Thr Asp Ser
            740                 745                 750
Ser Ala Ser Val Val Arg Val Thr Pro Ser Gln Leu Ser Ser Ile Arg
            755                 760                 765
Asn Ala Lys His Asp Pro Thr Val Met Gln Asn Phe Glu Gln Ser Lys
            770                 775                 780
Ala Lys Ile Ala Thr Leu Asn Ser Leu Tyr Gly Leu Asn Ile Asp Gln
785                 790                 795                 800
Leu Tyr Tyr Thr Thr Asp Lys Asp Ile Arg Tyr Ile Thr Asp Lys Val
                805                 810                 815
Asn Asn Met Tyr Gln Thr Thr Val Glu Leu Ala Tyr Arg Ser Leu Leu
            820                 825                 830
Leu Gln Thr Arg Leu Lys Lys Tyr Val Tyr Ser Val Asn Ala Lys Gln
            835                 840                 845
Phe Glu Gly Lys Trp Val Thr Asp Tyr Ser Arg Thr Glu Ala Leu Phe
850                 855                 860
Asn Ser Thr Phe Lys Gln Ser Pro Glu Asn Ala Leu Tyr Asp Leu Ser
865                 870                 875                 880
Glu Tyr Leu Ser Phe Phe Asn Asp Pro Thr Glu Trp Lys Glu Gly Leu
                885                 890                 895
Leu Leu Leu Ser Arg Tyr Ile Ser Tyr Ala Lys Ala Gln Gly Phe Tyr
            900                 905                 910
Glu Asn Trp Ala Ala Thr Ser Asn Leu Thr Ile Ala Arg Leu Arg Glu
            915                 920                 925
Ala Gly Val Ile Phe Ala Glu Ser Thr Asp Leu Lys Gly Asp Glu Lys
            930                 935                 940
Asn Asn Ile Leu Leu Gly Ser Gln Lys Asp Asn Leu Ser Gly Ser
945                 950                 955                 960
Ala Gly Asp Asp Leu Leu Ile Gly Gly Glu Gly Asn Asp Thr Leu Lys
                965                 970                 975
Gly Ser Tyr Gly Ala Asp Thr Tyr Ile Phe Ser Lys Gly His Gly Gln
            980                 985                 990
Asp Ile Val Tyr Glu Asp Thr Asn Asn Asp Asn Arg Ala Arg Asp Ile
            995                 1000                1005
```

-continued

Asp Thr Leu Lys Phe Thr Asp Val Asn Tyr Ala Glu Val Lys Phe Arg
    1010            1015                1020

Arg Val Asp Asn Asp Leu Met Leu Phe Gly Tyr His Asp Thr Asp Ser
1025            1030                1035            1040

Val Thr Val Lys Ser Phe Tyr Ser His Val Asp Tyr Gln Phe Asp Lys
            1045                1050                1055

Leu Glu Phe Ala Asp Arg Ser Ile Thr Arg Asp Glu Leu Ile Lys Ala
        1060                1065            1070

Gly Leu His Leu Tyr Gly Thr Asp Gly Asn Asp Ile Lys Asp His
        1075            1080            1085

Ala Asp Trp Asp Ser Ile Leu Glu Gly Gly Lys Gly Asn Asp Ile Leu
    1090            1095            1100

Arg Gly Gly Tyr Gly Ala Asp Thr Tyr Ile Phe Ser Lys Gly His Gly
1105            1110            1115            1120

Gln Asp Ile Val Tyr Glu Asp Thr Asn Asn Asp Asn Arg Ala Arg Asp
        1125            1130            1135

Ile Asp Thr Leu Lys Phe Thr Asp Val Asn Tyr Ala Glu Val Lys Phe
            1140            1145            1150

Arg Arg Val Asp Asn Asp Leu Met Leu Phe Gly Tyr His Asp Thr Asp
        1155            1160            1165

Ser Val Thr Ile Lys Ser Phe Tyr Asn His Val Asp Tyr Gln Phe Asp
    1170            1175            1180

Lys Leu Glu Phe Ala Asp Arg Ser Ile Thr Arg Asp Glu Leu Gly Lys
1185            1190            1195            1200

Gln Gly Met Ala Leu Phe Gly Thr Asp Gly Asp Asp Asn Ile Asn Asp
            1205            1210            1215

Trp Gly Arg Asn Ser Val Ile Asp Ala Gly Ala Gly Asn Asp Thr Val
        1220            1225            1230

Asn Gly Gly Asn Gly Asp Asp Thr Leu Ile Gly Gly Lys Gly Asn Asp
        1235            1240            1245

Ile Leu Arg Gly Gly Tyr Gly Ala Asp Thr Tyr Ile Phe Ser Lys Gly
    1250            1255            1260

His Gly Gln Asp Ile Val Tyr Glu Asp Thr Asn Asn Asp Asn Arg Ala
1265            1270            1275            1280

Arg Asp Ile Asp Thr Leu Lys Phe Thr Asp Val Asn Tyr Ala Glu Val
            1285            1290            1295

Lys Phe Arg Arg Val Asp Asn Asp Leu Met Leu Phe Gly Tyr His Asp
        1300            1305            1310

Thr Asp Ser Val Thr Val Lys Ser Phe Tyr Ser His Val Asp Tyr Gln
    1315            1320            1325

Phe Asp Lys Leu Glu Phe Ala Asp Arg Ser Ile Thr Arg Asp Glu Leu
    1330            1335            1340

Ile Lys Ala Gly Leu His Leu Tyr Gly Thr Asp Gly Asn Asp Asp Ile
1345            1350            1355            1360

Lys Asp His Ala Asp Trp Asp Ser Ile Leu Glu Gly Gly Lys Gly Asn
            1365            1370            1375

Asp Ile Leu Arg Gly Gly Tyr Gly Ala Asp Thr Tyr Ile Phe Ser Lys
        1380            1385            1390

Gly His Gly Gln Asp Ile Val Tyr Glu Asp Thr Asn Asn Asp Asn Arg
        1395            1400            1405

Ala Arg Asp Ile Asp Thr Leu Lys Phe Thr Asp Val Asn Tyr Ala Glu
    1410            1415            1420

Val Lys Phe Arg Arg Val Asp Asn Asp Leu Met Leu Phe Gly Tyr His
1425            1430            1435            1440

-continued

Asp Thr Asp Ser Val Thr Ile Lys Ser Phe Tyr Asn His Val Asp Tyr
            1445                1450                1455

Gln Phe Asp Lys Leu Glu Phe Ala Asp Arg Ser Ile Thr Arg Asp Glu
            1460                1465                1470

Leu Gly Lys Gln Gly Met Ala Leu Phe Gly Thr Asp Gly Asp Asp Asn
            1475                1480                1485

Ile Asn Asp Trp Gly Arg Asn Ser Val Ile Asp Ala Gly Ala Gly Asn
            1490                1495                1500

Asp Thr Val Asn Gly Gly Asn Gly Asp Asp Thr Leu Ile Gly Gly Lys
1505                1510                1515                1520

Gly Asn Asp Ile Leu Arg Gly Gly Tyr Gly Ala Asp Thr Tyr Ile Phe
            1525                1530                1535

Ser Lys Gly His Gly Gln Asp Ile Val Tyr Glu Asp Thr Asn Asn Asp
            1540                1545                1550

Asn Arg Ala Arg Asp Ile Asp Thr Leu Lys Phe Thr Asp Ile Asn Leu
            1555                1560                1565

Ser Glu Leu Trp Phe Ser Arg Glu Asn Asn Asp Leu Ile Ile Lys Ser
            1570                1575                1580

Leu Leu Ser Glu Asp Lys Val Thr Val Gln Asn Trp Tyr Ser His Gln
1585                1590                1595                1600

Asp His Lys Ile Glu Asn Ile Arg Leu Ser Asn Glu Gln Thr Leu Val
            1605                1610                1615

Ser Thr Gln Val Glu Lys Met Val Glu Ser Met Ala Gly Phe Ala Gln
            1620                1625                1630

Lys His Gly Gly Glu Ile Ser Leu Val Ser Leu Glu Glu Val Lys Gln
            1635                1640                1645

Tyr Ile Asn Ser Leu Thr Ala Ala Leu
    1650                1655

(2) INFORMATION FOR SEQ ID NO: 3:

(i) SEQUENCE CHARACTERISTICS:
        (A) LENGTH: 7004 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Actinobacillus pleuropneumoniae
        (B) STRAIN: HV114 (serotype 3 field strain)

(vii) IMMEDIATE SOURCE:
(B) CLONE: pROK5

(ix) FEATURE:
(A) NAME/KEY: CDS
(B) LOCATION:1566..5714
(D) OTHER INFORMATION:/codon_start= 1566
/function= "RTX-toxin"
/product= "ApxIV_var3"
/gene= "apxIV_var3"
/number= 1

(xi) SEQUENCE DESCRIPTION: SEQ ID NO: 3:

```
ATCGATATGC CGCCGGGTAC GGGCGATATC CAACTTACTC TTTCGCAACA AATTCCGGTT     60

ACCGGTGCGG TAGTGGTAAC TACTCCGCAA GATATTGCGT TATTAGATGC GGTGAAAGGT    120
```

-continued

```
ATTTCAATGT TCCAAAAAGT GTCGGTACCG GTCTTAGGTA TCATTGAAAA TATGAGCGTG      180

CATATCTGCC AAAATTGCGG TCACCACGAA GATATTTTCG GCACCGGCGG TGCGGAGAAA      240

GTGGCGAAGA AATACGGTAC TAAAGTATTA GGACAAATGC CGTTGCATAT TCGCTTACGT      300

CAAGATTTGG ATGCCGGCAC ACCGACCGTC GTTGCGGCAC CGGAACACGA CACCAGCAGA      360

GCCTATATTG AATTAGCGGC AAAAGTCGCT TCGGAATTAT ACTGGCAAGG TTCGGTTATC      420

CCGTCTGAAA TTATGATTCG TGAAGTAAAA TAAGCCTACA TAACCACGGA ATACCAGATA      480

ACACAGAAGG AAAACAAGCG GTAGAATTTG CAGAAAAAGT TGCAAATTCT ACCGCTTTTT      540

TATTAGTACG ATTCGCTGTT GGACTGCCAT TTGATTTGGT TTGTCAGGAT ATTATGTTAT      600

TGTAATGAAA TGTTAGTGAA TTATTTTTAT TAATTTGAAA GGAGACAAAA TGAAAATAAA      660

AAAACGTTAC ATTGCGCTGC TAGCTTTAGG CAGTGTTATT GGCTATGCCT GGTATCAAAA      720

TTATCAATGG GAACAGTTGA TGTTAAGTGG CTATTGTGAA AAGGACGGAA GCTATTGTGA      780

TGATAGGCAT ACGAAGCAGG AACTGATTGA TAGGGCAATT AACTATGTGC TGGAAAATCA      840

AATTCAACAG ACATATGAAG GTGATGACCT TGTGGATATA AAACAATATT CAACAATAGA      900

GGAATTTAAA AAACTAAATC CGAATTGTTG TAAGGTAGAT TCTTGGCCGG ATGATGCTGT      960

TCGTGAGGAT GCTGATTTAC AGCGAGAGGG CAAAGCGTAT AAATACGTAA AAGTCAAATA     1020

TTTAAGAACC TATTTAGCGA ATAGAGAACC TGAACAATGG GAAAATTACA TAGTATTTGA     1080

TAATTGCAGT GGAATTAAAG AAAGACACCA ACTGTATTAA AAATAGATTA GATGGAGACA     1140

ACACGATGAC AAAACTAACT ATCCAAGATG TGACTAATTT ATATTTATAT AAGCAAAGAA     1200

CTTTACCTAC GGATAGGTTA GATGATTCGC TTATTAGCAA AACAGGAAAA GGGGAAAATA     1260

TTGATAAAAA GGAATTTATG GCGGGGCCGG GACGTTTTGT GACGGCCGAT AATTTTAGTG     1320

TTGTAAAAGA CTTTTTTACT GCAAAGGATT CATTAATAAA CCTAAGCTTG CAGACTCGTA     1380

TATTAGCGAA TTTAAAGCCG GGCAAATATT CCAAAGCGCA GATATTAGAA ATGTTGGGCT     1440

ATACGAAAAA TGGAGAAAAG GTAGATGGCA TGTTTACCGG TGAAGTCCAG ACATTAGGCT     1500

TTTATGACGA TGGCAAAGGG GATTTACTCG AACGCGCCTA TATCTGAAAT ACCACAGGAT     1560
```

| TTAAA ATG AGC GAC AAT GCC TTT TTT GTT ATA GAA GAA TCA GGC AAA | 1607 |
|---|---|
| Met Ser Asp Asn Ala Phe Phe Val Ile Glu Glu Ser Gly Lys | |
| 1660              1665              1670 | |
| CGC TAT ATT GAA AAC TTT GGT ATT GAA CCT CTT GGT AAG CAA GAA GAT | 1655 |
| Arg Tyr Ile Glu Asn Phe Gly Ile Glu Pro Leu Gly Lys Gln Glu Asp | |
| 1675              1680              1685 | |
| TTT GAT TTT GTC GGC GGC TTT TGG TCT AAC TTA GTG AAT CGT GGT TTG | 1703 |
| Phe Asp Phe Val Gly Gly Phe Trp Ser Asn Leu Val Asn Arg Gly Leu | |
| 1690              1695              1700 | |
| GAA AGT ATT ATC GAC CCA TCC GGT ATC GGT GGA ACG GTA AAC CTT AAC | 1751 |
| Glu Ser Ile Ile Asp Pro Ser Gly Ile Gly Gly Thr Val Asn Leu Asn | |
| 1705              1710              1715              1720 | |
| TTT ACC GGC GAG GTG GAA ACC TAC ACG TTA GAC GAA ACA AGG TTT AAA | 1799 |
| Phe Thr Gly Glu Val Glu Thr Tyr Thr Leu Asp Glu Thr Arg Phe Lys | |
| 1725              1730              1735 | |
| GCG GAA GCG GCG AAG AAA AGC CAT TGG AGT TTA GTG AAT GCG GCG AAA | 1847 |
| Ala Glu Ala Ala Lys Lys Ser His Trp Ser Leu Val Asn Ala Ala Lys | |
| 1740              1745              1750 | |
| GTA TAC GGC GGT TTA GAC CAA ATT ATT AAA AAA CTA TGG GAC AGT GGC | 1895 |
| Val Tyr Gly Gly Leu Asp Gln Ile Ile Lys Lys Leu Trp Asp Ser Gly | |
| 1755              1760              1765 | |
| TCA ATT AAG CAT TTA TAT CAA GAT AAA GAT ACG GGC AAA TTA AAA CCG | 1943 |
| Ser Ile Lys His Leu Tyr Gln Asp Lys Asp Thr Gly Lys Leu Lys Pro | |
| 1770              1775              1780 | |

```
ATT ATT TAC GGC ACG GCC GGC AAC GAC AGT AAG ATT GAA GGC ACT AAA      1991
Ile Ile Tyr Gly Thr Ala Gly Asn Asp Ser Lys Ile Glu Gly Thr Lys
1785                1790                1795                1800

ATC ACC CGT AGG ATT GCG GGT AAA GAA GTT ACG CTT GAT ATT GCC AAT      2039
Ile Thr Arg Arg Ile Ala Gly Lys Glu Val Thr Leu Asp Ile Ala Asn
                1805                1810                1815

CAG AAA ATT GAA AAA GGC GTG TTA GAG AAA TTG GGG CTG TCT GTT AGT      2087
Gln Lys Ile Glu Lys Gly Val Leu Glu Lys Leu Gly Leu Ser Val Ser
1820                1825                1830

GGT TCG GAT ATC ATT AAA TTG TTG TTT GGA GCA TTG ACT CCA ACT TTA      2135
Gly Ser Asp Ile Ile Lys Leu Leu Phe Gly Ala Leu Thr Pro Thr Leu
        1835                1840                1845

AAT AGA ATG TTG CTA TCA CAA CTT ATC CAG TCT TTT TCC GAT AGC TTG      2183
Asn Arg Met Leu Leu Ser Gln Leu Ile Gln Ser Phe Ser Asp Ser Leu
1850                1855                1860

GCT AAA CTT GAT AAT CCC TTA GCC CCT TAC ACT AAA AAT GGC GTG GTT      2231
Ala Lys Leu Asp Asn Pro Leu Ala Pro Tyr Thr Lys Asn Gly Val Val
1865                1870                1875                1880

TAT GTC ACC GGC AAA GGG AAT GAT GTG CTT AAA GGA ACT GAA CAT GAG      2279
Tyr Val Thr Gly Lys Gly Asn Asp Val Leu Lys Gly Thr Glu His Glu
                1885                1890                1895

GAT TTG TTT CTC GGT GGT GAG GGG AAT GAT ACT TAT TAT GCG AGA GTA      2327
Asp Leu Phe Leu Gly Gly Glu Gly Asn Asp Thr Tyr Tyr Ala Arg Val
                1900                1905                1910

GGC GAT ACA ATT GAA GAC GCC GAC GGC AAA GGT AAA GTC TAT TTT GTG      2375
Gly Asp Thr Ile Glu Asp Ala Asp Gly Lys Gly Lys Val Tyr Phe Val
        1915                1920                1925

AGA GAA AAA GGG GTA CCT AAG GCG GAT CCT AAG CGG GTA GAG TTT AGC      2423
Arg Glu Lys Gly Val Pro Lys Ala Asp Pro Lys Arg Val Glu Phe Ser
1930                1935                1940

GAG TAC ATA ACG AAA GAA GAA ATA AAA GAG GTT GAA AAG GGG TTA TTA      2471
Glu Tyr Ile Thr Lys Glu Glu Ile Lys Glu Val Glu Lys Gly Leu Leu
1945                1950                1955                1960

ACT TAC GCA GTT TTA GAA AAT TAT AAT TGG GAA GAG AAA ACG GCG ACT      2519
Thr Tyr Ala Val Leu Glu Asn Tyr Asn Trp Glu Glu Lys Thr Ala Thr
                1965                1970                1975

TTC GCT CAT GCG ACT ATG CTT AAT GAG CTT TTT ACT GAT TAT ACT AAT      2567
Phe Ala His Ala Thr Met Leu Asn Glu Leu Phe Thr Asp Tyr Thr Asn
        1980                1985                1990

TAT CGT TAT GAA GTT AAA GGA CTA AAA TTG CCC GCC GTT AAA AAG TTA      2615
Tyr Arg Tyr Glu Val Lys Gly Leu Lys Leu Pro Ala Val Lys Lys Leu
        1995                2000                2005

AAA AGT CCG TTG GTG GAG TTT ACA GCT GAT TTA TTA ACT GTT ACG CCT      2663
Lys Ser Pro Leu Val Glu Phe Thr Ala Asp Leu Leu Thr Val Thr Pro
2010                2015                2020

ATT GAC GAA AAC GGA AAA GCA CTT AGC GAA AAA AGT ATT ACG GTT AAA      2711
Ile Asp Glu Asn Gly Lys Ala Leu Ser Glu Lys Ser Ile Thr Val Lys
2025                2030                2035                2040

AAT TTT AAA AAT GGT GAT TTA GGA ATA AGG TTG TTG GAT CCT AAT AGC      2759
Asn Phe Lys Asn Gly Asp Leu Gly Ile Arg Leu Leu Asp Pro Asn Ser
                2045                2050                2055

TAT TAT TAT TTC CTT GAA GGC CAA GAT ACG GGT TTT TAT GGT CCT GCT      2807
Tyr Tyr Tyr Phe Leu Glu Gly Gln Asp Thr Gly Phe Tyr Gly Pro Ala
                2060                2065                2070

TTT TAT ATT GAA CGA AAA AAC GGT GGA GGC TCT AAA AAT AAC TCG TCG      2855
Phe Tyr Ile Glu Arg Lys Asn Gly Gly Gly Ser Lys Asn Asn Ser Ser
            2075                2080                2085

GGA GCA GGA AAT AGC AAA GAT TGG GGC GGG AAC GGG CAT GGA AAT CAC      2903
Gly Ala Gly Asn Ser Lys Asp Trp Gly Gly Asn Gly His Gly Asn His
        2090                2095                2100
```

```
CGA AAT AAT GCC TCC GAC CTG AAT AAA CCG GAC GGA AAT AAT GGG AAT      2951
Arg Asn Asn Ala Ser Asp Leu Asn Lys Pro Asp Gly Asn Asn Gly Asn
2105                2110                2115                2120

AAC CAA AAT AAC GGA AGC AAT CAA GAT AAT CAT AGC GAT GTG AAT GCG      2999
Asn Gln Asn Asn Gly Ser Asn Gln Asp Asn His Ser Asp Val Asn Ala
                2125                2130                2135

CCA AAT AAC CCG GGA CGT AAC TAT GAT ATT TAC GAT CCT TTA GCT TTA      3047
Pro Asn Asn Pro Gly Arg Asn Tyr Asp Ile Tyr Asp Pro Leu Ala Leu
            2140                2145                2150

GAT TTA GAT GGA GAT GGG CTT GAA ACC GTG TCG ATG AAC GGG CGA CAA      3095
Asp Leu Asp Gly Asp Gly Leu Glu Thr Val Ser Met Asn Gly Arg Gln
        2155                2160                2165

GGC GCG TTA TTC GAT CAT GAA GGA AAA GGT ATT CGT ACC GCA ACG GGC      3143
Gly Ala Leu Phe Asp His Glu Gly Lys Gly Ile Arg Thr Ala Thr Gly
    2170                2175                2180

TGG CTC GCT GCG GAT GAC GGT TTT TTA GTG TTA GAT CGT AAC CAA GAC      3191
Trp Leu Ala Ala Asp Asp Gly Phe Leu Val Leu Asp Arg Asn Gln Asp
2185                2190                2195                2200

GGC ATT ATT AAT GAT ATA AGC GAG TTA TTT AGT AAT AAA AAT CAA CTT      3239
Gly Ile Ile Asn Asp Ile Ser Glu Leu Phe Ser Asn Lys Asn Gln Leu
                2205                2210                2215

TCC GAC GGG AGT ATT TCT GCA CAC GGT TTT GCG ACA TTA GCC GAT TTG      3287
Ser Asp Gly Ser Ile Ser Ala His Gly Phe Ala Thr Leu Ala Asp Leu
            2220                2225                2230

GAT ACA AAC CAA GAT CAG CGT ATC GAC CAA AAT GAT AAG CTG TTT TCT      3335
Asp Thr Asn Gln Asp Gln Arg Ile Asp Gln Asn Asp Lys Leu Phe Ser
        2235                2240                2245

AAA CTC CAA ATT TGG CGG GAT TTA AAT CAA AAC GGT TTT AGT GAA GCG      3383
Lys Leu Gln Ile Trp Arg Asp Leu Asn Gln Asn Gly Phe Ser Glu Ala
    2250                2255                2260

AAT GAG CTG TTT AGC TTA GAA AGT TTG AAT ATT AAA TCT TTA CAT ACC      3431
Asn Glu Leu Phe Ser Leu Glu Ser Leu Asn Ile Lys Ser Leu His Thr
2265                2270                2275                2280

GCC TAT GAA GAG CGT AAT GAT TTT CTA GCG GGC AAT AAT ATC CTT GCT      3479
Ala Tyr Glu Glu Arg Asn Asp Phe Leu Ala Gly Asn Asn Ile Leu Ala
                2285                2290                2295

CAG CTT GGG AAG TAT GAA AAA ACG GAC GGT ACT TTT GGA CAA ATG GGC      3527
Gln Leu Gly Lys Tyr Glu Lys Thr Asp Gly Thr Phe Gly Gln Met Gly
            2300                2305                2310

GAT TTA AAT TTC AGT TTT AAC CCG TTT TAT AGC CGA TTT ACC GAA GCG      3575
Asp Leu Asn Phe Ser Phe Asn Pro Phe Tyr Ser Arg Phe Thr Glu Ala
        2315                2320                2325

TTA AAT TTA ACC GAG CAA CAA CGT CGC ACA ATT AAT CTA ACC GGC ACC      3623
Leu Asn Leu Thr Glu Gln Gln Arg Arg Thr Ile Asn Leu Thr Gly Thr
    2330                2335                2340

GGT CGG GTT CGG GAT TTG CGT GAA GCC GCC GCA CTT TCT GAG GAG TTG      3671
Gly Arg Val Arg Asp Leu Arg Glu Ala Ala Ala Leu Ser Glu Glu Leu
2345                2350                2355                2360

GCT GCT TTA TTA CAA CAG TAC ACT AAG GGC TCC GAT TTT CAG GCA CAA      3719
Ala Ala Leu Leu Gln Gln Tyr Thr Lys Gly Ser Asp Phe Gln Ala Gln
                2365                2370                2375

CGA GAA TTA TTG CCT GCC ATT TTA GAT AAA TGG GCG GCA ACG GAT TTA      3767
Arg Glu Leu Leu Pro Ala Ile Leu Asp Lys Trp Ala Ala Thr Asp Leu
            2380                2385                2390

CAG TAT CAA CAT TAT GAT AAA ACA TTA CTT AAA ACG GTA GAA AGT ACC      3815
Gln Tyr Gln His Tyr Asp Lys Thr Leu Leu Lys Thr Val Glu Ser Thr
        2395                2400                2405

GAT AGT AGT GCT TCT GTC GTT AGA GTC ACG CCT TCT CAA TTA AGT AGT      3863
Asp Ser Ser Ala Ser Val Val Arg Val Thr Pro Ser Gln Leu Ser Ser
2410                2415                2420
```

```
ATA CGC AAT GTA AAG CAT GAT CCT ACC GTT ATG CAA AAC TGT GAA CAA    3911
Ile Arg Asn Val Lys His Asp Pro Thr Val Met Gln Asn Cys Glu Gln
2425                2430                2435                2440

AGT AAG GCA AAA ATT GCG ACT TTA AAT TCG CTC TAC GGG TTA AAT ATT    3959
Ser Lys Ala Lys Ile Ala Thr Leu Asn Ser Leu Tyr Gly Leu Asn Ile
            2445                2450                2455

GAT CAA CTT TAT TAT ACG ACG GAT AAA GAC ATT CGT TAT ATT ACT GAC    4007
Asp Gln Leu Tyr Tyr Thr Thr Asp Lys Asp Ile Arg Tyr Ile Thr Asp
        2460                2465                2470

AAA GTG AAT AAT ATG TAT CAA ACA ACC GGA GAA CTC GGC TAT CGT TCT    4055
Lys Val Asn Asn Met Tyr Gln Thr Thr Gly Glu Leu Gly Tyr Arg Ser
    2475                2480                2485

TTA CTT TTA CAA ACG CGT GTG AAG AAA TAT GTT TAT AGC GTT AAT GCG    4103
Leu Leu Leu Gln Thr Arg Val Lys Lys Tyr Val Tyr Ser Val Asn Ala
2490                2495                2500

AAA CAA TTC GAA GGG AAA TGG GTA GCC GAT TAT TCT CGT ACT GAA GCC    4151
Lys Gln Phe Glu Gly Lys Trp Val Ala Asp Tyr Ser Arg Thr Glu Ala
2505                2510                2515                2520

TTA TTT AAC TCT ACT TAT AAA CAA TCG CCC GAA AAT GTA TTA TAT GAT    4199
Leu Phe Asn Ser Thr Tyr Lys Gln Ser Pro Glu Asn Val Leu Tyr Asp
            2525                2530                2535

TTA CGC GAA TAC CTT TCT TTC TAT AAC GAC CCT ACG GAA TGG AAA GAA    4247
Leu Arg Glu Tyr Leu Ser Phe Tyr Asn Asp Pro Thr Glu Trp Lys Glu
        2540                2545                2550

GGG CTA TTA CTG TTA AGC CGT TAT ATA GAT TAT GCT AAA GCA CAA GGA    4295
Gly Leu Leu Leu Leu Ser Arg Tyr Ile Asp Tyr Ala Lys Ala Gln Gly
    2555                2560                2565

TTT TAT GAA AAC TGG GCG GCT ACT TCT AAC TTA ACT ATT GCC CGT TTA    4343
Phe Tyr Glu Asn Trp Ala Ala Thr Ser Asn Leu Thr Ile Ala Arg Leu
2570                2575                2580

AGA GAG GCT GGA GTA ATT TGT GCA GAA TCG ACG GAT TTA AAA GGC GAT    4391
Arg Glu Ala Gly Val Ile Cys Ala Glu Ser Thr Asp Leu Lys Gly Asp
2585                2590                2595                2600

GAA AAA AAT AAT ATT GTG TTA GGT AGC CAA AAA GAT AAT AAC TTA TCG    4439
Glu Lys Asn Asn Ile Val Leu Gly Ser Gln Lys Asp Asn Asn Leu Ser
            2605                2610                2615

GGT AGT GCA GGT GAT GAT CTA CTT ATC GGC GGA GAG GGT AAT GAT ACG    4487
Gly Ser Ala Gly Asp Asp Leu Leu Ile Gly Gly Glu Gly Asn Asp Thr
        2620                2625                2630

TTA AAA GGC AGC TAC GGT GCA GAC ACC TAT ATC TTT AGC AAA GGG CAT    4535
Leu Lys Gly Ser Tyr Gly Ala Asp Thr Tyr Ile Phe Ser Lys Gly His
    2635                2640                2645

GGA CAA GAT GTA ATT TAT GAA TAT TCC GAC AGT GCA AAC TCT AAA AAA    4583
Gly Gln Asp Val Ile Tyr Glu Tyr Ser Asp Ser Ala Asn Ser Lys Lys
2650                2655                2660

GAT ATT GAT ACC TTA AAA TTT ACC GAT GTG AAT TAT GCG GAA GTG AAG    4631
Asp Ile Asp Thr Leu Lys Phe Thr Asp Val Asn Tyr Ala Glu Val Lys
2665                2670                2675                2680

TTT CGA CGA GTA GAT AAT GAC TTA ATG TTA TTC GGT TAT CAT GAT ACG    4679
Phe Arg Arg Val Asp Asn Asp Leu Met Leu Phe Gly Tyr His Asp Thr
            2685                2690                2695

GAT TCG GTC ACG GTA AAA TCC TTC TAC AGC CAT GTA GAT TAT CAA TTT    4727
Asp Ser Val Thr Val Lys Ser Phe Tyr Ser His Val Asp Tyr Gln Phe
        2700                2705                2710

GAC AAA TTG GAG TTT GCT GAC CGC AGT ATA ACT CGC GAT GAA CTG ATT    4775
Asp Lys Leu Glu Phe Ala Asp Arg Ser Ile Thr Arg Asp Glu Leu Ile
    2715                2720                2725

AAA GCA GGG CTT CAT CTA TAC GGC ACC GAT GGC AAT GAT GAT ATA AAG    4823
Lys Ala Gly Leu His Leu Tyr Gly Thr Asp Gly Asn Asp Asp Ile Lys
2730                2735                2740
```

```
GAT CAT GCG GAT TGG GAC AGC ATT GTG GAA GGC GGC AAA GGC AAC GAT    4871
Asp His Ala Asp Trp Asp Ser Ile Val Glu Gly Gly Lys Gly Asn Asp
2745                2750                2755                2760

ATT CTA AGA GGT GGC TAC GGT GCG GAC ACC TAT ATC TTT AGC AAA GGA    4919
Ile Leu Arg Gly Gly Tyr Gly Ala Asp Thr Tyr Ile Phe Ser Lys Gly
            2765                2770                2775

CAC GGA CAG GAT ATC GTT TAT GAA GAT ACC AAT AAT GAT AAC CGA GCA    4967
His Gly Gln Asp Ile Val Tyr Glu Asp Thr Asn Asn Asp Asn Arg Ala
                2780                2785                2790

AGA GAT ATC GAC ACC TTA ACA TTT ACT GAT GTG AAT TAT GCG GAA GTG    5015
Arg Asp Ile Asp Thr Leu Thr Phe Thr Asp Val Asn Tyr Ala Glu Val
2795                2800                2805

AAA TTC CGA CGA GTA GAT AAT GAC TTA ATG TTA TTC GGT TAT CAT GAT    5063
Lys Phe Arg Arg Val Asp Asn Asp Leu Met Leu Phe Gly Tyr His Asp
    2810                2815                2820

ACG GAT TCG GTC ACG ATA AAA TCC TTC TAC AAC CAT GTA GAT TAT CAA    5111
Thr Asp Ser Val Thr Ile Lys Ser Phe Tyr Asn His Val Asp Tyr Gln
2825                2830                2835                2840

TGT GAC AAA TTG GAC TTT GCT GAC CGC AGT ATA ACT CGT GAT GAA CTA    5159
Cys Asp Lys Leu Asp Phe Ala Asp Arg Ser Ile Thr Arg Asp Glu Leu
            2845                2850                2855

GGT AAA CAA GGT ATG GCA TTA TTT GGC ACT GAC GGC GAT GAT AAT ATC    5207
Gly Lys Gln Gly Met Ala Leu Phe Gly Thr Asp Gly Asp Asp Asn Ile
                2860                2865                2870

AAC GAC TGG GGA CGT AAC TCG GTG ATT GAT GCC GGT GCG GGT AAT GAT    5255
Asn Asp Trp Gly Arg Asn Ser Val Ile Asp Ala Gly Ala Gly Asn Asp
2875                2880                2885

ACG GTT AAT GGC GGT AAT GGC GAT GAC ACC CTC ATC GGC GGC AAA GGT    5303
Thr Val Asn Gly Gly Asn Gly Asp Asp Thr Leu Ile Gly Gly Lys Gly
    2890                2895                2900

AAT GAT ATT CTA AGA GGT GGC TAC GGT GCG GAC ACC TAT ATC TTT AGC    5351
Asn Asp Ile Leu Arg Gly Gly Tyr Gly Ala Asp Thr Tyr Ile Phe Ser
2905                2910                2915                2920

AAA GGA CAC GGA CAG GAT ATC GTT TAT GAA GAT ACC AAT AAT GAT AAC    5399
Lys Gly His Gly Gln Asp Ile Val Tyr Glu Asp Thr Asn Asn Asp Asn
            2925                2930                2935

CGC GCA AGA GAT ATC GAC ACC TTA AAA TTT ACT GAT ATT AAT TTA TCC    5447
Arg Ala Arg Asp Ile Asp Thr Leu Lys Phe Thr Asp Ile Asn Leu Ser
                2940                2945                2950

GAA CTT TGG TTT AGC CGA GAA AAT AAC GAT TTG ATT ATT AAA TCA TTA    5495
Glu Leu Trp Phe Ser Arg Glu Asn Asn Asp Leu Ile Ile Lys Ser Leu
2955                2960                2965

TTA AGT GAG GAT AAA GTC ACG GTT CAA AAT TGG TAT TCA CAC CAA GAT    5543
Leu Ser Glu Asp Lys Val Thr Val Gln Asn Trp Tyr Ser His Gln Asp
    2970                2975                2980

CAT AAA ATA GAA AAT ATT CGT TTA TCG AAT GAG CAA ATG TTG GTG AGC    5591
His Lys Ile Glu Asn Ile Arg Leu Ser Asn Glu Gln Met Leu Val Ser
2985                2990                2995                3000

ACT CAG GTG GAG AAG ATG GTT GAG TCG ATG GCC GGC TTT GCT CAG AAG    5639
Thr Gln Val Glu Lys Met Val Glu Ser Met Ala Gly Phe Ala Gln Lys
            3005                3010                3015

CAC GGA GGA GAG ATA TCT CTT CTG TCG CCT GAA GAG GTA AAA CAA TAT    5687
His Gly Gly Glu Ile Ser Leu Leu Ser Pro Glu Glu Val Lys Gln Tyr
                3020                3025                3030

ATC AAT AGC TTA ACA GCT GCT TTA TAA CATACGAAAG AAATCGGCAC          5734
Ile Asn Ser Leu Thr Ala Ala Leu  *
                3035                3040

AGTTTTTGTG AACTGTGCCG ATTTGATTTT AGTGTAAGAA TATAGCCTGA TTTTAAGAAA  5794

TTTACTCTTG GCTAATAACT ATTTCCCATT TTATAAGTTA TTGACGGATG GTTTTATCAA  5854
```

```
ATATGAGATC AAATCTTATT TTAAATTCGC TTTCCATTAA GCGATATTGA TCTTTTAAGT    5914

TTGGGGCCGC ATGAGTTTGG AACCGATACC ACTCATTGTG GGAATCAATA CACAATACGC    5974

TGTAATCGGA CTCTTGCAGT TCATAATAAT GCTTTCTCTC CGTTAATTCT TCTTGCGTAT    6034

ATGGCGAGAG ATTAAAGCTG AATGGCTGGT TCGCACTAAC AAACAGGTTC TCCGATTTCA    6094

GATATTCACA ACCGTAATGG CTACCGGTTT CCTGCGGTTT TACATAATTG GTATGATTTT    6154

GTTTAGCTGT TATACGGTAG ATGCCTAATT GTGGTAAATT GCGTGTGTCA ATATAGCTTT    6214

CTTGTTCTCC GTAACCGAAA TACTCAATGG CGTTTTCTGT TTTAGCTAAG AAGAAACGTA    6274

AGCCGAAGCG GGGTAAATAC GGTAATTCGA TCGGGCGAAT AGCGTTAATT TCAACCGAAA    6334

GTTGTCCGTC ATTGAAGATA CGATAACGAA TATCCAGTGT TAAAATGCGA CCGCGAGAAA    6394

TTGACACAAT TGCAGATTTT ACTGAAAATT CGACCGCTTG TTCGCTTTGC TGCCACTGAA    6454

TTTCATACGC TCTGGTATAG GCTTTATCGT AGCCGGCATT TTGGCACGCC TCACGAATGA    6514

GGCGATCATT GTCGGTTGGC GCACGCCAAA TATTAAAATC TAACGATTGT TGGATAATCG    6574

CTTTACCGGC TTTTTCAATA CGGGTGAAAA TCCCTTTCTG TTTATCTAAT TGATAACTAA    6634

ATTGACCGTT GTGTACGTTA ATGTGGAAGC GATCTTCTTG TACTTCAAAT GCACTGTTCT    6694

CAATTGTGAA TTGTGGTAAT ACTAATTTAT TTTCGCTAAA TAAATTGAGC TGCTCGAAGC    6754

CAAGTGAATG TGCTTCGTCT AATAATTCGA CCGCGGTATT TAAGCGATAA TTTAAATTCA    6814

GTAGCCATAA ATGCCCGTTA TTTTTTGGTA ACTCAATCGG TAATACTACG CTGCCGTGCG    6874

GTTGGCAAGA AACGGATAAA TTCCCACCGC TTGTCACCAC GCCGTTTTCG ACAAATTCGT    6934

AATCAATCGT TAAATAATCG GCAAGATCAG TGAAATCCAA GTAGTTGTGG ATCACAATTT    6994

GGTTATCGAT                                                           7004
```

(2) INFORMATION FOR SEQ ID NO: 4:

(i) SEQUENCE CHARACTERISTICS:
        (A) LENGTH: 1382 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Ser Asp Asn Ala Phe Phe Val Ile Glu Glu Ser Gly Lys Arg Tyr
 1               5                  10                  15

Ile Glu Asn Phe Gly Ile Glu Pro Leu Gly Lys Gln Glu Asp Phe Asp
            20                  25                  30

Phe Val Gly Gly Phe Trp Ser Asn Leu Val Asn Arg Gly Leu Glu Ser
        35                  40                  45

Ile Ile Asp Pro Ser Gly Ile Gly Gly Thr Val Asn Leu Asn Phe Thr
    50                  55                  60

Gly Glu Val Glu Thr Tyr Thr Leu Asp Glu Thr Arg Phe Lys Ala Glu
65                  70                  75                  80

Ala Ala Lys Lys Ser His Trp Ser Leu Val Asn Ala Ala Lys Val Tyr
                85                  90                  95

Gly Gly Leu Asp Gln Ile Ile Lys Lys Leu Trp Asp Ser Gly Ser Ile
            100                 105                 110

Lys His Leu Tyr Gln Asp Lys Asp Thr Gly Lys Leu Lys Pro Ile Ile
        115                 120                 125

Tyr Gly Thr Ala Gly Asn Asp Ser Lys Ile Glu Gly Thr Lys Ile Thr
    130                 135                 140

Arg Arg Ile Ala Gly Lys Glu Val Thr Leu Asp Ile Ala Asn Gln Lys
```

-continued

```
            145                 150                 155                 160
        Ile Glu Lys Gly Val Leu Glu Lys Leu Gly Leu Ser Val Ser Gly Ser
                        165                 170                 175
        Asp Ile Ile Lys Leu Leu Phe Gly Ala Leu Thr Pro Thr Leu Asn Arg
                        180                 185                 190
        Met Leu Leu Ser Gln Leu Ile Gln Ser Phe Ser Asp Ser Leu Ala Lys
                        195                 200                 205
        Leu Asp Asn Pro Leu Ala Pro Tyr Thr Lys Asn Gly Val Val Tyr Val
            210                 215                 220
        Thr Gly Lys Gly Asn Asp Val Leu Lys Gly Thr Glu His Glu Asp Leu
        225                 230                 235                 240
        Phe Leu Gly Gly Glu Gly Asn Asp Thr Tyr Tyr Ala Arg Val Gly Asp
                        245                 250                 255
        Thr Ile Glu Asp Ala Asp Gly Lys Gly Lys Val Tyr Phe Val Arg Glu
                        260                 265                 270
        Lys Gly Val Pro Lys Ala Asp Pro Lys Arg Val Glu Phe Ser Glu Tyr
                        275                 280                 285
        Ile Thr Lys Glu Glu Ile Lys Glu Val Glu Lys Gly Leu Leu Thr Tyr
                        290                 295                 300
        Ala Val Leu Glu Asn Tyr Asn Trp Glu Glu Lys Thr Ala Thr Phe Ala
        305                 310                 315                 320
        His Ala Thr Met Leu Asn Glu Leu Phe Thr Asp Tyr Thr Asn Tyr Arg
                        325                 330                 335
        Tyr Glu Val Lys Gly Leu Lys Leu Pro Ala Val Lys Lys Leu Lys Ser
                        340                 345                 350
        Pro Leu Val Glu Phe Thr Ala Asp Leu Leu Thr Val Thr Pro Ile Asp
                        355                 360                 365
        Glu Asn Gly Lys Ala Leu Ser Glu Lys Ser Ile Thr Val Lys Asn Phe
                        370                 375                 380
        Lys Asn Gly Asp Leu Gly Ile Arg Leu Leu Asp Pro Asn Ser Tyr Tyr
        385                 390                 395                 400
        Tyr Phe Leu Glu Gly Gln Asp Thr Gly Phe Tyr Gly Pro Ala Phe Tyr
                        405                 410                 415
        Ile Glu Arg Lys Asn Gly Gly Ser Lys Asn Asn Ser Ser Gly Ala
                        420                 425                 430
        Gly Asn Ser Lys Asp Trp Gly Asn Gly His Gly Asn His Arg Asn
                        435                 440                 445
        Asn Ala Ser Asp Leu Asn Lys Pro Asp Gly Asn Asn Gly Asn Asn Gln
            450                 455                 460
        Asn Asn Gly Ser Asn Gln Asp Asn His Ser Asp Val Asn Ala Pro Asn
        465                 470                 475                 480
        Asn Pro Gly Arg Asn Tyr Asp Ile Tyr Asp Pro Leu Ala Leu Asp Leu
                        485                 490                 495
        Asp Gly Asp Gly Leu Glu Thr Val Ser Met Asn Gly Arg Gln Gly Ala
                        500                 505                 510
        Leu Phe Asp His Glu Gly Lys Gly Ile Arg Thr Ala Thr Gly Trp Leu
                        515                 520                 525
        Ala Ala Asp Asp Gly Phe Leu Val Leu Asp Arg Asn Gln Asp Gly Ile
                        530                 535                 540
        Ile Asn Asp Ile Ser Glu Leu Phe Ser Asn Lys Asn Gln Leu Ser Asp
        545                 550                 555                 560
        Gly Ser Ile Ser Ala His Gly Phe Ala Thr Leu Ala Asp Leu Asp Thr
                        565                 570                 575
```

-continued

```
Asn Gln Asp Gln Arg Ile Asp Gln Asn Asp Lys Leu Phe Ser Lys Leu
            580                 585                 590

Gln Ile Trp Arg Asp Leu Asn Gln Asn Gly Phe Ser Glu Ala Asn Glu
        595                 600                 605

Leu Phe Ser Leu Glu Ser Leu Asn Ile Lys Ser Leu His Thr Ala Tyr
    610                 615                 620

Glu Glu Arg Asn Asp Phe Leu Ala Gly Asn Asn Ile Leu Ala Gln Leu
625                 630                 635                 640

Gly Lys Tyr Glu Lys Thr Asp Gly Thr Phe Gly Gln Met Gly Asp Leu
                645                 650                 655

Asn Phe Ser Phe Asn Pro Phe Tyr Ser Arg Phe Thr Glu Ala Leu Asn
            660                 665                 670

Leu Thr Glu Gln Gln Arg Arg Thr Ile Asn Leu Thr Gly Thr Gly Arg
        675                 680                 685

Val Arg Asp Leu Arg Glu Ala Ala Ala Leu Ser Glu Glu Leu Ala Ala
    690                 695                 700

Leu Leu Gln Gln Tyr Thr Lys Gly Ser Asp Phe Gln Ala Gln Arg Glu
705                 710                 715                 720

Leu Leu Pro Ala Ile Leu Asp Lys Trp Ala Thr Asp Leu Gln Tyr
                725                 730                 735

Gln His Tyr Asp Lys Thr Leu Leu Lys Thr Val Glu Ser Thr Asp Ser
            740                 745                 750

Ser Ala Ser Val Val Arg Val Thr Pro Ser Gln Leu Ser Ser Ile Arg
        755                 760                 765

Asn Val Lys His Asp Pro Thr Val Met Gln Asn Cys Glu Gln Ser Lys
    770                 775                 780

Ala Lys Ile Ala Thr Leu Asn Ser Leu Tyr Gly Leu Asn Ile Asp Gln
785                 790                 795                 800

Leu Tyr Tyr Thr Thr Asp Lys Asp Ile Arg Tyr Ile Thr Asp Lys Val
                805                 810                 815

Asn Asn Met Tyr Gln Thr Thr Gly Glu Leu Gly Tyr Arg Ser Leu Leu
            820                 825                 830

Leu Gln Thr Arg Val Lys Lys Tyr Val Tyr Ser Val Asn Ala Lys Gln
        835                 840                 845

Phe Glu Gly Lys Trp Val Ala Asp Tyr Ser Arg Thr Glu Ala Leu Phe
    850                 855                 860

Asn Ser Thr Tyr Lys Gln Ser Pro Glu Asn Val Leu Tyr Asp Leu Arg
865                 870                 875                 880

Glu Tyr Leu Ser Phe Tyr Asn Asp Pro Thr Glu Trp Lys Glu Gly Leu
                885                 890                 895

Leu Leu Leu Ser Arg Tyr Ile Asp Tyr Ala Lys Ala Gln Gly Phe Tyr
            900                 905                 910

Glu Asn Trp Ala Ala Thr Ser Asn Leu Thr Ile Ala Arg Leu Arg Glu
        915                 920                 925

Ala Gly Val Ile Cys Ala Glu Ser Thr Asp Leu Lys Gly Asp Glu Lys
    930                 935                 940

Asn Asn Ile Val Leu Gly Ser Gln Lys Asp Asn Leu Ser Gly Ser
945                 950                 955                 960

Ala Gly Asp Asp Leu Leu Ile Gly Gly Glu Gly Asn Asp Thr Leu Lys
                965                 970                 975

Gly Ser Tyr Gly Ala Asp Thr Tyr Ile Phe Ser Lys Gly His Gly Gln
            980                 985                 990

Asp Val Ile Tyr Glu Tyr Ser Asp Ser Ala Asn Ser Lys Lys Asp Ile
        995                 1000                1005
```

```
Asp Thr Leu Lys Phe Thr Asp Val Asn Tyr Ala Glu Val Lys Phe Arg
    1010                1015                1020

Arg Val Asp Asn Asp Leu Met Leu Phe Gly Tyr His Asp Thr Asp Ser
1025            1030                1035                1040

Val Thr Val Lys Ser Phe Tyr Ser His Val Asp Tyr Gln Phe Asp Lys
            1045                1050                1055

Leu Glu Phe Ala Asp Arg Ser Ile Thr Arg Asp Glu Leu Ile Lys Ala
        1060                1065                1070

Gly Leu His Leu Tyr Gly Thr Asp Gly Asn Asp Ile Lys Asp His
        1075                1080                1085

Ala Asp Trp Asp Ser Ile Val Glu Gly Gly Lys Gly Asn Asp Ile Leu
        1090                1095                1100

Arg Gly Gly Tyr Gly Ala Asp Thr Tyr Ile Phe Ser Lys Gly His Gly
1105                1110                1115                1120

Gln Asp Ile Val Tyr Glu Asp Thr Asn Asn Asp Asn Arg Ala Arg Asp
        1125                1130                1135

Ile Asp Thr Leu Thr Phe Thr Asp Val Asn Tyr Ala Glu Val Lys Phe
            1140                1145                1150

Arg Arg Val Asp Asn Asp Leu Met Leu Phe Gly Tyr His Asp Thr Asp
        1155                1160                1165

Ser Val Thr Ile Lys Ser Phe Tyr Asn His Val Asp Tyr Gln Cys Asp
    1170                1175                1180

Lys Leu Asp Phe Ala Asp Arg Ser Ile Thr Arg Asp Glu Leu Gly Lys
1185                1190                1195                1200

Gln Gly Met Ala Leu Phe Gly Thr Asp Gly Asp Asn Ile Asn Asp
            1205                1210                1215

Trp Gly Arg Asn Ser Val Ile Asp Ala Gly Ala Gly Asn Asp Thr Val
        1220                1225                1230

Asn Gly Gly Asn Gly Asp Asp Thr Leu Ile Gly Gly Lys Gly Asn Asp
        1235                1240                1245

Ile Leu Arg Gly Gly Tyr Gly Ala Asp Thr Tyr Ile Phe Ser Lys Gly
        1250                1255                1260

His Gly Gln Asp Ile Val Tyr Glu Asp Thr Asn Asn Asp Asn Arg Ala
1265                1270                1275                1280

Arg Asp Ile Asp Thr Leu Lys Phe Thr Asp Ile Asn Leu Ser Glu Leu
            1285                1290                1295

Trp Phe Ser Arg Glu Asn Asn Asp Leu Ile Ile Lys Ser Leu Leu Ser
        1300                1305                1310

Glu Asp Lys Val Thr Val Gln Asn Trp Tyr Ser His Gln Asp His Lys
        1315                1320                1325

Ile Glu Asn Ile Arg Leu Ser Asn Glu Gln Met Leu Val Ser Thr Gln
        1330                1335                1340

Val Glu Lys Met Val Glu Ser Met Ala Gly Phe Ala Gln Lys His Gly
1345                1350                1355                1360

Gly Glu Ile Ser Leu Leu Ser Pro Glu Glu Val Lys Gln Tyr Ile Asn
            1365                1370                1375

Ser Leu Thr Ala Ala Leu
            1380

(2) INFORMATION FOR SEQ ID NO: 5:

(i) SEQUENCE CHARACTERISTICS:
        (A) LENGTH: 6736 base pairs
        (B) TYPE: nucleic acid
        (C) STRANDEDNESS: double
```

(D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Actinobacillus pleuropneumoniae
            (B) STRAIN: 4074 (serotype 1 reference strain)

(vii) IMMEDIATE SOURCE:
            (B) CLONE: pROK7

(ix) FEATURE:
            (A) NAME/KEY: CDS
            (B) LOCATION:1132..6549
            (C) IDENTIFICATION METHOD: experimental
            (D) OTHER INFORMATION:/codon_start= 1132
                /function= "RTX toxin"
                /product= "ApxIV"
                /evidence= EXPERIMENTAL
                /gene= "ApxIV_v1"

(ix) FEATURE:
            (A) NAME/KEY: CDS
            (B) LOCATION:1..453
            (D) OTHER INFORMATION:/partial
                /product= "Met-G"
                /gene= "mrp"
                /standard_name= "mrp"
                /label= mrp (ix) FEATURE:
            (A) NAME/KEY: -10_signal
            (B) LOCATION:617..623
            (D) OTHER INFORMATION:/standard_name= "-10"
                /label= -10_s (ix) FEATURE:
            (A) NAME/KEY: -35_signal
            (B) LOCATION:594..599
            (D) OTHER INFORMATION:/standard_name= "-35_s"
                /label= -35_s (ix) FEATURE:
            (A) NAME/KEY: promoter
            (B) LOCATION:454..1131
            (D) OTHER INFORMATION:/function= "Promoter"
                /standard_name= "promoter ApxIV"
                /label= promoter (xi) SEQUENCE DESCRIPTION: SEQ ID NO: 5:

```
ATC GAT ATG CCG CCG GGT ACG GGC GAT ATC CAA CTT ACT CTT TCG CAA         48
Ile Asp Met Pro Pro Gly Thr Gly Asp Ile Gln Leu Thr Leu Ser Gln
   1385               1390                1395

CAA ATT CCG GTT ACC GGT GCG GTG GTG GTA ACC ACT CCG CAA GAT ATT         96
Gln Ile Pro Val Thr Gly Ala Val Val Val Thr Thr Pro Gln Asp Ile
1400                1405                1410                1415

GCG TTA TTA GAT GCG GTG AAA GGT ATT TCA ATG TTC CAA AAA GTG TCG        144
Ala Leu Leu Asp Ala Val Lys Gly Ile Ser Met Phe Gln Lys Val Ser
                1420                1425                1430

GTA CCG GTC TTA GGT ATC ATT GAA AAT ATG AGC GTA CAT ATC TGC CAA        192
Val Pro Val Leu Gly Ile Ile Glu Asn Met Ser Val His Ile Cys Gln
   1435                1440                1445

AAT TGC GGT CAC CAC GAA GAT ATT TTC GGC ACC GGC GGT GCG GAG AAA        240
Asn Cys Gly His His Glu Asp Ile Phe Gly Thr Gly Gly Ala Glu Lys
1450                1455                1460

GTG GCG AAG AAA TAC GGT ACT AAA GTA TTA GGA CAA ATG CCG TTG CAT        288
Val Ala Lys Lys Tyr Gly Thr Lys Val Leu Gly Gln Met Pro Leu His
   1465                1470                1475

ATT CGC TTA CGT CAA GAT TTG GAT GCC GGC ACA CCG ACC GTC GTT GCG        336
```

```
Ile Arg Leu Arg Gln Asp Leu Asp Ala Gly Thr Pro Thr Val Val Ala
1480                1485                1490                1495

GCA CCG GAA CAC GAA ACC AGC CGA GCC TAT ATT GAA TTA GCG GCA AAA         384
Ala Pro Glu His Glu Thr Ser Arg Ala Tyr Ile Glu Leu Ala Ala Lys
            1500                1505                1510

GTC GCT TCG GAA TTA TAC TGG CAA GGT TCG GTT ATC CCG TCT GAA ATT         432
Val Ala Ser Glu Leu Tyr Trp Gln Gly Ser Val Ile Pro Ser Glu Ile
            1515                1520                1525

ATG ATT CGT GAA GTA AAA TAA GTTTTAATAA CCACGAAAAC ACAAAGAACA            483
Met Ile Arg Glu Val Lys *
            1530

CAAGCGGTAG AATTTGCAGA AAAATTTGCA AATCCTACCG CTTTTTTATT AGTACGATTC       543

GCTGTTGGAC TGCTATTTGA TTTGGTTTGT CAGGATATTA TGTTATTGTA ATGAAATGTT       603

AGTGAATTAT TTTTATTAAT TTGAAAGGAA ACAAATGAA ATAAAAAAA CGTTACATTG         663

CGCTGTTGGT CTTAGGTGTC GTTATCAGCT ATGCCTGGTA TCAAAATTAT CAATGGGAAC       723

AGCTGATGTT AAGCGGTTAT TGTGAAAAGG ACGGAAGTTA TTTTGATGAT AGGCATACGA       783

AGCAAGAACT GATTGATAGG GCAATTAACT ATATGCTGGA GCATCAATCT AAAAAAACAT       843

ACGATGCTTA TACTGATGAA CCTTTAGAAA TAAAACCATA TTTAACAATA GAGGAATTTA       903

AAAAACTCAA TCCAAATTGT TGTGAAATTA CCTCATGGCC AGCAGATGCA GTTCCACAAG       963

ATTGGGATGT TCGTGTGGAA GGTAAGGCAT ATAGGTATGT AATCGTAAAA TATTTAAGAA       1023

CCTTAGCAAA TAGAGAACCT GAACGATGGG AAACTAGTAT TGTTTTTGAT AATTGCGGCA       1083

ATCCTAAAAG AGCAAGCTAC TTATATTATT TAAAGAGAGA AATTTATT ATG ACA AAA       1140
                                                    Met Thr Lys
                                                        1

TTA ACT ATG CAA GAT GTG ACC AAT TTA TAT TTA TAT AAA ACG AAA ACT         1188
Leu Thr Met Gln Asp Val Thr Asn Leu Tyr Leu Tyr Lys Thr Lys Thr
    5                   10                  15

CTA CCT AAA GAT AGA TTG GAT GAT TCA CTT ATT TCT GAA ATA GGA AAA         1236
Leu Pro Lys Asp Arg Leu Asp Asp Ser Leu Ile Ser Glu Ile Gly Lys
    20                  25                  30                  35

GGA GAT GAT GAT ATT GAT AGA AAA GAA TTT ATG GTG GGG CCG GGA CGT         1284
Gly Asp Asp Asp Ile Asp Arg Lys Glu Phe Met Val Gly Pro Gly Arg
                40                  45                  50

TTT GTG ACC GCT GAT AAC TTT AGC GTT GTA AGA GAT TTT TTT AAT GCT         1332
Phe Val Thr Ala Asp Asn Phe Ser Val Val Arg Asp Phe Phe Asn Ala
        55                  60                  65

GGG AAA TCA CGC ATT ATT GCG CCG CAA GTC CCG CCT ATT CGT TCA CAG         1380
Gly Lys Ser Arg Ile Ile Ala Pro Gln Val Pro Pro Ile Arg Ser Gln
            70                  75                  80

CAG GAA AAA ATC TTG GTC GGT TTA AAA CCG GGC AAA TAT TCC AAA GCG         1428
Gln Glu Lys Ile Leu Val Gly Leu Lys Pro Gly Lys Tyr Ser Lys Ala
85                  90                  95

CAG ATA TTG GAA ATG CTG GGT TAT ACG AAA GGC GGA GAA GTG TAA AAT         1476
Gln Ile Leu Glu Met Leu Gly Tyr Thr Lys Gly Gly Glu Val Val Asn
100                 105                 110                 115

GGC ATG TTT GCC GGT GAA GTC CAG ACA TTA GGC TTT TAT GAC GAT GGC         1524
Gly Met Phe Ala Gly Glu Val Gln Thr Leu Gly Phe Tyr Asp Asp Gly
                120                 125                 130

AAA GGG GAT TTA CTC GAA CGC GCC TAT ATC TGG AAT ACC ACA GGA TTT         1572
Lys Gly Asp Leu Leu Glu Arg Ala Tyr Ile Trp Asn Thr Thr Gly Phe
            135                 140                 145

AAA ATG AGC GAC AAT GCC TTT TTT GTT ATA GAA GAA TCA GGC AAA CGC         1620
Lys Met Ser Asp Asn Ala Phe Phe Val Ile Glu Glu Ser Gly Lys Arg
            150                 155                 160

TAT ATT GAA AAC TTT GGT ATT GAA CCT CTT GGT AAG CAA GAA GAT TTT         1668
```

-continued

```
                Tyr Ile Glu Asn Phe Gly Ile Glu Pro Leu Gly Lys Gln Glu Asp Phe
                165                 170                 175

GAT TTT GTC GGC GGC TTT TGG TCT AAC TTA GTG AAT CGT GGT TTG GAA              1716
Asp Phe Val Gly Gly Phe Trp Ser Asn Leu Val Asn Arg Gly Leu Glu
180                 185                 190                 195

AGT ATT ATC GAC CCA TCC GGT ATC GGT GGA ACG GTA AAC CTT AAC TTT              1764
Ser Ile Ile Asp Pro Ser Gly Ile Gly Gly Thr Val Asn Leu Asn Phe
                200                 205                 210

ACC GGC GAG GTG GAA ACC TAC ACG TTA GAC GAA ACA AGG TTT AAA GCG              1812
Thr Gly Glu Val Glu Thr Tyr Thr Leu Asp Glu Thr Arg Phe Lys Ala
            215                 220                 225

GAA GCG GCG AAG AAA AGC CAT TGG AGT TTA GTG AAT GCG GCG AAA GTA              1860
Glu Ala Ala Lys Lys Ser His Trp Ser Leu Val Asn Ala Ala Lys Val
        230                 235                 240

TAC GGC GGT TTA GAC CAA ATT ATT AAA AAA CTA TGG GAC AGT GGC TCA              1908
Tyr Gly Gly Leu Asp Gln Ile Ile Lys Lys Leu Trp Asp Ser Gly Ser
245                 250                 255

ATT AAG CAT TTA TAT CAA GAT AAA GAT ACG GGC AAA TTA AAA CCG ATT              1956
Ile Lys His Leu Tyr Gln Asp Lys Asp Thr Gly Lys Leu Lys Pro Ile
260                 265                 270                 275

ATT TAC GGC ACG GCC GGC AAC GAC AGT AAG ATT GAA GGC ACT AAA ATC              2004
Ile Tyr Gly Thr Ala Gly Asn Asp Ser Lys Ile Glu Gly Thr Lys Ile
                280                 285                 290

ACC CGT AGG ATT GCG GGT AAA GAA GTT ACG CTT GAT ATT GCC AAT CAG              2052
Thr Arg Arg Ile Ala Gly Lys Glu Val Thr Leu Asp Ile Ala Asn Gln
            295                 300                 305

AAA ATT GAA AAA GGC GTG TTA GAG AAA TTG GGG CTG TCT GTT AGT GGT              2100
Lys Ile Glu Lys Gly Val Leu Glu Lys Leu Gly Leu Ser Val Ser Gly
        310                 315                 320

TCG GAT ATC ATT AAA TTG TTG TTT GGA GCA TTG ACT CCA ACT TTA AAT              2148
Ser Asp Ile Ile Lys Leu Leu Phe Gly Ala Leu Thr Pro Thr Leu Asn
325                 330                 335

AGA ATG TTG CTA TCA CAA CTT ATC CAG TCT TTT TCC GAT AGC TTG GCT              2196
Arg Met Leu Leu Ser Gln Leu Ile Gln Ser Phe Ser Asp Ser Leu Ala
340                 345                 350                 355

AAA CTT GAT AAT CCC TTA GCC CCT TAC ACT AAA AAT GGC GTG GTT TAT              2244
Lys Leu Asp Asn Pro Leu Ala Pro Tyr Thr Lys Asn Gly Val Val Tyr
                360                 365                 370

GTC ACC GGC AAA GGG AAT GAT GTG CTT AAA GGA ACT GAA CAT GAG GAT              2292
Val Thr Gly Lys Gly Asn Asp Val Leu Lys Gly Thr Glu His Glu Asp
            375                 380                 385

TTG TTT CTC GGT GGT GAG GGG AAT GAT ACT TAT TAT GCG AGA GTA GGC              2340
Leu Phe Leu Gly Gly Glu Gly Asn Asp Thr Tyr Tyr Ala Arg Val Gly
        390                 395                 400

GAT ACA ATT GAA GAC GCC GAC GGC AAA GGT AAA GTC TAT TTT GTG AGA              2388
Asp Thr Ile Glu Asp Ala Asp Gly Lys Gly Lys Val Tyr Phe Val Arg
405                 410                 415

GAA AAA GGG GTA CCT AAG GCG GAT CCT AAG CGG GTA GAG TTT AGC GAG              2436
Glu Lys Gly Val Pro Lys Ala Asp Pro Lys Arg Val Glu Phe Ser Glu
420                 425                 430                 435

TAC ATA ACG AAA GAA GAA ATA AAA GAG GTT GAA AAG GGG TTA TTA ACT              2484
Tyr Ile Thr Lys Glu Glu Ile Lys Glu Val Glu Lys Gly Leu Leu Thr
                440                 445                 450

TAC GCA GTT TTA GAA AAT TAT AAT TGG GAA GAG AAA ACG GCG ACT TTC              2532
Tyr Ala Val Leu Glu Asn Tyr Asn Trp Glu Glu Lys Thr Ala Thr Phe
            455                 460                 465

GCT CAT GCG ACT ATG CTT AAT GAG CTT TTT ACT GAT TAT ACT AAT TAT              2580
Ala His Ala Thr Met Leu Asn Glu Leu Phe Thr Asp Tyr Thr Asn Tyr
        470                 475                 480

CGT TAT GAA GTT AAA GGA CTA AAA TTG CCC GCC GTT AAA AAG TTA AAA              2628
```

|     |     |     |     |     |     |     |     |     |     |     |     |      |
|-----|-----|-----|-----|-----|-----|-----|-----|-----|-----|-----|-----|------|
| Arg | Tyr | Glu | Val | Lys | Gly | Leu | Lys | Leu | Pro | Ala | Val | Lys Lys Leu Lys |
|     | 485 |     |     |     | 490 |     |     |     | 495 |     |     |      |

| AGT | CCG | TTG | GTG | GAG | TTT | ACA | GCT | GAT | TTA | TTA | ACT | GTT | ACG | CCT | ATT | 2676 |
|-----|-----|-----|-----|-----|-----|-----|-----|-----|-----|-----|-----|-----|-----|-----|-----|------|
| Ser | Pro | Leu | Val | Glu | Phe | Thr | Ala | Asp | Leu | Leu | Thr | Val | Thr | Pro | Ile |      |
| 500 |     |     |     |     | 505 |     |     |     |     | 510 |     |     |     |     | 515 |      |

| GAC | GAA | AAC | GGA | AAA | GCA | CTT | AGC | GAA | AAA | AGT | ATT | ACG | GTT | AAA | AAT | 2724 |
| Asp | Glu | Asn | Gly | Lys | Ala | Leu | Ser | Glu | Lys | Ser | Ile | Thr | Val | Lys | Asn |      |
|     |     |     |     | 520 |     |     |     |     | 525 |     |     |     |     | 530 |     |      |

| TTT | AAA | AAT | GGT | GAT | TTA | GGA | ATA | AGG | TTG | TTG | GAT | CCT | AAT | AGC | TAT | 2772 |
| Phe | Lys | Asn | Gly | Asp | Leu | Gly | Ile | Arg | Leu | Leu | Asp | Pro | Asn | Ser | Tyr |      |
|     |     |     | 535 |     |     |     |     | 540 |     |     |     |     | 545 |     |     |      |

| TAT | TAT | TTC | CTT | GAA | GGC | CAA | GAT | ACG | GGT | TTT | TAT | GGT | CCT | GCT | TTT | 2820 |
| Tyr | Tyr | Phe | Leu | Glu | Gly | Gln | Asp | Thr | Gly | Phe | Tyr | Gly | Pro | Ala | Phe |      |
|     |     | 550 |     |     |     |     | 555 |     |     |     |     | 560 |     |     |     |      |

| TAT | ATT | GAA | CGA | AAA | AAC | GGT | GGC | GGC | GCT | AAA | AAT | AAC | TCG | TCG | GGA | 2868 |
| Tyr | Ile | Glu | Arg | Lys | Asn | Gly | Gly | Gly | Ala | Lys | Asn | Asn | Ser | Ser | Gly |      |
|     | 565 |     |     |     |     | 570 |     |     |     |     | 575 |     |     |     |     |      |

| GCA | GGA | AAT | AGC | AAA | GAT | TGG | GGC | GGG | AAC | GGG | CAT | GGA | AAT | CAC | CGA | 2916 |
| Ala | Gly | Asn | Ser | Lys | Asp | Trp | Gly | Gly | Asn | Gly | His | Gly | Asn | His | Arg |      |
| 580 |     |     |     | 585 |     |     |     |     | 590 |     |     |     |     | 595 |     |      |

| AAT | AAT | GCC | TCC | GAC | CTG | AAT | AAA | CCG | GAC | GGA | AAT | AAT | GGG | AAT | AAC | 2964 |
| Asn | Asn | Ala | Ser | Asp | Leu | Asn | Lys | Pro | Asp | Gly | Asn | Asn | Gly | Asn | Asn |      |
|     |     |     | 600 |     |     |     |     | 605 |     |     |     |     | 610 |     |     |      |

| CAA | AAT | AAC | GGA | AGC | AAT | CAA | GAT | AAT | CAT | AGC | GAT | GTG | AAT | GCG | CCA | 3012 |
| Gln | Asn | Asn | Gly | Ser | Asn | Gln | Asp | Asn | His | Ser | Asp | Val | Asn | Ala | Pro |      |
|     |     | 615 |     |     |     |     | 620 |     |     |     |     | 625 |     |     |     |      |

| AAT | AAC | CCG | GGA | CGT | AAC | TAT | GAT | ATT | TAC | GAT | CCT | TTA | GCT | TTA | GAT | 3060 |
| Asn | Asn | Pro | Gly | Arg | Asn | Tyr | Asp | Ile | Tyr | Asp | Pro | Leu | Ala | Leu | Asp |      |
|     | 630 |     |     |     |     | 635 |     |     |     |     | 640 |     |     |     |     |      |

| TTA | GAT | GGA | GAT | GGG | CTT | GAA | ACC | GTG | TCG | ATG | AAC | GGG | CGA | CAA | GGC | 3108 |
| Leu | Asp | Gly | Asp | Gly | Leu | Glu | Thr | Val | Ser | Met | Asn | Gly | Arg | Gln | Gly |      |
| 645 |     |     |     |     | 650 |     |     |     |     | 655 |     |     |     |     |     |      |

| GCG | TTA | TTC | GAT | CAT | GAA | GGA | AAA | GGT | ATT | CGT | ACC | GCA | ACG | GGC | TGG | 3156 |
| Ala | Leu | Phe | Asp | His | Glu | Gly | Lys | Gly | Ile | Arg | Thr | Ala | Thr | Gly | Trp |      |
| 660 |     |     |     |     | 665 |     |     |     |     | 670 |     |     |     |     | 675 |      |

| CTC | GCT | GCG | GAT | GAC | GGT | TTT | TTA | GTG | TTA | GAT | CGT | AAC | CAA | GAC | GGC | 3204 |
| Leu | Ala | Ala | Asp | Asp | Gly | Phe | Leu | Val | Leu | Asp | Arg | Asn | Gln | Asp | Gly |      |
|     |     |     |     | 680 |     |     |     |     | 685 |     |     |     |     | 690 |     |      |

| ATT | ATT | AAT | GAT | ATA | AGC | GAG | TTA | TTT | AGT | AAT | AAA | AAT | CAA | CTT | TCC | 3252 |
| Ile | Ile | Asn | Asp | Ile | Ser | Glu | Leu | Phe | Ser | Asn | Lys | Asn | Gln | Leu | Ser |      |
|     |     |     | 695 |     |     |     |     | 700 |     |     |     |     | 705 |     |     |      |

| GAC | GGC | AGT | ATT | TCT | GCA | CAC | GGT | TTT | GCG | ACA | TTA | GCC | GAT | TTG | GAT | 3300 |
| Asp | Gly | Ser | Ile | Ser | Ala | His | Gly | Phe | Ala | Thr | Leu | Ala | Asp | Leu | Asp |      |
|     |     | 710 |     |     |     |     | 715 |     |     |     |     | 720 |     |     |     |      |

| ACA | AAC | CAA | GAT | CAG | CGT | ATC | GAC | CAA | AAT | GAT | AAG | CTG | TTT | TCT | AAA | 3348 |
| Thr | Asn | Gln | Asp | Gln | Arg | Ile | Asp | Gln | Asn | Asp | Lys | Leu | Phe | Ser | Lys |      |
|     | 725 |     |     |     |     | 730 |     |     |     |     | 735 |     |     |     |     |      |

| CTC | CAA | ATT | TGG | CGG | GAT | TTA | AAT | CAA | AAC | GGT | TTT | AGT | GAA | GCG | AAT | 3396 |
| Leu | Gln | Ile | Trp | Arg | Asp | Leu | Asn | Gln | Asn | Gly | Phe | Ser | Glu | Ala | Asn |      |
| 740 |     |     |     |     | 745 |     |     |     |     | 750 |     |     |     |     | 755 |      |

| GAG | CTG | TTT | AGC | TTA | GAA | AGT | TTG | AAT | ATT | AAA | TCT | TTA | CAT | ACC | GCC | 3444 |
| Glu | Leu | Phe | Ser | Leu | Glu | Ser | Leu | Asn | Ile | Lys | Ser | Leu | His | Thr | Ala |      |
|     |     |     |     | 760 |     |     |     |     | 765 |     |     |     |     | 770 |     |      |

| TAT | GAA | GAG | CGT | AAT | GAT | TTT | CTA | GCG | GGC | AAT | AAT | ATC | CTT | GCT | CAG | 3492 |
| Tyr | Glu | Glu | Arg | Asn | Asp | Phe | Leu | Ala | Gly | Asn | Asn | Ile | Leu | Ala | Gln |      |
|     |     |     | 775 |     |     |     |     | 780 |     |     |     |     | 785 |     |     |      |

| CTT | GGG | AAG | TAT | GAA | AAA | ACG | GAC | GGT | ACT | TTT | GCA | CAA | ATG | GGC | GAT | 3540 |
| Leu | Gly | Lys | Tyr | Glu | Lys | Thr | Asp | Gly | Thr | Phe | Ala | Gln | Met | Gly | Asp |      |
|     |     | 790 |     |     |     |     | 795 |     |     |     |     | 800 |     |     |     |      |

| TTA | AAT | TTC | AGT | TTT | AAC | CCG | TTT | TAT | AGC | CGA | TTT | ACC | GAA | GCG | TTA | 3588 |

-continued

```
            Leu Asn Phe Ser Phe Asn Pro Phe Tyr Ser Arg Phe Thr Glu Ala Leu
                805                 810                 815

AAT TTA ACC GAG CAA CAA CGT CGC ACA ATT AAT CTA ACC GGC ACC GGT          3636
Asn Leu Thr Glu Gln Gln Arg Arg Thr Ile Asn Leu Thr Gly Thr Gly
820                 825                 830                 835

CGG GTT CGG GAT TTG CGT GAA GCC GCC GCA CTT TCT GAG GAG TTG GCT          3684
Arg Val Arg Asp Leu Arg Glu Ala Ala Ala Leu Ser Glu Glu Leu Ala
                840                 845                 850

GCT TTA TTA CAA CAG TAC ACT AAG GCC TCC GAT TTT CAG GCA CAA CGA          3732
Ala Leu Leu Gln Gln Tyr Thr Lys Ala Ser Asp Phe Gln Ala Gln Arg
                855                 860                 865

GAA TTA TTG CCT GCC ATT TTA GAT AAA TGG GCG GCA ACG GAT TTA CAG          3780
Glu Leu Leu Pro Ala Ile Leu Asp Lys Trp Ala Ala Thr Asp Leu Gln
                870                 875                 880

TAT CAA CAT TAT GAT AAA ACA TTA CTT AAA ACG GTA GAA AGT ACC GAT          3828
Tyr Gln His Tyr Asp Lys Thr Leu Leu Lys Thr Val Glu Ser Thr Asp
                885                 890                 895

AGT AGT GCT TCT GTC GTT AGA GTC ACG CCT TCT CAA TTA AGT AGT ATA          3876
Ser Ser Ala Ser Val Val Arg Val Thr Pro Ser Gln Leu Ser Ser Ile
900                 905                 910                 915

CGC AAT GCA AAG CAT GAT CCT ACC GTT ATG CAA AAC TTT GAA CAG AGT          3924
Arg Asn Ala Lys His Asp Pro Thr Val Met Gln Asn Phe Glu Gln Ser
                920                 925                 930

AAG GCA AAA ATT GCG ACT TTA AAT TCG CTC TAC GGG TTA AAT ATC GAT          3972
Lys Ala Lys Ile Ala Thr Leu Asn Ser Leu Tyr Gly Leu Asn Ile Asp
                935                 940                 945

CAA CTT TAT TAC ACG ACG GAT AAA GAC ATT CGC TAT ATT ACT GAT AAA          4020
Gln Leu Tyr Tyr Thr Thr Asp Lys Asp Ile Arg Tyr Ile Thr Asp Lys
                950                 955                 960

GTG AAT AAT ATG TAT CAA ACA ACC GTA GAA CTT GCC TAC CGT TCT TTA          4068
Val Asn Asn Met Tyr Gln Thr Thr Val Glu Leu Ala Tyr Arg Ser Leu
965                 970                 975

CTT TTA CAA ACG CGT TTG AAG AAA TAT GTT TAT AGC GTT AAT GCG AAA          4116
Leu Leu Gln Thr Arg Leu Lys Lys Tyr Val Tyr Ser Val Asn Ala Lys
980                 985                 990                 995

CAA TTC GAA GGG AAA TGG GTA ACC GAT TAT TCT CGT ACT GAA GCC TTA          4164
Gln Phe Glu Gly Lys Trp Val Thr Asp Tyr Ser Arg Thr Glu Ala Leu
                1000                1005                1010

TTT AAC TCT ACT TTT AAA CAA TCG CCT GAA AAT GCA TTA TAT GAT TTA          4212
Phe Asn Ser Thr Phe Lys Gln Ser Pro Glu Asn Ala Leu Tyr Asp Leu
                1015                1020                1025

AGC GAA TAC CTT TCT TTC TTT AAC GAT CCT ACG GAA TGG AAA GAA GGG          4260
Ser Glu Tyr Leu Ser Phe Phe Asn Asp Pro Thr Glu Trp Lys Glu Gly
                1030                1035                1040

CTA TTA CTG TTA AGC CGT TAT ATA GAT TAT GCT AAA GCA CAA GGA TTT          4308
Leu Leu Leu Leu Ser Arg Tyr Ile Asp Tyr Ala Lys Ala Gln Gly Phe
                1045                1050                1055

TAT GAA AAC TGG GCG GCT ACT TCT AAC TTA ACT ATT GCC CGT TTA AGA          4356
Tyr Glu Asn Trp Ala Ala Thr Ser Asn Leu Thr Ile Ala Arg Leu Arg
1060                1065                1070                1075

GAG GCT GGA GTA ATT TTT GCA GAA TCG ACG GAT TTA AAA GGC GAT GAA          4404
Glu Ala Gly Val Ile Phe Ala Glu Ser Thr Asp Leu Lys Gly Asp Glu
                1080                1085                1090

AAA AAT AAT ATT TTG TTA GGT AGC CAA AAA GAT AAT AAC TTA TCG GGT          4452
Lys Asn Asn Ile Leu Leu Gly Ser Gln Lys Asp Asn Asn Leu Ser Gly
                1095                1100                1105

AGT GCA GGT GAT GAT CTA CTT ATC GGC GGA GAG GGT AAT GAT ACG TTA          4500
Ser Ala Gly Asp Asp Leu Leu Ile Gly Gly Glu Gly Asn Asp Thr Leu
                1110                1115                1120

AAA GGC AGC TAC GGT GCA GAC ACC TAT ATC TTT AGC AAA GGA CAC GGA          4548
```

-continued

| | | | | | | | | | | | | |
|---|---|---|---|---|---|---|---|---|---|---|---|---|
| Lys | Gly | Ser | Tyr | Gly | Ala | Asp | Thr | Tyr | Ile | Phe | Ser | Lys | Gly | His | Gly |
| | | 1125 | | | | 1130 | | | | 1135 | | | | | |

```
CAG GAT ATC GTT TAT GAA GAT ACC AAT AAT GAT AAC CGC GCA AGA GAT      4596
Gln Asp Ile Val Tyr Glu Asp Thr Asn Asn Asp Asn Arg Ala Arg Asp
1140              1145              1150              1155

ATC GAC ACC TTA AAA TTT ACC GAT GTG AAT TAT GCG GAA GTG AAG TTT      4644
Ile Asp Thr Leu Lys Phe Thr Asp Val Asn Tyr Ala Glu Val Lys Phe
                  1160              1165              1170

CGA CGA GTA GAT AAT GAC TTA ATG TTA TTC GGT TAT CAT GAT ACG GAT      4692
Arg Arg Val Asp Asn Asp Leu Met Leu Phe Gly Tyr His Asp Thr Asp
            1175              1180              1185

TCG GTC ACG GTA AAA TCC TTC TAC AGC CAT GTA GAT TAT CAA TTT GAC      4740
Ser Val Thr Val Lys Ser Phe Tyr Ser His Val Asp Tyr Gln Phe Asp
        1190              1195              1200

AAA TTG GAG TTT GCT GAC CGC AGT ATA ACT CGC GAT GAA CTG ATT AAA      4788
Lys Leu Glu Phe Ala Asp Arg Ser Ile Thr Arg Asp Glu Leu Ile Lys
    1205              1210              1215

GCA GGG CTT CAT CTA TAC GGC ACC GAT GGC AAT GAT GAT ATA AAG GAT      4836
Ala Gly Leu His Leu Tyr Gly Thr Asp Gly Asn Asp Asp Ile Lys Asp
1220              1225              1230              1235

CAT GCG GAT TGG GAC AGC ATT TTG GAA GGC GGC AAA GGC AAC GAT ATT      4884
His Ala Asp Trp Asp Ser Ile Leu Glu Gly Gly Lys Gly Asn Asp Ile
                  1240              1245              1250

CTA AGA GGT GGC TAC GGT GCG GAC ACC TAT ATC TTT AGC AAA GGA CAC      4932
Leu Arg Gly Gly Tyr Gly Ala Asp Thr Tyr Ile Phe Ser Lys Gly His
            1255              1260              1265

GGA CAG GAT ATC GTT TAT GAA GAT ACC AAT AAT GAT AAC CGC GCA AGA      4980
Gly Gln Asp Ile Val Tyr Glu Asp Thr Asn Asn Asp Asn Arg Ala Arg
        1270              1275              1280

GAT ATC GAC ACC TTA AAA TTT ACT GAT GTG AAT TAT GCG GAA GTG AAA      5028
Asp Ile Asp Thr Leu Lys Phe Thr Asp Val Asn Tyr Ala Glu Val Lys
    1285              1290              1295

TTC CGA CGA GTA GAT AAT GAC TTA ATG TTA TTC GGT TAT CAT GAT ACG      5076
Phe Arg Arg Val Asp Asn Asp Leu Met Leu Phe Gly Tyr His Asp Thr
1300              1305              1310              1315

GAT TCG GTC ACG ATA AAA TCC TTC TAC AAC CAT GTA GAT TAT CAA TTT      5124
Asp Ser Val Thr Ile Lys Ser Phe Tyr Asn His Val Asp Tyr Gln Phe
                  1320              1325              1330

GAC AAA TTG GAA TTT GCT GAC CGC AGT ATA ACT CGT GAT GAA CTA GGT      5172
Asp Lys Leu Glu Phe Ala Asp Arg Ser Ile Thr Arg Asp Glu Leu Gly
            1335              1340              1345

AAA CAA GGT ATG GCA TTA TTT GGC ACT GAC GGT GAT GAT AAT ATC AAC      5220
Lys Gln Gly Met Ala Leu Phe Gly Thr Asp Gly Asp Asp Asn Ile Asn
        1350              1355              1360

GAC TGG GGA CGT AAC TCG GTG ATT GAT GCC GGT GCG GGT AAT GAT ACG      5268
Asp Trp Gly Arg Asn Ser Val Ile Asp Ala Gly Ala Gly Asn Asp Thr
    1365              1370              1375

GTT AAT GGC GGT AAT GGC GAT GAC ACC CTC ATC GGC GGC AAA GGT AAT      5316
Val Asn Gly Gly Asn Gly Asp Asp Thr Leu Ile Gly Gly Lys Gly Asn
1380              1385              1390              1395

GAT ATT CTA AGA GGT GGC TAC GGT GCG GAC ACC TAT ATC TTT AGC AAA      5364
Asp Ile Leu Arg Gly Gly Tyr Gly Ala Asp Thr Tyr Ile Phe Ser Lys
                  1400              1405              1410

GGA CAC GGA CAG GAT ATC GTT TAT GAA GAT ACC AAT AAT GAT AAC CGC      5412
Gly His Gly Gln Asp Ile Val Tyr Glu Asp Thr Asn Asn Asp Asn Arg
            1415              1420              1425

GCA AGA GAT ATC GAC ACC TTA AAA TTT ACC GAT GTG AAT TAT GCG GAA      5460
Ala Arg Asp Ile Asp Thr Leu Lys Phe Thr Asp Val Asn Tyr Ala Glu
        1430              1435              1440

GTG AAA TTC CGA CGA GTA GAT AAT GAC TTA ATG TTA TTC GGT TAT CAT      5508
```

```
Val Lys Phe Arg Arg Val Asp Asn Asp Leu Met Leu Phe Gly Tyr His
    1445                1450                1455

GAT ACG GAT TCG GTC ACG GTA AAA TCC TTC TAC AGC CAT GTA GAT TAT        5556
Asp Thr Asp Ser Val Thr Val Lys Ser Phe Tyr Ser His Val Asp Tyr
1460                1465                1470                1475

CAA TTT GAC AAA TTG GAG TTT GCT GAC CGC AGT ATA ACT CGC GAT GAA        5604
Gln Phe Asp Lys Leu Glu Phe Ala Asp Arg Ser Ile Thr Arg Asp Glu
                1480                1485                1490

CTG ATT AAA GCA GGG CTT CAT CTA TAC GGC ACC GAT GGC AAT GAT GAT        5652
Leu Ile Lys Ala Gly Leu His Leu Tyr Gly Thr Asp Gly Asn Asp Asp
        1495                1500                1505

ATA AAG GAT CAT GCG GAT TGG GAC AGC ATT TTG GAA GGC GGC AAA GGC        5700
Ile Lys Asp His Ala Asp Trp Asp Ser Ile Leu Glu Gly Gly Lys Gly
1510                1515                1520

AAC GAT ATT CTA AGA GGT GGC TAC GGT GCG GAC ACC TAT ATC TTT AGC        5748
Asn Asp Ile Leu Arg Gly Gly Tyr Gly Ala Asp Thr Tyr Ile Phe Ser
            1525                1530                1535

AAA GGA CAC GGA CAG GAT ATC GTT TAT GAA GAT ACC AAT AAT GAT AAC        5796
Lys Gly His Gly Gln Asp Ile Val Tyr Glu Asp Thr Asn Asn Asp Asn
1540                1545                1550                1555

CGA GCA AGA GAT ATC GAC ACC TTA AAA TTT ACT GAT GTG AAT TAT GCG        5844
Arg Ala Arg Asp Ile Asp Thr Leu Lys Phe Thr Asp Val Asn Tyr Ala
                1560                1565                1570

GAA GTG AAA TTC CGA CGA GTA GAT AAT GAC TTA ATG TTA TTC GGT TAT        5892
Glu Val Lys Phe Arg Arg Val Asp Asn Asp Leu Met Leu Phe Gly Tyr
        1575                1580                1585

CAT GAT ACG GAT TCG GTC ACG ATA AAA TCC TTC TAC AAC CAT GTA GAT        5940
His Asp Thr Asp Ser Val Thr Ile Lys Ser Phe Tyr Asn His Val Asp
            1590                1595                1600

TAT CAA TTT GAC AAA TTG GAA TTT GCT GAC CGC AGT ATA ACT CGT GAT        5988
Tyr Gln Phe Asp Lys Leu Glu Phe Ala Asp Arg Ser Ile Thr Arg Asp
1605                1610                1615

GAA CTA GGT AAA CAA GGT ATG GCA TTA TTT GGC ACT GAC GGT GAT GAT        6036
Glu Leu Gly Lys Gln Gly Met Ala Leu Phe Gly Thr Asp Gly Asp Asp
1620                1625                1630                1635

AAT ATC AAC GAC TGG GGA CGT AAC TCG GTG ATT GAT GCC GGT GCG GGT        6084
Asn Ile Asn Asp Trp Gly Arg Asn Ser Val Ile Asp Ala Gly Ala Gly
                1640                1645                1650

AAT GAT ACG GTT AAT GGC GGT AAT GGC GAT GAC ACC CTC ATC GGC GGC        6132
Asn Asp Thr Val Asn Gly Gly Asn Gly Asp Asp Thr Leu Ile Gly Gly
        1655                1660                1665

AAA GGT AAT GAT ATT CTA AGA GGT GGC TAC GGT GCG GAC ACC TAT ATC        6180
Lys Gly Asn Asp Ile Leu Arg Gly Gly Tyr Gly Ala Asp Thr Tyr Ile
            1670                1675                1680

TTT AGC AAA GGA CAC GGA CAG GAT ATC GTT TAT GAA GAT ACC AAT AAT        6228
Phe Ser Lys Gly His Gly Gln Asp Ile Val Tyr Glu Asp Thr Asn Asn
1685                1690                1695

GAT AAC CGC GCA AGA GAT ATC GAC ACC TTA AAA TTT ACT GAT ATT AAT        6276
Asp Asn Arg Ala Arg Asp Ile Asp Thr Leu Lys Phe Thr Asp Ile Asn
1700                1705                1710                1715

TTA TCC GAA CTT TGG TTT AGC CGA GAA AAT AAC GAT TTG ATT ATT AAA        6324
Leu Ser Glu Leu Trp Phe Ser Arg Glu Asn Asn Asp Leu Ile Ile Lys
                1720                1725                1730

TCA TTA TTA AGT GAG GAT AAA GTC ACG GTT CAA AAT TGG TAT TCA CAC        6372
Ser Leu Leu Ser Glu Asp Lys Val Thr Val Gln Asn Trp Tyr Ser His
        1735                1740                1745

CAA GAT CAT AAA ATA GAA AAT ATT CGT TTA TCG AAT GAG CAA ACG TTG        6420
Gln Asp His Lys Ile Glu Asn Ile Arg Leu Ser Asn Glu Gln Thr Leu
            1750                1755                1760

GTG AGC ACT CAG GTG GAG AAG ATG GTT GAG TCG ATG GCC GGC TTT GCT        6468
```

```
Val Ser Thr Gln Val Glu Lys Met Val Glu Ser Met Ala Gly Phe Ala
    1765                1770                1775

CAG AAG CAC GGA GGA GAG ATA TCT CTT GTG TCG CTT GAA GAG GTA AAA      6516
Gln Lys His Gly Gly Glu Ile Ser Leu Val Ser Leu Glu Glu Val Lys
    1780                1785                1790                1795

CAA TAT ATC AAT AGC TTA ACA GCT GCT TTA TAA CATACGAAAG AAATCGGCAC    6569
Gln Tyr Ile Asn Ser Leu Thr Ala Ala Leu *
                    1800                1805

AGTTTTTTTG AACTGTGCCG ATTTGATTTT AGTGTAAGAA TATAGCCTGA TTTTAAGAAA    6629

TTTACTCTTG GCTAATAACT ATTTCCCATT TTATAAGTTA TTGACGGATG GTTTTATCAA    6689

ATATGAGATC AAATCTTATT TTAAATTCGC TTTCCATTAA GCGATAT                  6736

(2) INFORMATION FOR SEQ ID NO: 6:

(i) SEQUENCE CHARACTERISTICS:
        (A) LENGTH:  150 amino acids
        (B) TYPE: amino acid
        (D) TOPOLOGY: linear (ii) MOLECULE TYPE: protein (xi) SEQUENCE DESCRIPTION: SEQ ID NO: 6:

Ile Asp Met Pro Pro Gly Thr Gly Asp Ile Gln Leu Thr Leu Ser Gln
1               5                   10                  15

Gln Ile Pro Val Thr Gly Ala Val Val Thr Thr Pro Gln Asp Ile
            20                  25                  30

Ala Leu Leu Asp Ala Val Lys Gly Ile Ser Met Phe Gln Lys Val Ser
            35                  40                  45

Val Pro Val Leu Gly Ile Ile Glu Asn Met Ser Val His Ile Cys Gln
        50                  55                  60

Asn Cys Gly His His Glu Asp Ile Phe Gly Thr Gly Gly Ala Glu Lys
65                  70                  75                  80

Val Ala Lys Lys Tyr Gly Thr Lys Val Leu Gly Gln Met Pro Leu His
                85                  90                  95

Ile Arg Leu Arg Gln Asp Leu Asp Ala Gly Thr Pro Thr Val Val Ala
            100                 105                 110

Ala Pro Glu His Glu Thr Ser Arg Ala Tyr Ile Glu Leu Ala Ala Lys
        115                 120                 125

Val Ala Ser Glu Leu Tyr Trp Gln Gly Ser Val Ile Pro Ser Glu Ile
    130                 135                 140

Met Ile Arg Glu Val Lys
145                 150

(2) INFORMATION FOR SEQ ID NO: 7:

(i) SEQUENCE CHARACTERISTICS:
        (A) LENGTH:  1805 amino acids
        (B) TYPE: amino acid
        (D) TOPOLOGY: linear (ii) MOLECULE TYPE: protein (xi) SEQUENCE DESCRIPTION: SEQ ID NO: 7:

Met Thr Lys Leu Thr Met Gln Asp Val Thr Asn Leu Tyr Leu Tyr Lys
1               5                   10                  15

Thr Lys Thr Leu Pro Lys Asp Arg Leu Asp Asp Ser Leu Ile Ser Glu
            20                  25                  30

Ile Gly Lys Gly Asp Asp Asp Ile Asp Arg Lys Glu Phe Met Val Gly
        35                  40                  45
```

```
Pro Gly Arg Phe Val Thr Ala Asp Asn Phe Ser Val Val Arg Asp Phe
 50                  55                  60

Phe Asn Ala Gly Lys Ser Arg Ile Ile Ala Pro Gln Val Pro Pro Ile
 65                  70                  75                  80

Arg Ser Gln Gln Glu Lys Ile Leu Val Gly Leu Lys Pro Gly Lys Tyr
                 85                  90                  95

Ser Lys Ala Gln Ile Leu Glu Met Leu Gly Tyr Thr Lys Gly Gly Glu
                100                 105                 110

Val Val Asn Gly Met Phe Ala Gly Glu Val Gln Thr Leu Gly Phe Tyr
            115                 120                 125

Asp Asp Gly Lys Gly Asp Leu Leu Glu Arg Ala Tyr Ile Trp Asn Thr
            130                 135                 140

Thr Gly Phe Lys Met Ser Asp Asn Ala Phe Phe Val Ile Glu Glu Ser
145                 150                 155                 160

Gly Lys Arg Tyr Ile Glu Asn Phe Gly Ile Glu Pro Leu Gly Lys Gln
                165                 170                 175

Glu Asp Phe Asp Phe Val Gly Gly Phe Trp Ser Asn Leu Val Asn Arg
            180                 185                 190

Gly Leu Glu Ser Ile Ile Asp Pro Ser Gly Ile Gly Thr Val Asn
            195                 200                 205

Leu Asn Phe Thr Gly Glu Val Glu Thr Tyr Thr Leu Asp Glu Thr Arg
210                 215                 220

Phe Lys Ala Glu Ala Ala Lys Lys Ser His Trp Ser Leu Val Asn Ala
225                 230                 235                 240

Ala Lys Val Tyr Gly Gly Leu Asp Gln Ile Ile Lys Lys Leu Trp Asp
                245                 250                 255

Ser Gly Ser Ile Lys His Leu Tyr Gln Asp Lys Asp Thr Gly Lys Leu
            260                 265                 270

Lys Pro Ile Ile Tyr Gly Thr Ala Gly Asn Asp Ser Lys Ile Glu Gly
            275                 280                 285

Thr Lys Ile Thr Arg Arg Ile Ala Gly Lys Glu Val Thr Leu Asp Ile
290                 295                 300

Ala Asn Gln Lys Ile Glu Lys Gly Val Leu Glu Lys Leu Gly Leu Ser
305                 310                 315                 320

Val Ser Gly Ser Asp Ile Ile Lys Leu Leu Phe Gly Ala Leu Thr Pro
            325                 330                 335

Thr Leu Asn Arg Met Leu Leu Ser Gln Leu Ile Gln Ser Phe Ser Asp
            340                 345                 350

Ser Leu Ala Lys Leu Asp Asn Pro Leu Ala Pro Tyr Thr Lys Asn Gly
            355                 360                 365

Val Val Tyr Val Thr Gly Lys Gly Asn Asp Val Leu Lys Gly Thr Glu
            370                 375                 380

His Glu Asp Leu Phe Leu Gly Gly Glu Gly Asn Asp Thr Tyr Tyr Ala
385                 390                 395                 400

Arg Val Gly Asp Thr Ile Glu Asp Ala Asp Gly Lys Gly Lys Val Tyr
                405                 410                 415

Phe Val Arg Glu Lys Gly Val Pro Lys Ala Asp Pro Lys Arg Val Glu
            420                 425                 430

Phe Ser Glu Tyr Ile Thr Lys Glu Glu Ile Lys Glu Val Glu Lys Gly
            435                 440                 445

Leu Leu Thr Tyr Ala Val Leu Glu Asn Tyr Asn Trp Glu Glu Lys Thr
            450                 455                 460

Ala Thr Phe Ala His Ala Thr Met Leu Asn Glu Leu Phe Thr Asp Tyr
465                 470                 475                 480
```

-continued

```
Thr Asn Tyr Arg Tyr Glu Val Lys Gly Leu Lys Leu Pro Ala Val Lys
            485                 490                 495
Lys Leu Lys Ser Pro Leu Val Glu Phe Thr Ala Asp Leu Leu Thr Val
            500                 505                 510
Thr Pro Ile Asp Glu Asn Gly Lys Ala Leu Ser Glu Lys Ser Ile Thr
            515                 520                 525
Val Lys Asn Phe Lys Asn Gly Asp Leu Gly Ile Arg Leu Leu Asp Pro
530                 535                 540
Asn Ser Tyr Tyr Tyr Phe Leu Glu Gly Gln Asp Thr Gly Phe Tyr Gly
545                 550                 555                 560
Pro Ala Phe Tyr Ile Glu Arg Lys Asn Gly Gly Ala Lys Asn Asn
                565                 570                 575
Ser Ser Gly Ala Gly Asn Ser Lys Asp Trp Gly Gly Asn Gly His Gly
            580                 585                 590
Asn His Arg Asn Asn Ala Ser Asp Leu Asn Lys Pro Asp Gly Asn Asn
            595                 600                 605
Gly Asn Asn Gln Asn Asn Gly Ser Asn Gln Asp Asn His Ser Asp Val
610                 615                 620
Asn Ala Pro Asn Asn Pro Gly Arg Asn Tyr Asp Ile Tyr Asp Pro Leu
625                 630                 635                 640
Ala Leu Asp Leu Asp Gly Asp Gly Leu Glu Thr Val Ser Met Asn Gly
            645                 650                 655
Arg Gln Gly Ala Leu Phe Asp His Glu Gly Lys Gly Ile Arg Thr Ala
            660                 665                 670
Thr Gly Trp Leu Ala Ala Asp Asp Gly Phe Leu Val Leu Asp Arg Asn
            675                 680                 685
Gln Asp Gly Ile Ile Asn Asp Ile Ser Glu Leu Phe Ser Asn Lys Asn
690                 695                 700
Gln Leu Ser Asp Gly Ser Ile Ser Ala His Gly Phe Ala Thr Leu Ala
705                 710                 715                 720
Asp Leu Asp Thr Asn Gln Asp Gln Arg Ile Asp Gln Asn Asp Lys Leu
            725                 730                 735
Phe Ser Lys Leu Gln Ile Trp Arg Asp Leu Asn Gln Asn Gly Phe Ser
            740                 745                 750
Glu Ala Asn Glu Leu Phe Ser Leu Glu Ser Leu Asn Ile Lys Ser Leu
            755                 760                 765
His Thr Ala Tyr Glu Glu Arg Asn Asp Phe Leu Ala Gly Asn Asn Ile
            770                 775                 780
Leu Ala Gln Leu Gly Lys Tyr Glu Lys Thr Asp Gly Thr Phe Ala Gln
785                 790                 795                 800
Met Gly Asp Leu Asn Phe Ser Phe Asn Pro Phe Tyr Ser Arg Phe Thr
            805                 810                 815
Glu Ala Leu Asn Leu Thr Glu Gln Gln Arg Arg Thr Ile Asn Leu Thr
            820                 825                 830
Gly Thr Gly Arg Val Arg Asp Leu Arg Glu Ala Ala Leu Ser Glu
            835                 840                 845
Glu Leu Ala Ala Leu Leu Gln Gln Tyr Thr Lys Ala Ser Asp Phe Gln
            850                 855                 860
Ala Gln Arg Glu Leu Leu Pro Ala Ile Leu Asp Lys Trp Ala Ala Thr
865                 870                 875                 880
Asp Leu Gln Tyr Gln His Tyr Asp Lys Thr Leu Leu Lys Thr Val Glu
            885                 890                 895
Ser Thr Asp Ser Ser Ala Ser Val Val Arg Val Thr Pro Ser Gln Leu
```

```
                900             905             910
Ser Ser Ile Arg Asn Ala Lys His Asp Pro Thr Val Met Gln Asn Phe
            915             920             925
Glu Gln Ser Lys Ala Lys Ile Ala Thr Leu Asn Ser Leu Tyr Gly Leu
        930             935             940
Asn Ile Asp Gln Leu Tyr Tyr Thr Thr Asp Lys Asp Ile Arg Tyr Ile
945             950             955             960
Thr Asp Lys Val Asn Asn Met Tyr Gln Thr Thr Val Glu Leu Ala Tyr
                965             970             975
Arg Ser Leu Leu Leu Gln Thr Arg Leu Lys Lys Tyr Val Tyr Ser Val
            980             985             990
Asn Ala Lys Gln Phe Glu Gly Lys Trp Val Thr Asp Tyr Ser Arg Thr
        995             1000            1005
Glu Ala Leu Phe Asn Ser Thr Phe Lys Gln Ser Pro Glu Asn Ala Leu
    1010            1015            1020
Tyr Asp Leu Ser Glu Tyr Leu Ser Phe Phe Asn Asp Pro Thr Glu Trp
1025            1030            1035            1040
Lys Glu Gly Leu Leu Leu Ser Arg Tyr Ile Asp Tyr Ala Lys Ala
                1045            1050            1055
Gln Gly Phe Tyr Glu Asn Trp Ala Ala Thr Ser Asn Leu Thr Ile Ala
            1060            1065            1070
Arg Leu Arg Glu Ala Gly Val Ile Phe Ala Glu Ser Thr Asp Leu Lys
        1075            1080            1085
Gly Asp Glu Lys Asn Asn Ile Leu Leu Gly Ser Gln Asp Asn Asn
    1090            1095            1100
Leu Ser Gly Ser Ala Gly Asp Asp Leu Leu Ile Gly Gly Glu Gly Asn
1105            1110            1115            1120
Asp Thr Leu Lys Gly Ser Tyr Gly Ala Asp Thr Tyr Ile Phe Ser Lys
                1125            1130            1135
Gly His Gly Gln Asp Ile Val Tyr Glu Asp Thr Asn Asn Asp Asn Arg
            1140            1145            1150
Ala Arg Asp Ile Asp Thr Leu Lys Phe Thr Asp Val Asn Tyr Ala Glu
        1155            1160            1165
Val Lys Phe Arg Arg Val Asp Asn Asp Leu Met Leu Phe Gly Tyr His
    1170            1175            1180
Asp Thr Asp Ser Val Thr Val Lys Ser Phe Tyr Ser His Val Asp Tyr
1185            1190            1195            1200
Gln Phe Asp Lys Leu Glu Phe Ala Asp Arg Ser Ile Thr Arg Asp Glu
                1205            1210            1215
Leu Ile Lys Ala Gly Leu His Leu Tyr Gly Thr Asp Gly Asn Asp Asp
            1220            1225            1230
Ile Lys Asp His Ala Asp Trp Asp Ser Ile Leu Glu Gly Gly Lys Gly
        1235            1240            1245
Asn Asp Ile Leu Arg Gly Gly Tyr Gly Ala Asp Thr Tyr Ile Phe Ser
    1250            1255            1260
Lys Gly His Gly Gln Asp Ile Val Tyr Glu Asp Thr Asn Asn Asp Asn
1265            1270            1275            1280
Arg Ala Arg Asp Ile Asp Thr Leu Lys Phe Thr Asp Val Asn Tyr Ala
                1285            1290            1295
Glu Val Lys Phe Arg Arg Val Asp Asn Asp Leu Met Leu Phe Gly Tyr
            1300            1305            1310
His Asp Thr Asp Ser Val Thr Ile Lys Ser Phe Tyr Asn His Val Asp
        1315            1320            1325
```

-continued

```
Tyr Gln Phe Asp Lys Leu Glu Phe Ala Asp Arg Ser Ile Thr Arg Asp
    1330                1335                1340

Glu Leu Gly Lys Gln Gly Met Ala Leu Phe Gly Thr Asp Gly Asp Asp
    1345                1350                1355                1360

Asn Ile Asn Asp Trp Gly Arg Asn Ser Val Ile Asp Ala Gly Ala Gly
                    1365                1370                1375

Asn Asp Thr Val Asn Gly Gly Asn Gly Asp Asp Thr Leu Ile Gly Gly
                    1380                1385                1390

Lys Gly Asn Asp Ile Leu Arg Gly Gly Tyr Gly Ala Asp Thr Tyr Ile
                    1395                1400                1405

Phe Ser Lys Gly His Gly Gln Asp Ile Val Tyr Glu Asp Thr Asn Asn
                    1410                1415                1420

Asp Asn Arg Ala Arg Asp Ile Asp Thr Leu Lys Phe Thr Asp Val Asn
1425                1430                1435                1440

Tyr Ala Glu Val Lys Phe Arg Arg Val Asp Asn Asp Leu Met Leu Phe
                    1445                1450                1455

Gly Tyr His Asp Thr Asp Ser Val Thr Val Lys Ser Phe Tyr Ser His
                    1460                1465                1470

Val Asp Tyr Gln Phe Asp Lys Leu Glu Phe Ala Asp Arg Ser Ile Thr
                    1475                1480                1485

Arg Asp Glu Leu Ile Lys Ala Gly Leu His Leu Tyr Gly Thr Asp Gly
                    1490                1495                1500

Asn Asp Asp Ile Lys Asp His Ala Asp Trp Asp Ser Ile Leu Glu Gly
1505                1510                1515                1520

Gly Lys Gly Asn Asp Ile Leu Arg Gly Gly Tyr Gly Ala Asp Thr Tyr
                    1525                1530                1535

Ile Phe Ser Lys Gly His Gly Gln Asp Ile Val Tyr Glu Asp Thr Asn
                    1540                1545                1550

Asn Asp Asn Arg Ala Arg Asp Ile Asp Thr Leu Lys Phe Thr Asp Val
                    1555                1560                1565

Asn Tyr Ala Glu Val Lys Phe Arg Arg Val Asp Asn Asp Leu Met Leu
                    1570                1575                1580

Phe Gly Tyr His Asp Thr Asp Ser Val Thr Ile Lys Ser Phe Tyr Asn
1585                1590                1595                1600

His Val Asp Tyr Gln Phe Asp Lys Leu Glu Phe Ala Asp Arg Ser Ile
                    1605                1610                1615

Thr Arg Asp Glu Leu Gly Lys Gln Gly Met Ala Leu Phe Gly Thr Asp
                    1620                1625                1630

Gly Asp Asp Asn Ile Asn Asp Trp Gly Arg Asn Ser Val Ile Asp Ala
                    1635                1640                1645

Gly Ala Gly Asn Asp Thr Val Asn Gly Gly Asn Gly Asp Asp Thr Leu
                    1650                1655                1660

Ile Gly Gly Lys Gly Asn Asp Ile Leu Arg Gly Gly Tyr Gly Ala Asp
1665                1670                1675                1680

Thr Tyr Ile Phe Ser Lys Gly His Gly Gln Asp Ile Val Tyr Glu Asp
                    1685                1690                1695

Thr Asn Asn Asp Asn Arg Ala Arg Asp Ile Asp Thr Leu Lys Phe Thr
                    1700                1705                1710

Asp Ile Asn Leu Ser Glu Leu Trp Phe Ser Arg Glu Asn Asn Asp Leu
                    1715                1720                1725

Ile Ile Lys Ser Leu Leu Ser Glu Asp Lys Val Thr Val Gln Asn Trp
                    1730                1735                1740

Tyr Ser His Gln Asp His Lys Ile Glu Asn Ile Arg Leu Ser Asn Glu
                    1745                1750                1755                1760
```

-continued

```
Gln Thr Leu Val Ser Thr Gln Val Glu Lys Met Val Glu Ser Met Ala
                1765                1770                1775

Gly Phe Ala Gln Lys His Gly Gly Glu Ile Ser Leu Val Ser Leu Glu
            1780                1785                1790

Glu Val Lys Gln Tyr Ile Asn Ser Leu Thr Ala Ala Leu
        1795                1800                1805
```